United States Patent
Gillies et al.

(10) Patent No.: US 7,465,447 B2
(45) Date of Patent: Dec. 16, 2008

(54) FC-ERYTHROPOIETIN FUSION PROTEIN WITH IMPROVED PHARMACOKINETICS

(75) Inventors: Stephen D. Gillies, Carlisle, MA (US); Scott Lauder, Boxborough, MA (US)

(73) Assignee: Merck Patent GmbH, Darmstadt (DE)

( * ) Notice: Subject to any disclaimer, the term of this patent is extended or adjusted under 35 U.S.C. 154(b) by 378 days.

(21) Appl. No.: 11/026,998

(22) Filed: Dec. 30, 2004

(65) Prior Publication Data

US 2005/0192211 A1  Sep. 1, 2005

Related U.S. Application Data

(60) Provisional application No. 60/533,858, filed on Dec. 31, 2003.

(51) Int. Cl.
*A61K 39/00* (2006.01)
*C07K 14/485* (2006.01)

(52) U.S. Cl. .................................. 424/134.1; 530/397

(58) Field of Classification Search ....................... None
See application file for complete search history.

(56) References Cited

U.S. PATENT DOCUMENTS

| | | | |
|---|---|---|---|
| 4,196,265 A | 4/1980 | Koprowski et al. |
| 4,469,797 A | 9/1984 | Albarella |
| 4,667,016 A | 5/1987 | Lai et al. |
| 4,676,980 A | 6/1987 | Segal et al. |
| 4,703,008 A | 10/1987 | Lin |
| 4,816,567 A | 3/1989 | Cabilly et al. |
| 4,946,778 A | 8/1990 | Ladner et al. |
| 4,975,369 A | 12/1990 | Beavers et al. |
| 5,019,368 A | 5/1991 | Epstein et al. |
| 5,082,658 A | 1/1992 | Palladino |
| 5,091,513 A | 2/1992 | Huston et al. |
| 5,114,711 A | 5/1992 | Bell et al. |
| 5,116,964 A | 5/1992 | Capon et al. |
| 5,225,538 A | 7/1993 | Capon et al. |
| 5,225,539 A | 7/1993 | Winter |
| 5,258,498 A | 11/1993 | Huston et al. |
| 5,314,995 A | 5/1994 | Fell, Jr. et al. |
| 5,349,053 A | 9/1994 | Landolfi |
| 5,359,035 A | 10/1994 | Habermann |
| 5,399,346 A | 3/1995 | Anderson et al. |
| 5,428,130 A | 6/1995 | Capon et al. |
| 5,441,868 A | 8/1995 | Lin |
| 5,480,981 A | 1/1996 | Goodwin et al. |
| 5,514,582 A | 5/1996 | Capon et al. |
| 5,541,087 A | 7/1996 | Lo et al. |
| 5,547,933 A | 8/1996 | Lin |
| 5,585,089 A | 12/1996 | Queen et al. |
| 5,585,097 A | 12/1996 | Bolt et al. |
| 5,601,819 A | 2/1997 | Wong et al. |
| 5,609,846 A | 3/1997 | Goldenberg |
| 5,614,184 A | 3/1997 | Sytkowski et al. |
| 5,618,698 A | 4/1997 | Lin |
| 5,624,821 A | 4/1997 | Winter et al. |
| 5,645,835 A | 7/1997 | Fell, Jr. et al. |
| 5,650,150 A | 7/1997 | Gillies |
| 5,677,425 A | 10/1997 | Bodmer et al. |
| 5,679,543 A | 10/1997 | Lawlis |
| 5,688,679 A | 11/1997 | Powell |
| 5,709,859 A | 1/1998 | Aruffo et al. |
| 5,712,120 A | 1/1998 | Rodriguez et al. |
| 5,723,125 A | 3/1998 | Chang et al. |
| 5,726,044 A | 3/1998 | Lo et al. |
| 5,728,552 A | 3/1998 | Fujisawa et al. |
| 5,756,349 A | 5/1998 | Lin |
| 5,770,195 A | 6/1998 | Hudziak et al. |
| 5,807,715 A | 9/1998 | Morrison et al. |
| 5,827,516 A | 10/1998 | Urban et al. |
| 5,827,703 A | 10/1998 | Debs et al. |
| 5,837,821 A | 11/1998 | Wu |
| 5,843,423 A | 12/1998 | Lyman et al. |
| 5,856,298 A | 1/1999 | Strickland |
| 5,888,772 A | 3/1999 | Okasinski et al. |
| 5,888,773 A | 3/1999 | Jost et al. |
| 5,908,626 A | 6/1999 | Chang et al. |
| 5,955,422 A | 9/1999 | Lin |
| 6,086,875 A | 7/2000 | Blumberg et al. |
| 6,100,387 A | 8/2000 | Herrmann et al. |
| 6,169,070 B1 | 1/2001 | Chen et al. |
| 6,277,375 B1 | 8/2001 | Ward |
| 6,281,010 B1 | 8/2001 | Gao et al. |
| 6,284,536 B1 | 9/2001 | Morrison et al. |
| 6,291,158 B1 | 9/2001 | Winter et al. |
| 6,335,176 B1 | 1/2002 | Inglese et al. |
| 6,340,742 B1 | 1/2002 | Burg et al. |
| 6,444,792 B1 | 9/2002 | Gray et al. |
| 6,475,717 B1 | 11/2002 | Enssle et al. |
| 6,485,726 B1 | 11/2002 | Blumberg et al. |
| 6,500,641 B1 | 12/2002 | Chen et al. |
| 6,551,592 B2 | 4/2003 | Lindhofer et al. |
| 6,583,272 B1 | 6/2003 | Bailon |
| 6,586,398 B1 | 7/2003 | Kinstler et al. |
| 6,617,135 B1 | 9/2003 | Gillies et al. |

(Continued)

FOREIGN PATENT DOCUMENTS

AU  21725/88  3/1989

(Continued)

OTHER PUBLICATIONS

Abaza et al., (1992), "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," *Journal of Protein Chemistry*, 11(5):433-444.

(Continued)

*Primary Examiner*—Marianne P. Allen
*Assistant Examiner*—Regina M DeBerry
(74) *Attorney, Agent, or Firm*—Goodwin Procter LLP

(57) ABSTRACT

The present invention provides Fc-erythropoietin ("Fc-EPO") fusion proteins with improved pharmacokinetics. Nucleic acids, cells, and methods relating to the production and practice of the invention are also provided.

4 Claims, 12 Drawing Sheets

U.S. PATENT DOCUMENTS

| | | |
|---|---|---|
| 6,620,413 B1 | 9/2003 | DeSauvage et al. |
| 6,627,615 B1 | 9/2003 | Debs et al. |
| 6,646,113 B1 | 11/2003 | Dreyfuss et al. |
| 6,750,329 B1 | 6/2004 | Rosenblum et al. |
| 6,838,260 B2 | 1/2005 | Gillies et al. |
| 6,969,517 B2 | 11/2005 | Gillies et al. |
| 6,992,174 B2 | 1/2006 | Gillies et al. |
| 7,067,110 B1 | 6/2006 | Gillies et al. |
| 7,091,321 B2 | 6/2006 | Gillies et al. |
| 7,141,651 B2 | 11/2006 | Gillies et al. |
| 7,148,321 B2 | 12/2006 | Gillies et al. |
| 7,169,904 B2 | 1/2007 | Gillies et al. |
| 7,186,804 B2 | 3/2007 | Gillies et al. |
| 7,211,253 B1 | 5/2007 | Way |
| 7,226,998 B2 | 6/2007 | Gillies et al. |
| 7,323,549 B2 | 1/2008 | Lauder et al. |
| 2001/0053539 A1 | 12/2001 | Lauffer et al. |
| 2002/0037558 A1 | 3/2002 | Lo et al. |
| 2002/0081664 A1 | 6/2002 | Lo et al. |
| 2002/0142374 A1 | 10/2002 | Gallo et al. |
| 2002/0146388 A1 | 10/2002 | Gillies |
| 2002/0147311 A1 | 10/2002 | Gillies et al. |
| 2002/0192222 A1 | 12/2002 | Blumberg et al. |
| 2002/0193570 A1 | 12/2002 | Gillies et al. |
| 2003/0003529 A1 | 1/2003 | Bayer |
| 2003/0012789 A1 | 1/2003 | Blumberg et al. |
| 2003/0044423 A1 | 3/2003 | Gillies et al. |
| 2003/0049227 A1 | 3/2003 | Gillies et al. |
| 2003/0105294 A1 | 6/2003 | Gillies et al. |
| 2003/0139365 A1 | 7/2003 | Lo et al. |
| 2003/0139575 A1 | 7/2003 | Gillies |
| 2003/0157054 A1 | 8/2003 | Gillies et al. |
| 2003/0166163 A1 | 9/2003 | Gillies |
| 2003/0166877 A1 | 9/2003 | Gillies et al. |
| 2004/0013640 A1 | 1/2004 | Zardi et al. |
| 2004/0033210 A1 | 2/2004 | Gillies |
| 2004/0043457 A1 | 3/2004 | Schumacher et al. |
| 2004/0053366 A1 | 3/2004 | Lo et al. |
| 2004/0072299 A1 | 4/2004 | Gillies et al. |
| 2004/0082039 A1 | 4/2004 | Gillies et al. |
| 2004/0180035 A1 | 9/2004 | Gillies et al. |
| 2004/0180386 A1 | 9/2004 | Carr et al. |
| 2004/0203100 A1 | 10/2004 | Gillies et al. |
| 2005/0042729 A1 | 2/2005 | Gillies et al. |
| 2005/0069521 A1 | 3/2005 | Gillies et al. |
| 2005/0137384 A1 | 6/2005 | Gillies et al. |
| 2005/0164352 A1 | 7/2005 | Lauder et al. |
| 2005/0192211 A1 | 9/2005 | Gillies et al. |
| 2005/0202021 A1 | 9/2005 | Gillies |
| 2005/0202538 A1 | 9/2005 | Gillies et al. |
| 2005/0244418 A1 | 11/2005 | Gillies et al. |
| 2005/0261229 A1 | 11/2005 | Gillies et al. |
| 2006/0025573 A1 | 2/2006 | Gillies et al. |
| 2006/0034836 A1 | 2/2006 | Gillies et al. |
| 2006/0141581 A1 | 6/2006 | Gillies et al. |
| 2006/0194952 A1 | 8/2006 | Gillies et al. |
| 2006/0228332 A1 | 10/2006 | Gillies et al. |
| 2006/0263856 A1 | 11/2006 | Gillies et al. |
| 2007/0036752 A1 | 2/2007 | Gillies et al. |
| 2007/0059282 A1 | 3/2007 | Gillies et al. |
| 2007/0104689 A1 | 5/2007 | Gillies et al. |
| 2007/0154453 A1 | 7/2007 | Webster et al. |
| 2007/0154473 A1 | 7/2007 | Super et al. |
| 2007/0178098 A1 | 8/2007 | Way et al. |
| 2007/0258944 A1 | 11/2007 | Gillies et al. |
| 2007/0287170 A1 | 12/2007 | Davis et al. |
| 2008/0025947 A1 | 1/2008 | Gillies et al. |

FOREIGN PATENT DOCUMENTS

| | | |
|---|---|---|
| EP | 0 294 703 A2 | 12/1988 |
| EP | 0 308 936 B1 | 3/1989 |
| EP | 0 314 317 B1 | 5/1989 |
| EP | 0 318 554 B1 | 6/1989 |
| EP | 0 326 120 B1 | 8/1989 |
| EP | 0 350 230 A2 | 1/1990 |
| EP | 0 375 562 B1 | 6/1990 |
| EP | 0 396 387 A2 | 11/1990 |
| EP | 0 439 095 A2 | 7/1991 |
| EP | 0 511 747 A1 | 11/1992 |
| EP | 0 519 596 A1 | 12/1992 |
| EP | 0 344 134 B1 | 1/1994 |
| EP | 0 601 043 B1 | 6/1994 |
| EP | 0 640 619 A1 | 3/1995 |
| EP | 0 668 351 | 8/1995 |
| EP | 0 668 353 A1 | 8/1995 |
| EP | 0 699 755 A2 | 3/1996 |
| EP | 0 428 596 B1 | 4/1996 |
| EP | 0 706 799 A2 | 4/1996 |
| EP | 0 428 267 B1 | 12/1996 |
| EP | 1 088 888 A1 | 4/2001 |
| GB | 2 188 638 | 10/1987 |
| WO | WO 86/01533 | 3/1986 |
| WO | WO 88/00052 | 1/1988 |
| WO | WO 88/09344 | 12/1988 |
| WO | WO 89/02922 | 4/1989 |
| WO | WO 89/09620 | 10/1989 |
| WO | WO 91/00360 | 1/1991 |
| WO | WO 91/04329 | 4/1991 |
| WO | WO 91/08298 | 6/1991 |
| WO | WO 91/13166 | 9/1991 |
| WO | WO 91/14438 | 10/1991 |
| WO | WO 92/02240 | 2/1992 |
| WO | WO 92/08495 | 5/1992 |
| WO | WO 92/08801 | 5/1992 |
| WO | WO 92/10755 | 6/1992 |
| WO | WO 92/16562 | 10/1992 |
| WO | WO 93/03157 | 2/1993 |
| WO | WO 94/24160 | 10/1994 |
| WO | WO 94/25055 | 11/1994 |
| WO | WO 94/25609 | 11/1994 |
| WO | WO 95/05468 | 2/1995 |
| WO | WO 95/21258 | 8/1995 |
| WO | WO 95/31483 | 11/1995 |
| WO | WO 96/04388 | 2/1996 |
| WO | WO 96/08570 | 3/1996 |
| WO | WO 96/18412 | 6/1996 |
| WO | WO 96/40792 | 12/1996 |
| WO | WO 97/00317 | 1/1997 |
| WO | WO 97/00319 | 1/1997 |
| WO | WO 97/24137 | 7/1997 |
| WO | WO 97/24440 | 7/1997 |
| WO | WO 97/30089 | 8/1997 |
| WO | WO 97/33617 | 9/1997 |
| WO | WO 97/33619 | 9/1997 |
| WO | WO 97/34631 | 9/1997 |
| WO | WO 97/43316 | 11/1997 |
| WO | WO 98/00127 | 1/1998 |
| WO | WO 98/24827 | 7/1998 |
| WO | WO 98/30706 | 7/1998 |
| WO | WO 98/46257 | 10/1998 |
| WO | WO 98/52976 | 11/1998 |
| WO | WO 98/59244 | 12/1998 |
| WO | WO 99/02709 | 1/1999 |
| WO | WO 99/002711 | 1/1999 |
| WO | WO 99/03887 | 1/1999 |
| WO | WO 99/29732 | 6/1999 |
| WO | WO 99/43713 | 9/1999 |
| WO | WO 99/52562 | 10/1999 |
| WO | WO 99/53958 | 10/1999 |
| WO | WO 99/66054 | 12/1999 |
| WO | WO 00/01822 | 1/2000 |
| WO | WO 00/11033 | 3/2000 |
| WO | WO 00/24893 | 5/2000 |

| | | |
|---|---|---|
| WO | WO 00/34317 | 6/2000 |
| WO | WO 00/40615 | 7/2000 |
| WO | WO 00/68376 | 11/2000 |
| WO | WO 00/69913 | 11/2000 |
| WO | WO 01/07081 | 2/2001 |
| WO | WO 01/10912 | 2/2001 |
| WO | WO 01/36489 | 5/2001 |
| WO | WO 01/58957 | 8/2001 |
| WO | WO 01/81405 | 11/2001 |
| WO | WO 02/02143 | 1/2002 |
| WO | WO 02/066514 | 8/2002 |
| WO | WO 02/072605 | 9/2002 |
| WO | WO 02/079232 | 10/2002 |
| WO | WO 02/079415 | 10/2002 |
| WO | WO 02/090566 | 11/2002 |
| WO | WO 03/015697 | 2/2003 |
| WO | WO 03/048334 | 6/2003 |
| WO | WO 03/077834 | 9/2003 |
| WO | WO 03/106484 A1 * | 12/2003 |

OTHER PUBLICATIONS

Adkins et al., (1998), "Edrecolomab (Monoclonal Antibody 17-1A)," *Drugs*, 56(4):619-626.

Anderson et al., (1980), "Characterization of the Fc Receptor for IgG on a Human Macrophage Cell Line U937," *J. Immunol.*, 125(6):2735-41.

Angal et al., (1993), "A Single Amino Acid Substitution Abolishes the Heterogeneity of Chimeric Mouse/Human (IgG4) Antibody," *Molecular Immunology*, 30(1):105-108.

Baici et al., (1980), "Kinetics of the Different Susceptibilities of the Four Human Immunoglobulin G Subclasses to Proteolysis by Human Lysosomal Elastase," *Scand. J. Immunol.*, 12(1):41-50.

Batra et al., (1993), "Insertion of Constant Region Domains of Human IgG1 into CD40-PE40 Increases Its Plasma Half-Life," *Molecular Immunology*, 30(4):379-386.

Batova et al., (1999), "The Ch14.18-GM-CSF Fusion Protein is Effective at Mediating Antibody-Dependent Cellular Cytotoxicity and Complement-Dependent Cytotoxicity in Vitro," *Clinical Cancer Research*, 5:4259-4263.

Becker et al., (1996), "An Antibody-Interleukin 2 Fusion Protein Overcomes Tumor Heterogeneity by Induction of a Cellular Immune Reponse," *Proc. Natl. Acad. Sci. USA*, 93:7826-7831.

Becker et al., (1996), "Eradication of Human Hepatic and Pulmonary Melanoma Metastases in SCID Mice by Anti-body-Interleukin 2 Fusion Proteins," *Proc. Natl. Acad. Sci. USA*, 93:2702-2707.

Becker et al., (1996), "Long-Lived and Transferable Tumor Immunity in Mice after Targeted Interleukin-2 Therapy," *J. Clin. Invest.*, 98(12):2801-2804.

Becker et al., (1996), "T Cell-Mediated Eradication of Murine Metastatic Melanoma Induced by Targeted Interleukin-2 Therapy," *J. Exp. Med.*, 183(50):2361-2366.

Beutler et al., (1988), "Tumor Necrosis, Cachexia, Shock, and Inflammation: A Common Mediator," *Annual Rev. Biochem.*, 57:505-518.

Bitonti et al., (2002), "Transepithelial Absorption of an Erythropoietin-Fc Fusion Protein After Delivery to the Central Airways," *Respiratory Drug Delivery*, 8:309-312.

Bitonti et al., (2004), Pulmonary Delivery of an Erythropoietin Fc Fusion Protein in Non-Human Primates Through an Immunoglobulin Transport Pathway, Proc. Natl. Acad. Sci. USA, 101(26):9763-9768.

Bjorn et al., (1985), "Evaluation of Monoclonal Antibodies for the Development of Breast Cancer Immunotoxins," *Cancer Research*, 45:1214-1221.

Boissel et al., (1993), "Erythropoietin Structure-Function Relationships: Mutant Proteins that Test a Model of Tertiary Structure," *The Journal of Biological Chemistry*, 268(21):15983-15993.

Bourgois et al., (1974), "Determination of the Primary Structure of a Mouse IgG2a Immunoglobulin: Amino-Acid Sequence of the Fc Fragment: Implications for the Evolution of Immunoglobulin Structure and Function," *Eur. J. Biochem.*, 43:423-35.

Boulianne et al., (1984), "Production of Functional Chimaeric Mouse/Human Antibody," *Nature*, 312:643-6.

Brambell et al., (1964), "A Theoretical Model of γ-Globulin Catabolism," *Nature*, 203:1352-55.

Brekke et al., (1994), "Human IgG Isotype-Specific Amino Acid Residues Affecting Complement-Mediated Cell Lysis and Phagocytosis," *Eur. J. Immunol.*, 24:2542-2547.

Briggs et al., (1974), "Hepatic Clearance of Intact and Desialylated Erythropoietin," *American Journal of Physiology*, 227(6):1385-1388.

Broudy et al., (1988), "Recombinant Human Erythropoietin: Purification and Analysis of Carbohydrate Linkage," *Arch. Biochem. Biophys.*, 265:329-36.

Bubenik et al., (1995), "Interleukin-2 Gene Therapy of Residual EL-4 Leukaemia Potentiates the Effect of the Cyclophosphamide Pretreatment," *J. Cancer Res. Clin. Oncol.*, 121:39-43.

Burgess et al., (1990), "Possible Dissociation of the Heparin-Binding and Mitogenic Activities of Heparin-Binding (Acidic Fibroblast) Growth Factor-1 from Its Receptor-Binding Activities by Site-Directed Mutagenesis of a Single Lysine Residue," *Journal of Cell Biology*, 111:2129-2138.

Canfield et al., (1991), "The Binding Affinity of Human IgG for its High Affinity Fc Receptor is Determined by Multiple Amino Acids in the CH2 Domain and is Modulated by the Hinge Region," *J. Exp. Med.*, 173(6):1483-1491.

Capon et al., (1989), "Designing CD4 Immunoadhesins for AIDS Therapy," *Nature*, 337:525-531.

Casadevall et al., (2002), "Pure Red-Cell Aplasia and Antierythropoietin Antibodies in Patients Treated with Recombinant Erythropoietin," *N. Engl. J. Med.*, 346(7):469-75.

Caton et al., (1986), "Structural and Functional Implications of a Restricted Antibody Response to a Defined Antigenic Region on the Influenza Virus Hemagglutinin," *The EMBO Journal*, 5(7):1577-1587.

Cazzola et al., (1998), "Red Blood Cell Precursor Mass as an Independent Determinant of Serum Erythropoientin Level," *Blood*, 91:2139-45.

Chan et al., (1992), "Mechanisms of IFN-γ Induction by Natural Killer Cell Stimulatory Factor (NKSF/IL-12). Role of Transcription and mRNA Stability in the Synergisitic Interaction Between NKSF and IL-2," *J. Immunol.*, 148:92-98.

Chapman et al., (1994), "Mapping Effector Functions of a Monoclonal Antibody to GD3 by Characterization of a Mouse-Human Chimeric Antibody," *Cancer Immuno. Immunother.*, 39:198-204.

Chappel et al., (1991), "Identification of the Fc Gamma Receptor Class I Binding Site In Human IgG Through Use of Recombinant IgG1/IgG2 Hybrid and Point-Mutated Antibodies," *Proc. Natl. Acad. Sci. USA*, 88(20):9036-40.

Chaudhary et al., (1988), "Selective Killing of HIV-Infected Cells by Recombinant Human CD4-*Pseudomonas* Exotoxin Hybrid Protein," *Nature*, 335:370-372.

Chaudhary et al., (1989), "A Recombinant Immunotoxin Consisting of Two Antibody Variable Domains Fused to *Pseudomonas* Exotoxin," *Nature*, 339:394-397.

Cheetham, (1998), "NMR Structure of Human Erythropoietin and a Comparison with its Receptor Bound Conformation," *Nat. Struct. Biol.*, 5:861-6.

Cheon et al., (1994), "High-Affinity Binding Sites for Related Fibroblast Growth Factor Ligands Reside Within Different Receptor Immunoglobulin-Like Domains," *Proc. Natl. Acad. Sci. USA*, 91: 989-993.

Cirulli et al., (1998), "KSA Antigen Ep-CAM Mediates Cell-Cell Adhesion of Pancreatic Epithelial Cells: Morphoregulatory Roles in Pancreatic Islet Development," *J. Cell Biol.*, 140:1519-34.

Cohen et al., (1998), "An Artificial Cell-Cycle Inhibitor Isolated from a Combinatorial Library," *Proc. Natl. Acad. Sci. USA*, 95:14272-7.

Cole et al., (1997), "Human IgG2 Variants of Chimeric Anti-CD3 Are Nonmitogenic to T Cells," *Journal of Immunology*, 159:3613-3621.

Congote et al., (1984), "The Erthrotropins, New Erythroid Cell Stimulate Factors Extracted From Human and Bovine Fetal Tissues," Abstract 364, "Proceedings 7th Intl. Congress of Endocrinology," Quebec City, Quebec, Jul. 1-7, 1984.

Congote, (1983), "Isolation of Two Biologically Active Peptides, Erythrotropin I and Erythrotropin II from Fetal Calf Intestine," *Biochem. Biophys. Res. Commun.*, 115(2):477-83.

Congote, (1984), "Extraction from Fetal Bovine Serum of Erythrotropin, an Erythroid Cell-Stimulating Factor," *Anal. Biochem.*, 140:428-33.

Connor et al., (2004), "Ex vivo Evaluation of Anti-EpCAM Immunocytokine huKS-IL2 in Ovarian Cancer," *J. Immunotherapy*, 27:211-219.

Cruse et al., (eds.), (1995), *Illustrated Dictionary of Immunology*, pp. 156-158, CRC Press, NY.

Darling et al., (2002), "Glycosylation of Erythropoietin Affects Receptor Binding Kinetics: Role of Electrostatic Interactions," *Biochemistry*, 41:14524-14531.

Davis et al., (2003), "Immunocytokines: Amplification of Anti-Cancer Immunity," *Cancer Immunol. Immunother.*, 52:297-308.

de la Salle et al., (1996), "FcγR on Human Dendritic Cells," *Human IgG Receptors*, pp. 39-55, van de Winkel et al. (eds.), R.G. Landes Co.

Delorme et al., (1992), "Role of Glycosylation on the Secretion and Biological Activity of Erythropoietin," *Biochemistry*, 31:9871-6.

Dolman et al., (1998), "Suppression of Human Prostate Carcinoma Metastases in Severe Combined Immunodeficient Mice by Interleukin 2 Immunocytokine Therapy," *Clin. Cancer Research.*, 4(10):2551-2557.

Dorai et al., (1991), "Aglycosylated Chimeric Mouse/Human IgGl Antibody Retains Some Effector Function," *Hybridoma*, 10(2):211-217.

Dorai et al., (1992), "Role of Inter-Heavy and Light Chain Disulfide Bonds in the Effector Functions of Human IgGl," *Molecular Immunology*, 29(12):1487-1491.

Dube et al., (1988), "Glycosylation at Specific Sites of Erthropoietin is Essential for Biosynthesis, Secretion, and Biological Function," *J. Biol. Chem.*, 263:17516-21.

Duncan et al., (1988), "The Binding Site for Clq on IgG," *Nature* 332:738-740.

Egrie et al., (2001), "Development and Characterization of Novel Erythropoiesis Stimulating Protein (NESP)," *Nephrol. Dial. Transplant.*, 16(Supp 3):3-13.

Elliott et al., (1996), "Fine-Structure Epitope Maping of Antierythropoietin Monoclonal Antibodies Reveals a Model of Recombinant Human Erythropoietin Structure," *Blood*, 87(7)2702-2713.

Elliott et al., (1997), "Mapping of the Active Site of Recombinant Human Erythropoietin," *Blood*, 89(2):493-502.

Ellison et al., (1982), "The Nucleotide Sequence of a Human Immunoglobulin C $\gamma_1$ Gene," *Nucleic Acids Res.*, 10:4071-9.

Fell et al., (1991), "Genetic Construction and Characterization of a Fusion Protein Consisting of a Chimeric F(ab') with Specificity for Carcinomas and Human IL-2," *J. Immunology*, 146(7):2446-2452.

Fell et al., (1992), "Chimeric L6 Anti-Tumor Anitbody: Genomic Construction, Expression, and Characterization of the Antigen Binding Site," *J. Biological Chemistry*, 267:15552-15558.

Fibi et al., (1995), "N- and O-Glycosylation Muteins of Recombinant Human Erythropoietin Secreted From BHK-21 Cells," *Blood*, 85(5):1229-1236.

Frost et al., (1997), "A Phase I/IB Trial of Murine Monoclonal Anti-GD2 Antibody 14.G2a Plus Interleukin-2 in Children with Refractory Neuroblastoma," *Cancer*, 80(2):317-333.

Fu et al., (1993), "The Sheep Erythropoietin Gene: Molecular Cloning and Effect of Hemorrhage on Plasma Erythropoietin and Renal/Liver Messenger RNA in Adult Sheep," *Mol. Cell. Endocrinol.*, 93:107-16.

Gan et al., (1999), "Specific Enzyme-Linked Immunosorbent Assays for Quantitation of Antibody-Cytokine Fusion Proteins," *Clinical and Diagnostic Laboratory Immunology*, 6(2):236-42.

Gasson et al., (1984), "Purified Human Granulocyte Macrophage Colony-Stimulating Factor: Direct Action on Neutrophils," *Science*, 226:1339-1342.

Ghetie et al., (1997), "FcRn: The MHC Class I-Related Receptor that is More Than an IgG Transporter," *Immunology Today*, 18(12):592-598.

Gillies et al., (1989), "Expression of Human Anti-Tetanus Toxoid Antibody in Transfected Murine Myeloma Cells," *Bio/Technology*, 7:799-804.

Gillies et al., (1989), "High-Level Expression of Chimeric Antibodies Using Adapted cDNA Variable Region Cassettes," *J. Immunol. Methods*, 125: 191-202.

Gillies et al., (1990), "Antigen Binding and Biological Activities of Engineered Mutant Chimeric Antibodies with Human Tumor Specificities," *Hum. Antibod. Hybridomas*, 1(1):47-54.

Gillies et al., (1991), "Expression of Genetically Engineered Immunoconjugates of Lymphotoxin and a Chimeric Anti-Ganglioside GD2 Antibody," *Hybridoma.*, 10(3):347-56.

Gillies et al., (1991), "Targeting Human Cytotoxic T Lymphocytes to Kill Heterologous Epidermal Growth Factor Receptor-Bearing Tumor Cells: Tumor-Infiltrating Lympnocyte/Hormone Receptor/Recombinant Antibody," *J. Immunology*, 146(3):1067-1071.

Gillies et al., (1992), "Antibody-Targeted Interleukin 2 Stimulates T-Cell Killing of Autologous Tumor Cells," *Proc. Natl. Acad. Sci. USA*, 89:1428-1432.

Gillies et al., (1993), "Biological Activity and In Vivo Clearance of Antitumor Antibody/Cytokine Fusion Proteins," *Bioconjugate Chem.*, 4(3):230-235.

Gillies et al., (1998), "Antibody-IL-12 Fusion Proteins are Effective in SCID Mouse Models of Prostate and Colon Carcinoma Metastases," *J. Immunology*, 160:6195-6203.

Gillies et al., (1999), "Improving the Efficacy of Antibody-Interleukin 2 Fusion Proteins by Reducing Their Interaction with Fc Receptors," *Cancer Research*, 59:2159-2166.

Gillies et al., (2002), "Bi-Functional Cytokine Fusion Proteins for Gene Therapy and Antibody-Targeted Treatment of Cancer," *Cancer Immunol. Immunother.*, 51(8):449-60.

Gillies et al., (2002), "Improved Circulating Half-Life and Efficacy of an Antibody-Interleukin 2 Immunocytokine Based on Reduced Intracellular Proteolysis," *Clin. Cancer Research*, 8(1):210-216.

Goeddell et al., (1986), "Tumor Necrosis Factors: Gene Structure and Biological Activities," *Cold Spring Harb. Symp. Quant. Biol.*, 51:597-609.

Goldwasser et al., (1971), "Purification of Erythropoietin," *Proc. Natl. Acad. Sci. USA*, 68:697-8.

Goldwasser et al., (1975), "Erythropoeitin: Assay and Study of its Mode of Action," *Methods Enzymol.*, 37(PtB):109-21.

Gren et al., (1983), "A New Type of Leukocytic Interferon," English Translation of *Dokl. Akad. Nauk. SSSR.*, 269(4):986-990.

Grimaldi et al., (1989), "The t(5;14) Chromosomal Translocation in a Case of Acute Lymphocytic Leukemia Joins the Interleukin-3 Gene to the Immunoglobulin Heavy Chain Gene," *Blood*, 73(8):2081-2085.

Gurewich et al., (1988), "Characterization of the Intrinsic Fibrinolytic Properties of Pro-Urokinase Through a Study of Plasmin-Resistant Mutant Forms Produced by Site-Specific Mutagenesis of Lysine," *J. Clin. Invest.*, 82:1956-1962.

Guyre et al., (1997), "Increased Potency of Fc-Receptor-Targeted Antigens," *Cancer Immunol. Immunother.*, 45:146-148.

Halin et al., (2002), "Enhancement of the Antitumor Activity of Interleukin-12 by Targeted Delivery to Neovasculature," *Nature Biotechnology*, 20:264-269.

Hammerling et al., (1996), "In Vitro Bioassay for Human Erythropoietin Based on Proliferative Stimulation of an Erythroid Cell Line and Analysis of Carbohydrate-Dependent Microheterogeneity," *Journal of Pharmaceutical and Biomedical Analysis*, 14:1455-1469.

Handgretinger et al., (1995), "A Phase I Study of Human/Mouse Chimeric Anti-Ganglioside GD2 Antibody ch14.18 in Patients with Neuroblastoma," *European J. Cancer*, 31A(2):261-267.

Hank et al., (1996), "Activation of Human Effector Cells by a Tumor Reactive Recombinant Anti-Ganglioside GD2 Interleukin-2 Fusion Protein (ch14.18-IL2)," *Clin Cancer Research*, 2(12):1951-1959.

Hank et al., (2003), "Determination of Peak Serum Levels and Immune Response to the Humanized Anti-Ganglioside Antibody-Interleukin-2 Immunocytokine," in *Methods in Molecular Medicine, 85: Novel Anticancer Drug Protocols*, Buolamwini et al., (eds.), pp. 123-131, Humana Press Inc., Totowana, NJ.

Haraguchi, (1994), "Isolation of GD3 Synthase Gene by Expression Cloning of GM3 α-2,8-sialyltransferase cDNA Using Anti-GD2 Monoclonal Antibody," *Proc. Natl. Acad. Sci. USA*, 91(22):10455-10459.

Harris et al., (1993), "Therapeutic Antibodies—the Coming of Age," *Trends in Biotechnology*, 11:42-44.

Harris, (1995), "Processing of C-Terminal Lysine and Arginine Residues of Proteins Isolateed from Mammalian Cell Culture," *J. Chromatography A*, 705:129-134.

Harvill et al., (1995), "An IgG3-IL2 Fusion Protein Activates Complement, Binds FcγRI, Generates LAK Activity and Shows Enhanced Binding to the High Affinity IL-2R," *Immunotechnology*, 1:95-105.

Harvill et al., (1996), "In Vivo Properties of an IgG3-IL-2 Fusion Protein: A General Strategy for Immune Potentiation," *J. Immunology*, 157(7):3165-3170.

He et al., (1998), "Humanization and Pharmacokinetics of a Monoclonal Antibody with Specificity for Both E- and P-Selectin," *J. Immunology*, 160:1029-1035.

Hellstrom et al., (1986), "Antitumor Effects of L6, an IgG2a Antibody that Reacts with Most Human Carcinomas," *Proc. Natl. Acad. Sci. USA*, 83:7059-7063.

Henkart, (1985), "Mechanism of Lymphocyte-Mediated Cytotoxicity," *Ann. Rev. Immunol.*, 3:31-58.

Herrmann et al., (1989), "Hematopoietic Responses With Advanced Malignancy Treated With Recombinant Human Granulocyte-Macrophage Colony-Stimulating Factor," *Journal of Clinical Oncology*, 7(2):159-167.

Hezareh et al., (2001), "Effector Function Activities of a Panel of Mutants of a Broadly Neutralizing Antibody against Human Immunodeficiency Virus Type I," *J. Virology*, 75(24):12161-12168.

Holden et al., (2001), "Augmentation of Antitumor Activity of an Antibody-Interleukin 2 Immunocytokine with Chemotherapeutic Agents," *Clinical Cancer Research*, 7:286202869.

Holden et al., (2001), "Augmentation of Anti-Tumor Activity of KS-IL2 Immunocytokine with Chemotherapeutic Agents," *Proceedings of the American Association for Cancer Research*, 42:683, Abstract No. 3675 (XP-002195344).

Hoogenboom et al., (1991), "Construction and Expression of Antibody-Tumor Necrosis Factor Fusion Proteins," *Molecular Immunology*, 28(9):1027-1037.

Hoogenboom et al:, (1991), "Targeting of Tumor Necrosis Factor to Tumor Cells Secretion by Myeloma Cells of a Genetically Engineered Antibody-Tumor Necrosis Factor Hybrid Molecule," *Biochim. Biophys. Acta*, 1096(4):345-354 (Abstract).

Hornick et al., (1999), "Pretreatment with a Monoclonal Antibody/Interleukin-2 Fusion Protein Directed Against DNA Enhances the Delivery of Therapeutic Molecules to Solid Tumors," *Clin. Cancer Research*, 5:51-60.

Huck et al., (1986), "Sequence of Human Immunoglobulin Gamma 3 Heavy Chain Constant Region Gene: Comparison With the Other Human Cγ genes," *Nucleic Acids Research*, 14(4):1779-1789.

Hulett et al., (1994), "Molecular Basis of Fc Receptor Function," *Adv. Immunol.*, 57:1127.

Hurn et al., (1980), "Production of Reagent Antibodies," *Methods in Enzymology*, 70: 104-142.

Huston et al., (1998), "Protein Engineering of Antibody Binding Sites: Recovery of Specific Activity in an Anti-Digoxin Single-Chain Fv Analogue Produced In *Escherichia coli*," *Proc. Natl. Acad. Sci. USA*, 85:5879-5883.

Idusogie et al., (2000), "Mapping of the C1q Binding Site on Rituxan, a Chimeric Antibody with a Human IgG1 Fc," *J. Immunology*, 164(8):4178-4184.

Imboden et al., (2001), "The Level of MHC Class 1 Expression on Murine Adenocarcinoma Can Change the Antitumor Effector Mechanism of Immunocytokine Therapy," *Cancer Research*, 61(4):1500-7.

Isaacs et al., (1998), "Therapy with Monoclonal Antibodies. II. The Contribution of Fcγ Receptor Binding and the Influence of CH1 and CH3 Domains on In Vivo Effector Funcion," *J. Immunol.*, 161:3862-3869.

Isenman et al., (1975), "The Structure and Function of Immunoglobulin Domains: II. The Importance of Interchain Disulfide Bonds and the Possible Role of Molecular Flexibility in the Interaction between Immunoglobulin G and Complement," *J. Immunology*, 114(6):1726-1729.

Jacobs et al., (1985), "Isolation and Characterization of Genomic And cDNA Clones of Human Erythropoietin," *Nature*, 313:806-10.

Jeffries et al., (1990), "Molcular Definition of Interaction Sites on Human IgG for Fc Receptors huFcγR," *Mol. Immunol.*, 27(12):1237-1240.

Jones et al., (1986), "Replacing the Complementarity-Determining Regions in a Human Antibody with Those from a Mouse," *Nature*, 321:522-525.

Jones et al., (2004), "The Development of a Modified Human IFN-α2b Linked to the Fc Portion of Human IgG1 as a Novel Potential Therapeutic for the Treatment of Hepatitis C Virus Infection," *J. Interferon and Cytokine Res.*, 24:560-572.

Jung et al., (1986), "Activation of Human Peripheral Blood Mononuclear Cells by Anti-T3: Killing of Tumor Target Cells Coated with Anti-Target-Anti-T3 Conjugates," *Proc. Natl. Acad. Sci. USA*, 83:4479-4483.

Junghans et al., (1996), "The Protection of IgG Catabolism is the B2-Microglobulin-Containing Neonatal Intestinal Transport Receptor," *Proc. Natl. Acad. Sci. USA*, 93(11):5512-5516.

Kappel et al., (1992), "Regulating Gene Expression in Transgenic Animals," *Current Opinion in Biotechnology*, 3:548-553.

Karpovsky et al., (1984), "Production of Target-Specific Effector Cells using Hetero-Cross Linked Aggregate Contianing Anti-Target Cell and AntiFcγ Receptor Antibodies," *Journal of Experimental Medicine*, 1609(6):1686-1701.

Kato et al., (1997), "Mechanism for the Nonlinear Pharmacokinetics of Erythropoietin in Rats," *The Journal of Pharmacology and Experimental Therapeutics*, 283:520-527.

Kato et al., (1998), "Pharmacokinetics of Erythopoietin in Genetically Anemic Mice," *Drug Metabolism and Disposition*, 26(2):126-131.

Kendra et al., (1999), "Pharmacokinetics and Stability of the ch14.18-Interleukin-2 Fusion Protein in Mice," *Cancer Immunol. Immunother.*, 48:219-229.

Kim et al., (1999), "Cytokine Molecular Adjuvants Modulate Immune Responses Induced by DNA Vaccine Constructs for HIV-1 and SIV," *Journal of Interferon and Cytokine Research*, 19:77-84.

King et al., (2004), "Phase I Clinical Trial of the Immunocytokine EMD 273063 in Melanoma Patients," *J. Clin. Oncol.*, 22(22):4463-73.

Kitamura et al., (1989), "Establishment and Characterization of a Unique Human Cell Line that Proliferates Dependently on GM-CSF, IL-3, or Erythropoietin," *Journal of Cellular Physiology*, 140:323-334.

Ko et al., (2004), "Safety, Pharmacokinetics, and Biological Pharmacodynamics of the Immunocytokine EMD 273066 (huKS-IL2)," *J. Immunotherapy*, 27:232-239.

Kranz, et al., (1984), "Attachment of an Anti-Receptor Antibody to Non-Target Cells Renders Them Susceptible to Lysis by a Clone of Cytotoxic T Lymphocytes," *Proc. Natl. Acad. SCi. USA*, 81:7922-7926.

Kurtz, (1982), "A New Candidate for the Regulation of Erythropoiesis. Insulin-Like Growth Factor I," *FEBLAL.*, 149(1):105-8.

Kushner et al., (2001), "Phase II Trial of the Anti-GD2 Monoclonal Antibody 3F8 and Granulocyte-Macrophage Colony-Stimulating Factor for Neuroblastoma," *J. Clinical Oncology*, 19(22):4189-94.

Lai et al., (1986), "Structural Characterization of Human Erythropoietin," *J. Biol. Chem.*, 261:3116-21.

Lanza et al., (1993), "Active Immunity against the CD4 Receptor by Using an Antibody Antigenized with Residues 41-55 of the First Extracellular Domain," *Proc. Natl. Acad. Sci. USA*, 90:11683-7.

Lazar et al., (1988), "Transforming Growth Factor α: Mutation of Aspartic Acid 47 and Leucine 48 Results in Different Biological Activities," Molecular *and Cellular Biology*, 8(3):1247-1252.

LeBerthon et al., (1991), "Enhanced Tumor Uptake of Macromolecules Induced by a Novel Vasoactive Interleukin 2 Immunoconjugate," *Cancer Research*, 51:2694-2698.

Lin et al., (1985), "Cloning and Expression of the Human Erythropoietin Gene," *Proc. Natl. Acad. Sci. USA*, 82:7580-4.

Lin et al., (1986), "Monkey Erythropoietin Gene: Cloning, Expression and Comparison with the Human Erythropoietin Gene," *Gene*, 44:201-9.

Linsley et al., (1991), "CTLA-4 is a Second Receptor for B Cell Activation Antigen B7," *J. Exp. Med.*, 174(3):561-569.

Liu et al., (1985), "Heteroantibody Duplexes Target Cells for Lysis by Cytotoxic T Lymphocytes," *Proc. Natl. Acad. Sci. USA*, 82:8648-8652.

Liu et al., (1988), "Hormone Conjugated with Antibody to CD3 Mediates Cytotoxic T Cell Lysis of Human Melanoma Cells," *Science*, 239:395-398.

Lo et al., (1992), "Expression and Secretion of an Assembled Tetrameric CH2-Deleted Antibody in *E. coli.*," *Hum. Antibod. Hybridomas*, 3:123-128.

Lo et al., (1998), "High Level Expression and Secretion of Fc-X Fusion Proteins in Mammalian Cells," *Protein Engineering*, 11(6):495-500.

Lo et al., (2005), "Engineering a Pharmacologically Superior Form of Leptin for the Treatment of Obesity," *Protein Engineering, Design & Selection*, 18(1):1-10.

Locatelli et al., (2001), "Darbepoetin Alfa Amgen," *Current Opinion in Investigational Drugs*, 2:1097-1104.

Lode et al., (1997), "Targeted Interleukin-2 Therapy for Spontaneous Neuroblastoma Metastases to Bone Marrow," *J. Natl. Cancer Inst.*, 89(21):1586-94.

Lode et al., (1998), "Immunocytokines: A Promising Approach to Cancer Immunotherapy," *Pharmacol. Ther.*, 80(3):277-292.

Lode et al., (1998), "Natural Killer Cell-Mediated Eradication of Neuroblastoma Metastases to Bone Marrow by Targeted Interleukin-2 Therapy," *Blood*, 91(5):1706-1715.

Lode et al., (1999), "Synergy Between an Antiangiogenic Integrin $\alpha_v$ Antagonist and an Antibody-Cytokine Fusion Protein Eradicates Spontaneous Tumor Metastases," *Proc. Natl. Acad. Sci. USA*, 96:1591-1596.

Lode et al., (1999), "Tumor-Targeted IL-2 Amplifies T Cell-Mediates Immune Response Induced by Gene Therapy with Single-Chain IL-12," *Proc. Natl. Acad. Sci. USA*, 96:8591-8596.

Lode et al., (2000), "Amplification of T Cell Mediated Immune Responses by Antibody-Cytokine Fusion Proteins," *Immunological Investigations*, 29(2):117-120.

Lode et al., (2000), "Melanoma Immunotherapy by Targeted IL-2 Depends on CD4(+) T-Cell Help Mediated by CD40/CD40L Interaction," *J. Clin. Invest.*, 105(11):1623-30.

Lode et al., (2000), "What To Do With Targeted IL-2," *Drugs of Today*, 36(5):321-336.

Macdougall et al., (1999), "Pharmacokinetics of Novel Erythropoiesis Stimulating Protein Compared with Epoetin Alfa in Dialysis Patients," *J. Am. Soc. Nephrol.*, 10:2392-5.

Macdougall, (2002), "Optimizing the Use of Erythropoietic Agents—Pharmacokinetic and Pharmacodynamic Considerations," *Nephrol. Dial. Transplant.*, 17(Supp 5):66-70.

MacLean et al., (1996), "Enhancing the Effect of Theratope STn-KLH Cancer Vaccine in Patients with Metastatic Breast Cancer by Pretreatment with Low-Dose Intravenous Cyclophosphamide," *J. Immunother.*, 19(4):309-316.

Maloney et al., (1994), "Phase I Clinical Trial Using Escalating Single-Dose Infusion of Chimeric Anti-CD20 Monoclonal Antibody (IDEC-C2B8) in Patients with Recurrent B-Cell Lymphoma," *Blood*, 84(8):2457-2466.

Mark et al., (1992), "Expression and Characterization of Hepatocyte Growth Factor Receptor-IgG Fusion Proteins," *Journal of Biological Chemistry*, 267(36):26166-26171.

Mariani et al., (1997), "Tumor Targeting Potential of the Monoclonal Antibody BC-1 against Oncofetal Fibronectin in Nude Mice Bearing Human Tumor Implants," *Cancer*, 80:2378-84.

Martin et al., (2001), "Crystal Structure at 2.8 Å of an FcRn/Heterodimeric Fc Complex: Mechanism of pH-Dependent Binding," *Mol. Cell.*, 7(4):867-77.

Mateo et al., (2000), "Removal of Amphipathic Epitopes from Genetically Engineered Antibodies: Production of Modified Immunoglobulins with Reduced Immunogenicity," *Hybridoma*, 19(6):463-471.

McDonald, (1986), "Cloning, Sequencing, and Evolutionary Analysis of the Mouse Erythropoietin gene," *Mol. Cell. Biol.*, 6:842-8.

McGonigle et al., (1984), "Erythropoietin Deficiency and Inhibition of Erythropoiesis in Renal Insufficiency," *Kidney Int.*, 25(2):437-44.

McMahan et al., (1991), "A Novel IL-1 Receptor, Cloned From B-Cells by Mammalian Expression is Expressed in Many Cell Types," *EMBO J.*, 10:2821-32.

McMahon et al., (1990), "Pharmacokinetics and Effects of Recombinant Human Erythropoietin after Intravenous and Subcutaneous Injections in Healthy Volunteers," *Blood*, 76:1718-22.

Medesan et al., (1997), "Delineation of the Amino Acid Residues Involved in Transcytosis and Catabolism of Mouse IgG1," *J. Immunology*, 158(5):2211-2217.

Menard et al., (1983), "Generation of Monoclonal Antibodies Reacting with Normal and Cancer Cells of Human Breast," *Cancer Res.*, 43:1295-300.

Metelitsa et al., (2002), "Antidisialoganglioside/Granulocyte Macrophage-Colony-Stimulating Factor Fusion Protein Facilitates Neutrophil Anitbody-Dependent Cellular Cytotoxicity and Depends on FcγR11 (CD32) and Mac-11 (CD11b/CD18) for Enhanced Effector Cell Adhesion and Azurophil Granule Exocytosis," *Blood*, 99(11):4166-73.

Miyake et al., (1977), "Purification of Human Erythropoietin," *J. Biol. Chem.*, 252:5558-64.

Miyake et al., (1988), "Synthesis of Recombinant Human Single-Chain Urokinase-Type Plasminogen Activator Variants Resistant to Plasmin and Thrombin," *J. Biochem.*, 104-:643-647.

Morrison et al., (1990), "Chimeric Human Antibody Molecules: Mouse Antigen-Binding Domains with Human Constant Region Domains," *Proc. Natl. Acad. Sci. USA*, 81:6851-5.

Mueller et al., (1990), "Enhancement of Antibody-Dependent Cytotoxicity With A Chimeric Anti-GD2 Anitbody," *J. Immunology*, 144(4):1382-1386.

Mueller et al., (1990), "Serum Half-Life and Tumor Localization of a Chimeric Antibody Deleted of the CH2 Domain and Directed Against the Disialoganglioside GD2," *Proc. Natl. Acad. Sci. USA*, 87:5702-5705.

Mueller et al., (1997), "Humanized Porcine VCAM-Specific Monoclonal Antibodies with Chimeric IgG2/G4 Constant Regions Block Human Leukocyte Binding to Porcine Endolethial Cells," *Molecular Immunology*, 34(6):441-452.

Murphy et al., (1986), "Genetic Construction, Expression, Melanoma-Selective Cytotoxicity of a Diphtheria Toxin-Related α-Melanocyte-Stimulating Hormone Fusion Protein," *Proc. Natl. Acad. Sci. USA*, 83:8258-8262.

Murphy, (1988), "Diphtheria-Related Peptide Hormone Gene Fusions: A Molecular Gene Approach to Chimeric Toxin Development," in *Immunotoxins*, pp. 123-140, Frankel (ed.), Kluwer Acad. Pub.

Nagao et al., (1992), "Nucleotide Sequence of Rat Erythropoietin," *Biochim. Biophys. Acta*, 1171(1):99-102.

Naughton et al., (1983), "Evidence for an Erythropoietin-Stimulating Factor in Patients with Renal and Hepatic Disease," *Acta. Haemat.*, 69:171-9.

Naramura et al., (1993), "Therapeutic Potential of Chimeric and Murine Anti-(Epidermal Growth Factor Receptor) Antibodies in a Metastasis Model for Human Melanoma," *Cancer Immuno. Immunother.*, 37:343-349.

Naramura et al., (1994), "Mechanisms of Cellular Cytotoxicity Mediated by a Recombinant Antibody-IL2 Fusion Protein Against Human Melanoma Cells," *Immunology Letters*, 39:91-99.

Nastala et al., (1994), "Recombinant IL-12 Administration Induces Tumor Regression in Association with IFN-γ Production," *J. Immunol.*, 153:1697-706.

Neal et al., (2003), "NXS2 Murine Neuroblastomas Express Increased Levels of MHC Class I Antigens upon Recurrence Following NK-Dependent Immunotherapy," *Cancer Immunol. Immunother.*, 53:41-52.

Neal et al., (2004), "Enhanced Activity of Hu14.18-IL2 Immunocytokine against Murine NXS2 Neuroblastoma when Combined with Interleukin-2 Therapy," *Clin. Cancer. Res.*, 10:4839-4847.

Nedwin et al., (1985), "Human Lymphotoxin and Tumor Necrosis Factor Genes: Structure, Homology and Chromosomal Localization," *Nucleic Acids Research*, 13(17):6361-6373.

Nelles et al., (1987), "Characterization of Recombinant Human Single Chain Urokinase-Type Plaminogen Activtor Mutants Produced by Site-Specific Mutagenesis of Lysine 158," *J. Biol. Chem.*, 262(12):5682-5689.

Neuberger et al., (1984), "Recombinant Antibodies Possessing Novel Effector Functions," *Nature*, 312:604-608.

Ngo et al., (1994), "Computational Complexity, Protein Structure Prediction, and the Levinthal Paradox," in *The Protein Folding Problem and Tertiary Structure Prediction*, Merz et al. (eds.), pp. 433-440 and 492-495, Birkhauser, Boston, MA.

Niethammer et al., (2001) "Targeted Interleukin 2 Therapy Enhances Protective Immunity Induced by an Autologous Oral DNA Vaccine against Murine Melanoma," *Cancer Research*, 61(16):6178-84.

Nimtz et al., (1993), "Structures of Sialylated Oligosaccharides of Human Erythropoietin Expressed in Recombinant BHK-21 Cells," *Eur. J. Biochem.*, 213:39-56.

Orlandi et al., (1989), "Cloning Immunoglobulin Variable Domains for Expression by the Polymerase Chain Reaction," *Proc. Natl. Acad. Sci. USA*, 86:3833-7.

Pancook et al., (1996), "Eradication of Established Hepatic Human Neuroblastoma Metastates in Mice with Severe Combined Immunodeficiency by Antibody-Targeted Interleukin-2," *Cancer Immunol. Immunother.*, 42(2):88-92.

Park et al., (2000), "Efficiency of *Promoter* and Cell Line in High-Level Expression of Erythropoietin," *Biotechnol. Appl. Biochem.*, 32:167-172.

Pastan et al., (1989), "*Pseudomonas* Exotoxin: Chimeric Toxins," *Journal of Biological Chemistry*, 264(26):15157-15160.

Paul et al., (1988), "Lymphotoxin," *Ann. Rev. Immunol.*, 6:407-438.

Pavlović-Kentera et al., (1980), "Effects of Prostaglandin Synthetase Inhibitors, Salt Overload and Renomedullary Dissection on the Hypoxia Stimulated Erythropoietin Production in Rats," *Exp. Hematol.*, 8(Supp. 8):239-92.

Pedley et al., (1999), "Enhancement of Antibody-Directed Enzyme Prodrug Therapy in Colorectal Xenografts by an Antivascular Agent," *Cancer. Res.*, 59:3998-4003.

Perez et al., (1986), "Specific Targeting of Human Peripheral Blood T Cells By Heteroaggregates Containing Anti-T3 Crosslinked to Anti-Target Cell Anitbodies," *J. Exp. Med.*, 163-166-178.

Perez et al., (1989), "Isolation and Characterization of a cDNA Encoding the KS1/4 Epithelial Carcinoma Marker,"*J. Immunology*, 142(10):3662-3667.

Poon et al., (1995), "Structure and Function of Several Anti-Dansyl Chimeric Antibodies Formed by Domain Interchanges Between Human IgM and Mouse IgG2b," *J. Biol. Chem.*, 270:8571-7.

Queen et al., (1989), "A Humanized Antibody that Binds to the Interleukin 2 Receptor," *Proc. Natl. Acad. Sci. USA*, 86:10029-33.

Reisfeld et al., (1994), "Potential of Genetically Engineered Anti-Ganglioside GD2 Antibodies for Cancer Immunotherapy," *Prog. Brian Res.*, 101:201-212.

Reisfeld et al., (1996), "Antibody-Interleukin 2 Fusion Proteins: A New Approach to Cancer Therapy," *J. Clin. Lab. Anal.*, 10:160-166.

Reisfeld et al., (1996), "Involvement of B Lymphocytes in the Growth Inhibition of Human Pulmonary Melanoma Metastates in Athymic *nu/nu* Mice by an Antibody-Lymphotoxin Fusion Protein," *Cancer Research*, 56(8):1707-1712.

Reisfeld et al., (1996), "Recombinant Antibody Fusion Protein for Cancer Immunotherapy," *Current Topics in Microbiology and Immunology*, 213:27-53.

Reisfeld et al., (1997), "Immunocytokines: A New Approach to Immunotherapy of Melanoma," *Melanoma Research*, 7(Supp2):S99-S106.

Resegotti et al., (1981), "Treatment of Aplastic Anaemia with Methenolone, Stanozolol and Nandrolone. A Report of 130 Cases," *Pan. Med.*, 23:243-8.

Reichmann et al., (1988), "Reshaping Human Antibodies for Therapy," *Nature*, 332:323-7.

Riethmuller et al., (1994), "Randomised Trial of Monoclonal Antibody for Adjuvant THerapy of Resected Dukes' C Colorectal Carcinoma," *The Lancet*, 343:1177-1183.

Robinson et al., (1998), "Optimizing the Stability of Single-Chain Proteins by Linker Length and Composition Mutagenesis," *Proc. Natl. Acad. Sci. USA*, 95:5929-34.

Rosenberg, (1988), "Immunotherapy of Cancer Using Interleukin 2: Current Status and Future Prospects," *Immunology Today*, 9(2):58-62.

Rothmann et al., (1982), "Erythropoietin-Dependent Erythrocytosis associated with Hepatic Angiosarcoma," *J. Surg. Oncol.*, 20:105-8.

Ruehlmann et al., (2001), "MIG (CXCL9) Chemokine Gene Therapy Combines with Antibody-Cytokine Fusion Protein to Suppress Growth and Dissemination of Murine Colon Carcinoma," *Cancer Research*, 61(23):8498-503.

Sabzevari et al., (1994), "A Recombinant Antibody-Interleukin 2 Fusion Protein Suppresses Growth of Hepatic Human Severe Combined Immunodeficiency Mice," *Proc. Natl. Acad. Sci. USA*, 91(20):9626-30.

Sakano et al., (1980), "Two Types of Somatic Recombination are Necessary for the Generation of Complete Immunoglobin Heavy-Chain Genes," *Nature*, 286:676-683.

Saleh et al., (1992), "Phase I Trial of the Chimeric Anti-GD2 Monoclonal Antibody ch14.18 in Patients With Malignant Melanoma," *Hum. Antiob. Hybridomas*, 3:19-24.

Santon et al., (1986), "Effects of Epidermal Growth Factor Receptor Concentration on Tumorigenicity of A431 Cells in Nude Mice," *Cancer Research*, 46:4701-4705.

Schlom (1991), "Monoclonal Antibodies: They're More and Less Than You Think," in *Molecular Foundations of Oncology*, pp. 95-133.

Schnee et al., (1987), "Construction and Expression of a Recombinant Antibody-Targeted Plasminogen Activator," *Proc. Natl. Sci. USA*, 84:6904-6908.

Schwartzberg et al., (2001), "Clinical Experience with Edrecolomab: A Monoclonal Antibody Therapy for Colon Carcinoma," *Critical Reviews in Oncology/Hematology*, 40:17-24.

Seidenfeld et al., (2001), "Epoietin Treatment of Anemia Associated with Cancer Therapy: A Systematic Review and Meta-Analysis of Controlled Clinical Trials," *Journal of National Cancer Institute*, 93(16):1204-1214.

Senior et al., (2000), "Cleavage of a Recombinant Human Immunoglobulin A2(igA2)-IgA1 Hybrid Antibody by Certain Bacterial IgAl Proteases," *Infect. Immun.*, 68(2):463-9.

Senter et al., (1988), "Anti-Tumor Effects of Antibody-Alkaline Phosphatase Conjugates in Combination with Etoposide Phosphate," *Proc. Natl. Acad. Sci. USA*, 85(13):4842-4846.

Sharma et al., (1999), "T cell-Derived IL-10 Promotes Lung Cancer Growth by Suppressing Both T cell and APC Function," *Journal of Immunology*, 163:5020-5028.

Sharp et al., (1988), "Codon Usage Patterns in *Escherichia coli, Bacillus subtilis, Saccharomyces cerevisiae, Schizosaccharomyces pombe, Drosophila melanogaster* and *Homo sapiens*; a Review of the Considerable Within-Species Diversity," *Nucleic Acids Res.*, 16(17):8207-8211.

Shen et al., (1986), "Heteroantibody-Mediated Cytotoxicity: Antibody to the High Affinity Fc Receptor for IgG Mediates Cytotoxicity by Human Monocytes that is Enhanced by Interferon-γ and is Not Blocked by Human IgG," *J. Immunology*, 137(11):3378-3382.

Shin et al., (1990), "Expression and Characterization of an Antibody Binding Specificity Joined to Insulin-Like Growth Factor 1: Potential Applications for Cellular Targeting," *Proc. Natl. Acad. Sci. USA*, 87:5322-5326.

Shinkawa et al., (2003), "The Absence of Fucose But Not the Presence of Galactose or Bisecting N-Acetylglucosamine of Human IgGl Complex-Type Oligosaccharides Shows the Critical Role of Enhancing Antibody-Dependent Cellular Cytotoxicity," *J. Biol. Chem.*, 278:3466-3473.

Spiekermann et al., (2002), "Receptor-Mediated Immunoglobulin G Transport Across Mucosal Barriers in Adult Life: Functional Expression of FcRn in the Mammalian Lung," *J. Exp. Med.*, 196:303-310.

Spivak et al., (1989), "The In Vivo Metabolism of Recombinant Human Erythropoietin in the Rat," *Blood*, 73:90-9.

Stevenson et al., (1997), "Conjugation of Human Fcγ in Closed-Hinge or Open-Hinge Configuration to Fab'γ and Analogues Ligands," *J. Immunology*, 158:2242-2250.

Suliman et al., (1996), "Cloning of a cDNA Encoding Bovine Erythropoietin and Analysis of Its Transcription in Selected Tissues," *Gene*, 171:275-80.

Syed et al., (1998), "Efficiency of Signaling Through Cytokine Receptors Depends Critically on Receptor Orientation," *Nature*, 395:511-516.

Takai, (2002), "Roles of Fc Receptors in Autoimmunity," *Nat. Rev. Immunol.*, 2(8):580-92.

Tao et al., (1989), "Studies of Aglycosylated Chimeric Mouse IgG: Role of Carbohydrate in the Structure and Effector Functions Mediated by the Human IgG Constant Region," *J. Immunology*, 143(8):2595-2601.

Tao et al., (1993), "Structural Features of Human Immunoglobulin G that Determine Isotype-Differences in Complement Activation," *J. Exp. Med.*, 178(2):661-667.

*The Merck Manual of Diagnosis and Therapy, 17th Ed.*, (1999) pp. 990-993 and 1278-1283.

Thommesen et al., (2000), "Lysine 322 in the Human IgG3 CH2 Domain is Crucial for Antibody Dependent Complement Activation," *Mol. Immunol.*, 37(16):995-1004.

Till et al., (1988), "An Assay that Predicts the Ability of Monoclonal Antibodies to Form Potent Ricin A Chain-Containing Immunotoxins," *Cancer Research*, 48(5):1119-1123.

Till et al., (1988), "HIV-Infected Cells are Killed by rCD4-Ricin A Chain," *Science*, 242:1166-1168.

Tiruppathi et al., (1996), "Isolation and Characterization of a Cell Surface Albumin-Binding Protein from Vascular Endothelial Cells," *Proc. Nat. Acad. Sci. USA*, 93:250-4.

Vagliani et al., (1996), "Interleukin 12 Potentiates the Curative Effect of a Vaccine Based on Interleukin 2-Transduced Tumor Cells," *Cancer Research*, 56:467-470.

Varki et al., (1984), "Antigens Associated with a Human Lung Adenocarcinoma Defined by Monoclonal Antibodies," *Cancer Research*, 44:681-687.

Verhoeyen et al., (1988), "Reshaping Human Antibodies: Grafting an Antilysozyme Activity," *Science*, 239:1534-36.

Voest et al., (1995), "Inhibition of Angiogenesis in Vivo by Interleukin 12," *J. Natl. Canc. Inst.*, 87:581-6.

Ward et al., (1995), "The Effector Functions of Immunoglobulins: Implications for Therapy," *Therapeutic. Immunology*, 2:77-94.

Weber et al., (2001), "Phase I Trial of huKS-IL2 Immunocytokine Patients with Prostate Carcinoma: Clinical, PK, and Biological PD Results (Abstract)," *American Society of Clinical Oncology Program/Proceedings*, 20(Part 1):259a.

Weitkamp et al., (1973), "Additional Data on the Population Distribution of Human Serum Albumin Genes; Three New Variants," *Ann. Hum. Genet.*, 37:219-26.

Wells, (1990), "Additivity of Mutational Effect in Proteins," *Biochemistry*, 29(37):8509-8517.

Wen et al., (1993), "Erythropoietin Structure-Function Relationships: High Degree of Sequence Homology Among Mammals," *Blood*, 82(5):1507-1516.

Wen et al., (1994), "Erthropoietin Structure-Function Relationships: Identification of Functionally Important Domains," *J. Biological Chemistry*, 269(36):22839-22846.

Went et al., (2004), "Frequent EpCam Protein Expression in Human Carcinomas," *Human Pathology*, 35(1):122-128.

Williams et al, (1986), "Production of Antibody-Tagged Enzymes by Myeloma Cells: Application to DNA Polymerase I Klenow Fragment," *Gene*, 43:319-324.

Woof et al., (1986), "Localisation of the Monocyte-Binding Region on Human Immunoglobulin G," *Mol. Immunol.*, 23:319-30.

Wooley et al., (1993), "Influence of a Recombinant Human Soluble Tumor Necrosis Factor Receptor Fc Fusion Protein on Type II Collagen-Induced Arthritis in Mice," *J. Immunology*, 151:6602-6607.

Wysocka et al., (1995), "Interleukin-12 is Required for Interferon-γ Production and Lethality in Lipopolysaccharide-Induced Shock in Mice," *Eur. J. Immunol.*, 25:672-6.

Xiang et al., (1997), "Elimination of Established Murine Colon Carcinoma Metastases by Antibody-Interleukin 2 Fusion Protein Therapy," *Cancer Research*, 57:4948-4955.

Xu et al., (1994), "Residue at Position 331 in the IgG1 and IgG4 CH2 Domains Contributes to Their Differential Ability to Bind and Activate Complement," *J. Biol. Chem.*, 269(5):3469-3474.

Yan et al., (1996), "Characterization of an Ig VH Idiotope that Results in Specific Homophilic Binding and Increased Avidity for Antigen," *J. Immunol.*, 157:1582-8.

Yeh et al., (1992), "Design of Yeast-Secreted Albumin Derivatives for Human Therapy: Biological and Antiviral Properties of a Serum Albumin-CD4 Genetic Conjugate," *Proc. Natl. Acad. Sci. USA*, 89:1904-8.

Yu et al., (1998), "Phase I Trial of a Human-Mouse Chimeric Anti-Disaloganglioside Monoclonal Antibody ch14.18 in Patients with Refractory Neuroblastoma and Osteosarcoma," *J. Clinical Oncology*, 16(6):2169-80.

Zheng et al., (1995), "Administration of Noncytolytic IL-10/Fc In Murine Models of Lipopolysaccharide-Induced Septic Shock and Allogeneic Islet Transplantation," *Journal of Immunol.*, 154:5590-5600.

Zhu et al., (2001), "MHC Class I-Related Neonatal Fc Receptor for IgG is Functionally Expressed in Monocytes, Intestinal Macrophages and Dendritic Cells," *J. Immunol.*, 166:3266-3276.

Zuckier et al., (1988), "Chimeric Human-Mouse IgG Antibodies with Shuffled Constant Region Exons Demonstrate that Multiple Domains Contribute to In Vivo Half-Life," *Cancer Res.*, 58(17):3905-8.

Chamow et al., (1996), "Immunoadhesins: Principles and Applications," *Trends in Biotechnology*, 14(2):52-60.

Cunningham et al., (1989), "High-Resolution Epitope mapping of hGH-receptor Interactions by Alanine-Scanning Mutagenesis," *Science*, 244:1081-5.

Database Uniprot, (Jul. 21, 1986), Database Accession No. P01859.

Jefferis et al., (1998), "IgG-Fc-Mediated Effector Functions: Molecular Definition of Interaction Sites for Effector Ligands and the Role of Glycosylation," *Immunological Reviews*, 163:59-76.

Lund et al., (1993), "Control of IgG/Fc Glycosylation: A Comparison of Oligosaccharides from Chimeric Human/Mouse and Mouse Subclass Immunoglobulin Gs," *Mol. Immunol.*, 30(8):741-748.

Egrie et al., (2001), "Development and Characterization of Novel Erythropoiesis Stimulating Protein (NESP)," *British Journal of Cancer*, 84(Supp. 1):3-10.

\* cited by examiner

FIG. 1A

```
                                                         250                  260                 270                 280
241   F L F P P K P K D T L M I S R T P E V T C V V V D V S H E D P P E V K F N W Y V D    GC1/118_HUMAN
237   F L F P P K P K D T L M I S R T P E V T C V V V D V S H E D P P E V  Q F  N W Y V D    GC2/118_HUMAN
238   F L F P P K P K D T L M I S R T P E V T C V V V D V S H E D P P E V  Q F  N W Y V D    GC4/118_HUMAN 290                  300                 310                 320
281   G V E V H N A K T K P R E E Q Y N S T Y R V V S V L T V L H Q D W L N G K E Y K    GC1/118_HUMAN
277   G V E V H N A K T K P R E E Q  F N  S T  E  R V V S V L T V  V  H Q D W L N G K E Y K    GC2/118_HUMAN
278   G V E V H N A K T K P R E E Q  F N  S T Y R V V S V L T V  V  H Q D W L N G K E Y K    GC4/118_HUMAN 330                  340                 350                 360
321   C K V S N K A L P A P I E K T I S K A K G Q P R E P Q V Y T L P P S R D E L T K    GC1/118_HUMAN
317   C K V S N K  G  L P A P I E K T I S K  T  K G Q P R E P Q V Y T L P P S R  E E M  T K    GC2/118_HUMAN
318   C K V S N K G L P  S S  I E K T I S K T K G Q P R E P Q V Y T L P P S  Q E E M  T K    GC4/118_HUMAN 370                  380                 390                 400
361   N Q V S L T C L V K G F Y P S D I A V E W E S N G Q P E N N Y K T T P P V L D S    GC1/118_HUMAN
357   N Q V S L T C L V K G F Y P S D I A V E W E S N G Q P E N N Y K T T P P M L D S    GC2/118_HUMAN
358   N Q V S L T C L V K G F Y P S D I A V E W E S N G Q P E N N Y K T T P P V L D S    GC4/118_HUMAN 370                  380                 390                 400
401   D G S F F L Y S K L T V D K S R W Q Q G N V F S C S V M H E A L H N H Y T Q K S    GC1/118_HUMAN
397   D G S F F L Y S K L T V D K S R W Q Q G N V F S C S V M H E A L H N H Y T Q K S    GC2/118_HUMAN
398   D G S F F L Y S  R  L T V D K S R W Q  E  G N V F S C S V M H E A L H N H Y T Q K S    GC4/118_HUMAN

441   L S L S P G K    GC1/118_HUMAN
437   L S L S P G K    GC2/118_HUMAN
438   L S L S  L  G K    GC4/118_HUMAN
```

FIG. 1B

Nucleic Acid Sequence encoding mature huFc-EPO:
huFc-g2h(FN>AQ)-M1-EPO

GAGCCCAAATCTTCTGACAAAACTCACACATGCCCACCGTGCCCAGGTAAGCCAGCCCAGGCCTCGCCCTC
CAGCTCAAGGCGGGACAGGTGCCCTAGAGTAGCCTCCAGGACACAGGCCCCAGTGGGTGCTGACACG
TCCACCTCCATCTTCCTCAGCACCACCTGTGCAGGACCGTCAGTCTTCTTCCCCCCAAAACCCAA
GGACACCCCTCATGATCTCCGGACCCCTGAGGTCACGTGCGTGGTGGTGGACGTGAGCCACGAAGACCCCG
AGGTCCAGTTCAACTGGTACGTGGACGGCGTGGAGGTGCATAATGCCAAGACAAAGCCACGGGAGGAGCAG
GCCCAGAGCACGTTCCGTGTGGTCAGCGTCCTCACCGTTGTGCACCAGGACTGGCTGAACGGCAAGGAGTA
CAAGTGCAAGGTCTCCAACAAAGCCCTCCCAGCCCCCATCGAGAAAACCATCTCCAAAACCAAAGGTGGGA
CCCGCGGGGTATGAGGGCCACATGGACAGAGGCCGTCTATCCCTGGGAGTGACCGCTGT
GCCAACCTCTGTCCCTACAGGGCAGCCCGAGAACCACAGGTGTACACCCTGCCCCCATCACGGGAGGAGA
TGACCAAGAACCAGGTCAGCCTGACCTGCCTGGTCAAAGGCTTCTACCCCAGCGACATCGCCGTGGAGTGG
GAGAGCAATGGGCAGCCGGAGAACAACTACAAGACCACACCTCCCATGCTGGACTCCGACGGCTCCTTCTT
CCTCTACAGCAAGCTCACCGTGGACAAGAGCAGGTGGCAGCAGGGGAACGTCTTCTCATGCTCCGTGATGC
ATGAGGCTCTGCACAACCACTACACGCAGAAGAGCGCCTCCCGGGCCCGACCCCACCACGCCTC
ATCTGTGACAGCGAGTGCTGGAGAGGTACCTCTTGGAGGCCAAGGAGCCGAGAATATCACGACCGGCTG
TGCTGAACACTGCAGCTTGAATGAGAACATCACCGTGCCTGACACCAAAGTGATTTCTCGGAAGA
GGATGGAGGTTGGCCAGCAGGCCGTAGAAGTGTGGCAGGGCCTGGGAGCCCTGCAACTGCATGTGAGCCGTGAG
GGCCAGGCCCTGTTGGTCAGCCTTCTTCCCAGCAGCCCCTGCTTCGGGAGCCTCTGGGAGCCAGAAGGAAGCCATCTCCCCTCCAGATG
TGGCCTTCGCAGCTGCTCAGCTGCTCCCCACACTCACTCTGCTGACACTTTCCGCAAACTCTTCCGAGTCTACTCCAAT
TTCCTCCGGGAAAGCTGTACACAGGGGAGGCCTGCCGGACAGGGGACACAGATGA

FIG. 7

SEQUENCE LISTING

```
<160> NUMBER OF SEQ ID NOS: 24

<210> SEQ ID NO 1
<211> LENGTH: 501
<212> TYPE: DNA
<213> ORGANISM: Artificial Sequence
<220> FEATURE:
<223> OTHER INFORMATION: An exemplary codon-optimized nucleic acid
      sequence encoding an erythropoietin portion.

<400> SEQUENCE: 1
gccccaccac gcctcatctg tgacagccga gtgctggaga ggtacctctt ggaggccaag      60
gaggccgaga atatcacgac cggctgtgct gaacactgca gcttgaatga gaacatcacc     120
gtgcctgaca ccaaagtgaa tttctatgcc tggaagagga tggaggttgg ccagcaggcc     180
gtagaagtgt ggcagggcct ggccctgctg tcggaagctg tcctgcgggg ccaggccctg     240
ttggtcaact cttcccagcc gtgggagccc ctgcaactgc atgtggataa agccgtgagt     300
```

```
ggccttcgca gcctcaccac tctgcttcgg gctctgggag cccagaagga agccatctcc    360
cctccagatg cggcctcagc tgctcccctc cgcacaatca ctgctgacac tttccgcaaa    420
ctcttccgag tctactccaa tttcctccgg ggaaagctga agctgtacac aggggaggcc    480
tgccggacag gggacagatg a                                              501
```

<210> SEQ ID NO 2
<211> LENGTH: 1409
<212> TYPE: DNA
<213> ORGANISM: Artificial Sequence
<220> FEATURE:
<223> OTHER INFORMATION: An exemplary nucleic acid sequence encoding a mature Fc-EPO protein without a leader sequence.

<400> SEQUENCE: 2

```
gagcccaaat cttctgacaa aactcacaca tgcccaccgt gcccaggtaa gccagcccag     60
gcctcgccct ccagctcaag gcgggacagg tgccctagag tagcctgcat ccagggacag    120
gccccagctg ggtgctgaca cgtccacctc catctcttcc tcagcaccac ctgtggcagg    180
accgtcagtc ttcctcttcc ccccaaaacc caaggacacc ctcatgatct cccgacccc     240 tgaggtcacg tgcgtggtgg tggacgtgag ccacgaagac cccgaggtcc agttcaactg    300
gtacgtggac ggcgtggagg tgcataatgc caagacaaag ccacgggagg agcaggccca    360
gagcacgttc cgtgtggtca gcgtcctcac cgttgtgcac caggactggc tgaacggcaa    420
ggagtacaag tgcaaggtct ccaacaaagg cctcccagcc cccatcgaga aaaccatctc    480
caaaaccaaa ggtgggaccc gcggggtatg agggccacat ggacagaggc cggctcggcc    540
caccctctgc cctgggagtg accgctgtgc aacctctgt ccctacaggg cagccccgag     600
aaccacaggt gtacaccctg cccccatcac gggaggagat gaccaagaac caggtcagcc    660
tgacctgcct ggtcaaaggc ttctaccccca gcgacatcgc cgtggagtgg gagagcaatg    720
ggcagccgga gaacaactac aagaccacac ctcccatgct ggactccgac ggctccttct    780
tcctctacag caagctcacc gtggacaaga gcaggtggca gcagggaac gtcttctcat     840 gctccgtgat gcatgaggct ctgcacaacc actacacgca gaagagcgcc accgcgaccc    900
cgggcgccgc cccaccacgc ctcatctgtg acagccgagt gctggagagg tacctcttgg    960
aggccaagga ggccgagaat atcacgaccg gctgtgctga acactgcagc ttgaatgaga   1020
acatcaccgt gcctgacacc aaagtgaatt tctatgcctg gaagaggatg gaggttggcc   1080
agcaggccgt agaagtgtgg cagggcctgg ccctgctgtc ggaagctgtc ctgcggggcc   1140
aggccctgtt ggtcaactct cccagccgt gggagccct gcaactgcat gtggataaag   1200
ccgtgagtgg ccttcgcagc ctcaccactc tgcttcgggc tctgggagcc agaaggaag    1260 ccatctcccc tccagatgcg gcctcagctg ctcccctccg cacaatcact gctgacactt   1320
tccgcaaact cttccgagtc tactccaatt tcctccgggg aaagctgaag ctgtacacag   1380
gggaggcctg ccggacaggg gacagatga                                     1409
```

<210> SEQ ID NO 3
<211> LENGTH: 514
<212> TYPE: DNA
<213> ORGANISM: Artificial Sequence
<220> FEATURE:
<223> OTHER INFORMATION: An example of coding sequences of mature human erythropoietin with modified codons to optimize translation.

<400> SEQUENCE: 3

```
cccgggtgcc ccaccacgcc tcatctgtga cagccgagtg ctggagaggt acctcttgga     60
```

```
ggccaaggag gccgagaata tcacgaccgg ctgtgctgaa cactgcagct tgaatgagaa    120
catcaccgtg cctgacacca aagtgaattt ctatgcctgg aagaggatgg aggttggcca    180
gcaggccgta gaagtgtggc agggcctggc cctgctgtcg gaagctgtcc tgcggggcca    240
ggccctgttg gtcaactctt cccagccgtg ggagcccctg caactgcatg tggataaagc    300
cgtgagtggc cttcgcagcc tcaccactct gcttcgggct ctgggagccc agaaggaagc    360
catctcccct ccagatgcgg cctcagctgc tcccctccgc acaatcactg ctgacacttt    420
ccgcaaactc ttccgagtct actccaattt cctccgggga aagctgaagc tgtacacagg    480
ggaggcctgc cggacagggg acagatgact cgag                                514

<210> SEQ ID NO 4
<211> LENGTH: 166
<212> TYPE: PRT
<213> ORGANISM: Artificial Sequence
<220> FEATURE:
<223> OTHER INFORMATION: Human erythropoietin protein sequence with
      substitutions His32Gly, Cys33Pro, Trp88Cys, and Pro90Ala.

<400> SEQUENCE: 4

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu Gly
            20                  25                  30

Pro Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Cys Glu Gly Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 5
<211> LENGTH: 17
<212> TYPE: PRT
<213> ORGANISM: Artificial Sequence
<220> FEATURE:
<223> OTHER INFORMATION: An exemplary sequence at the junction of the
      CH3 C-terminus and the EPO N-terminus.

<400> SEQUENCE: 5

Thr Gln Lys Ser Ala Thr Ala Thr Pro Gly Ala Ala Pro Pro Arg Leu
1               5                   10                  15

Ile

<210> SEQ ID NO 6
```

```
<211> LENGTH: 8
<212> TYPE: PRT
<213> ORGANISM: Homo sapiens

<400> SEQUENCE: 6

Lys Ser Leu Ser Leu Ser Pro Gly
1               5

<210> SEQ ID NO 7
<211> LENGTH: 8
<212> TYPE: PRT
<213> ORGANISM: Artificial Sequence
<220> FEATURE:
<223> OTHER INFORMATION: An altered IgG2 CH3 region.

<400> SEQUENCE: 7

Lys Ser Ala Thr Ala Thr Pro Gly
1               5

<210> SEQ ID NO 8
<211> LENGTH: 35
<212> TYPE: DNA
<213> ORGANISM: Artificial Sequence
<220> FEATURE:
<223> OTHER INFORMATION: A primer suitable for amplifying Hygromycin B
      gene.

<400> SEQUENCE: 8
gctagcttgg tgccctcatg aaaaagcctg aactc                        35

<210> SEQ ID NO 9
<211> LENGTH: 25
<212> TYPE: DNA
<213> ORGANISM: Artificial Sequence
<220> FEATURE:
<223> OTHER INFORMATION: A primer for amplifying Hygromycin B gene.

<400> SEQUENCE: 9
atgcattcag ttagcctccc ccatc                                   25

<210> SEQ ID NO 10
<211> LENGTH: 28
<212> TYPE: DNA
<213> ORGANISM: Artificial Sequence
<220> FEATURE:
<223> OTHER INFORMATION: A mutagenic primer leading to a double amino
      acid substitution, "FN>AQ", within the Gln-Phe-Asn-Ser amino acid
      sequence within the CH2 domain of the IgG2 heavy chain.

<400> SEQUENCE: 10
agcaggccca gagcacgttc cgtgtggt                                28

<210> SEQ ID NO 11
<211> LENGTH: 28
<212> TYPE: DNA
<213> ORGANISM: Artificial Sequence
<220> FEATURE:
<223> OTHER INFORMATION: A mutagenic primer leading to a double amino
      acid substitution, "FN>AQ", within the Gln-Phe-Asn-Ser amino acid
      sequence within the CH2 domain of the IgG2 heavy chain.

<400> SEQUENCE: 11
gaacgtgctc tgggcctgct cctcccgt                                28

<210> SEQ ID NO 12
<211> LENGTH: 21
<212> TYPE: DNA
```

-continued

```
<213> ORGANISM: Artificial Sequence
<220> FEATURE:
<223> OTHER INFORMATION: A downstream primer containing a Sac II site.

<400> SEQUENCE: 12
ccccgcgggt cccacctttg g                                              21

<210> SEQ ID NO 13
<211> LENGTH: 21
<212> TYPE: DNA
<213> ORGANISM: Artificial Sequence
<220> FEATURE:
<223> OTHER INFORMATION: An upstream primer containing a Pvu II site.

<400> SEQUENCE: 13
cccagctggg tgctgacacg t                                              21

<210> SEQ ID NO 14
<211> LENGTH: 397
<212> TYPE: PRT
<213> ORGANISM: Artificial Sequence
<220> FEATURE:
<223> OTHER INFORMATION: An amino acid sequence of Fc-EPO containing
      FN>AQ mutations.

<400> SEQUENCE: 14

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Gln Phe Asn Trp Tyr Val Asp
    50                  55                  60

Gly Val Glu Val His Asn Ala Lys Thr Lys Pro Arg Glu Glu Gln Ala
65                  70                  75                  80

Gln Ser Thr Phe Arg Val Val Ser Val Leu Thr Val Val His Gln Asp
                85                  90                  95

Trp Leu Asn Gly Lys Glu Tyr Lys Cys Lys Val Ser Asn Lys Gly Leu
            100                 105                 110

Pro Ala Pro Ile Glu Lys Thr Ile Ser Lys Thr Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Ala Thr Ala Thr Pro Gly Ala Ala Pro Arg Leu Ile Cys Asp Ser
225                 230                 235                 240

Arg Val Leu Glu Arg Tyr Leu Leu Glu Ala Lys Glu Ala Glu Asn Ile
                245                 250                 255
```

```
Thr Thr Gly Cys Ala Glu His Cys Ser Leu Asn Glu Asn Ile Thr Val
            260                 265                 270

Pro Asp Thr Lys Val Asn Phe Tyr Ala Trp Lys Arg Met Glu Val Gly
            275                 280                 285

Gln Gln Ala Val Glu Val Trp Gln Gly Leu Ala Leu Leu Ser Glu Ala
            290                 295                 300

Val Leu Arg Gly Gln Ala Leu Leu Val Asn Ser Ser Gln Pro Trp Glu
305                 310                 315                 320

Pro Leu Gln Leu His Val Asp Lys Ala Val Ser Gly Leu Arg Ser Leu
            325                 330                 335

Thr Thr Leu Leu Arg Ala Leu Gly Ala Gln Lys Glu Ala Ile Ser Pro
            340                 345                 350

Pro Asp Ala Ala Ser Ala Ala Pro Leu Arg Thr Ile Thr Ala Asp Thr
            355                 360                 365

Phe Arg Lys Leu Phe Arg Val Tyr Ser Asn Phe Leu Arg Gly Lys Leu
370                 375                 380

Lys Leu Tyr Thr Gly Glu Ala Cys Arg Thr Gly Asp Arg
385                 390                 395

<210> SEQ ID NO 15
<211> LENGTH: 397
<212> TYPE: PRT
<213> ORGANISM: Artificial Sequence
<220> FEATURE:
<223> OTHER INFORMATION: The amino acid sequence of Fc-EPO(NDS) encoded
      by pdC10-huFcg2h(FN>AQ)-M1-EPO.

<400> SEQUENCE: 15

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Ser His Glu Asp Pro Glu Val Gln Phe Asn Trp Tyr Val Asp
        50                  55                  60

Gly Val Glu Val His Asn Ala Lys Thr Lys Pro Arg Glu Glu Gln Ala
65                  70                  75                  80

Gln Ser Thr Phe Arg Val Val Ser Val Leu Thr Val Val His Gln Asp
            85                  90                  95

Trp Leu Asn Gly Lys Glu Tyr Lys Cys Lys Val Ser Asn Lys Gly Leu
            100                 105                 110

Pro Ala Pro Ile Glu Lys Thr Ile Ser Lys Thr Lys Gly Gln Pro Arg
            115                 120                 125

Glu Pro Gln Val Tyr Thr Leu Pro Pro Ser Arg Glu Glu Met Thr Lys
            130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
            165                 170                 175

Thr Thr Pro Pro Met Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
            210                 215                 220
```

-continued

```
Ala Thr Ala Thr Pro Gly Ala Ala Pro Pro Arg Leu Ile Cys Asp Ser
225                 230                 235                 240

Arg Val Leu Glu Arg Tyr Leu Leu Glu Ala Lys Glu Ala Glu Asn Ile
            245                 250                 255

Thr Thr Gly Cys Ala Glu Gly Pro Ser Leu Asn Glu Asn Ile Thr Val
        260                 265                 270

Pro Asp Thr Lys Val Asn Phe Tyr Ala Trp Lys Arg Met Glu Val Gly
    275                 280                 285

Gln Gln Ala Val Glu Val Trp Gln Gly Leu Ala Leu Leu Ser Glu Ala
290                 295                 300

Val Leu Arg Gly Gln Ala Leu Leu Val Asn Ser Ser Gln Pro Cys Glu
305                 310                 315                 320

Ala Leu Gln Leu His Val Asp Lys Ala Val Ser Gly Leu Arg Ser Leu
            325                 330                 335

Thr Thr Leu Leu Arg Ala Leu Gly Ala Gln Lys Glu Ala Ile Ser Pro
        340                 345                 350

Pro Asp Ala Ala Ser Ala Ala Pro Leu Arg Thr Ile Thr Ala Asp Thr
    355                 360                 365

Phe Arg Lys Leu Phe Arg Val Tyr Ser Asn Phe Leu Arg Gly Lys Leu
370                 375                 380

Lys Leu Tyr Thr Gly Glu Ala Cys Arg Thr Gly Asp Arg
385                 390                 395

<210> SEQ ID NO 16
<211> LENGTH: 4
<212> TYPE: PRT
<213> ORGANISM: Homo sapiens

<400> SEQUENCE: 16

Gln Phe Asn Ser
1

<210> SEQ ID NO 17
<211> LENGTH: 4
<212> TYPE: PRT
<213> ORGANISM: Artificial Sequence
<220> FEATURE:
<223> OTHER INFORMATION: A CH2 domain derived from a human IgG2 or IgG4
      heavy chain.

<400> SEQUENCE: 17

Gln Ala Gln Ser
1

<210> SEQ ID NO 18
<211> LENGTH: 6
<212> TYPE: PRT
<213> ORGANISM: Homo sapiens

<400> SEQUENCE: 18

Pro Lys Ser Cys Asp Lys
1               5

<210> SEQ ID NO 19
<211> LENGTH: 6
<212> TYPE: PRT
<213> ORGANISM: Artificial Sequence
<220> FEATURE:
<223> OTHER INFORMATION: An altered IgG1 hinge region.

<400> SEQUENCE: 19
```

```
Pro Lys Ser Ser Asp Lys
1               5

<210> SEQ ID NO 20
<211> LENGTH: 4
<212> TYPE: PRT
<213> ORGANISM: Homo sapiens

<400> SEQUENCE: 20

Leu Ser Leu Ser
1

<210> SEQ ID NO 21
<211> LENGTH: 4
<212> TYPE: PRT
<213> ORGANISM: Artificial Sequence
<220> FEATURE:
<223> OTHER INFORMATION: An altered IgG sequence

<400> SEQUENCE: 21

Ala Thr Ala Thr
1

<210> SEQ ID NO 22
<211> LENGTH: 330
<212> TYPE: PRT
<213> ORGANISM: Homo sapiens

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
```

```
                225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Tyr Ser Lys Leu Thr Val Asp Lys Ser Arg Trp Gln Gln Gly Asn
                290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 23
<211> LENGTH: 326
<212> TYPE: PRT
<213> ORGANISM: Homo sapiens

<400> SEQUENCE: 23

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
            50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
                100                 105                 110
Pro Val Ala Gly Pro Ser Val Phe Leu Phe Pro Pro Lys Pro Lys Asp
            115                 120                 125
Thr Leu Met Ile Ser Arg Thr Pro Glu Val Thr Cys Val Val Val Asp
                130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
                180                 185                 190
Leu Asn Gly Lys Glu Tyr Lys Cys Lys Val Ser Asn Lys Gly Leu Pro
            195                 200                 205
Ala Pro Ile Glu Lys Thr Ile Ser Lys Thr Lys Gly Gln Pro Arg Glu
            210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
                260                 265                 270
```

```
Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 24
<211> LENGTH: 327
<212> TYPE: PRT
<213> ORGANISM: Homo sapiens

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

```
Leu Ser Leu Ser Leu Gly Lys
                325
```

FC-ERYTHROPOIETIN FUSION PROTEIN WITH IMPROVED PHARMACOKINETICS

REFERENCE TO RELATED APPLICATIONS

This application claims the benefit of U.S. Ser. No. 60/533,858, filed Dec. 31, 2003, the entire contents of which are incorporated by reference into the present application.

FIELD OF THE INVENTION

The present invention relates generally to methods and compositions for effective erythropoietin therapy. More specifically, the present invention relates to a fusion protein containing an erythropoietin portion that has prolonged serum half-life and increased in vivo potency.

BACKGROUND

Erythropoietin is a glycoprotein hormone necessary for the maturation of erythroid progenitor cells into erythrocytes. It is produced in the kidney and is essential in regulating levels of red blood cells in the circulation. Conditions marked by low levels of tissue oxygen signal increases in production of erythropoietin, which in turn stimulates erythropoiesis. The erythropoietin level in the circulation is strictly regulated to ensure that red blood cells are made only in response to a long-term oxygen deficit. 70% of erythropoietin is cleared by receptor-mediated endocytosis. When erythropoietin binds to its receptor, the complex is endocytosed and degraded, thus limiting the extent of signaling. The remainder of erythropoietin is cleared through kidney filtration into the urine. As a result, erythropoietin has a relatively short serum half-life.

Naturally-occurring human erythropoietin or recombinant erythropoietin produced in mammalian cells contains three N-linked and one O-linked oligosaccharide chains. N-linked glycosylation occurs at asparagine residues located at positions 24, 38 and 83, while O-linked glycosylation occurs at a serine residue located at position 126 (Lai et al., (1986) *J. Biol. Chem.* 261:3116; Broudy et al., (1988) *Arch. Biochem. Biophys.* 265:329). The oligosaccharide chains have been shown to be modified with terminal sialic acid residues. N-linked chains typically have up to four sialic acids per chain and O-linked chains have up to two sialic acids. An erythropoietin polypeptide may therefore accommodate up to a total of 14 sialic acids. It has been shown that the carbohydrate is required for secretion of erythropoietin from cells, for increasing the solubility of erythropoietin, and for the in vivo biological activity of erythropoietin (Dube et al., (1988) *J. Biol. Chem.* 263:17516; DeLorme et al., (1992) *Biochemistry* 31:9871-9876).

Administration of recombinant human erythropoietin has been effective in treating hematopoietic disorders or deficiencies, such as, for example, different forms of anemia, including those associated with renal failure, HIV infection, blood loss and chronic disease. Erythropoietin is typically administered by intravenous injection. Since erythropoietin has a relatively short serum half-life, frequent intravenous injections are required to maintain a therapeutically effective level of erythropoietin in the circulation. Pharmaceutical compositions containing naturally-occurring or recombinant human erythropoietin are typically administered three times per week at a dose of approximately 25-100 Units/kg. This form of erythropoietin therapy, although quite effective, is very expensive and inconvenient because intravenous administration often necessitates a visit to a doctor or hospital. Currently, a hyperglycosylated recombinant human erythropoietin analogue, novel erythropoiesis stimulating protein (NESP), is available under the trademark Aranesp® (Amgen Inc., Thousand Oaks, Calif.) for treatment of anemia. Aranesp® can be administered less frequently than regular erythropoietin to obtain the same biological response.

An alternative route of administration is subcutaneous injection. This form of administration may be performed by patients at home, and is more compatible with slow-release formulations offering slower absorption from the site of administration, thus causing a sustained release effect. However, significantly lower circulation levels are achieved by subcutaneous injection and, thus, frequent injections are required to achieve desirable therapeutic effect. Furthermore, subcutaneous administration of protein drugs is generally more immunogenic than intravenous administration because the skin, as the major barrier to infection, is an immune organ that is rich in dendritic cells and has sensitive mechanisms for identifying and responding to abrasions and foreign materials. Casadevall et al. recently reported that patients receiving erythropoietin subcutaneously developed anti-erythropoietin antibodies (Casadevall et al. (2002) *N Engl. J. Med.* 346(7): 469-75).

Accordingly, there is a need for a more efficient erythropoietin therapy that requires less frequent administrations.

SUMMARY OF THE INVENTION

The present invention provides erythropoietin fusion proteins with improved pharmacokinetics compared, in various embodiments, to wild-type or naturally-occurring erythropoietin, to recombinant erythropoietin, or to hyperglycosylated erythropoietin analogue NESP (PCT publication WO 00/24893). Accordingly, it is an object of the present invention to simplify erythropoietin therapy and to reduce the costs associated with treating humans or other mammals with hematopoietic disorders or deficiencies or other indications for erythropoietin administration.

Specifically, the present invention provides a biologically active Fc-erythropoietin (Fc-EPO) fusion protein that has prolonged serum half-life and increased in vivo potency. "Fc-EPO fusion protein," as used herein, refers to a protein comprising a polypeptide having an Fc portion and an erythropoietin portion. "Fc portion," as used herein, encompasses domains derived from the constant region of an immunoglobulin, preferably a human immunoglobulin, including a fragment, analog, variant, mutant or derivative of the constant region. "Erythropoietin portion," as used herein, encompasses wild-type or naturally-occurring erythropoietin from human and other species, recombinant erythropoietin, and erythropoietin-like molecules, including biologically-active erythropoietin fragments, analogs, variants, mutants or derivatives of erythropoietin.

In one aspect, the present invention provides Fc-EPO proteins synthesized in BHK cells. The inventive Fc-EPO fusion proteins synthesized in BHK cells have demonstrated dramatically prolonged serum half-lives and increased in vivo potency when compared to corresponding Fc-EPO fusion proteins produced in other cell lines, such as, for example, NS/0, PerC6, or 293 cells. The present invention also provides a population of highly sialylated Fc-EPO fusion proteins suitable for administration to a mammal. The highly sialylated Fc-EPO fusion proteins have longer serum half-lives and increased in vivo potency compared, in various embodiments, to wild-type or naturally-occurring erythropoietin, to recombinant erythropoietin, to hyperglycosylated erythropoietin analogue NESP, or to Fc-EPO fusion proteins of the same amino acid sequence synthesized in NS/0, PerC6, or 293 cells. In accordance with the present invention, an Fc-EPO fusion protein can contain amino acid modifications in the Fc portion that generally extend the serum half-life of an Fc fusion protein. For example, such amino acid modifications include mutations substantially decreasing or eliminating Fc receptor binding or complement fixing activity. In addition, the Fc-EPO fusion protein can also contain amino acid modifications in the erythropoietin portion that reduce EPO receptor-mediated endocytosis or increase the biological activity of erythropoietin. In various embodiments, the present invention combines the benefits provided by an immunoglobulin fusion protein, amino acid modifications of the Fc and erythropoietin portions, and production in BHK cells (e.g., high levels of sialylation). The combined benefits have additive or synergistic effects resulting in an Fc-EPO fusion protein with a surprisingly prolonged serum half-life and an increased in vivo potency.

Accordingly, the present invention in one aspect relates to a BHK cell containing a nucleic acid sequence encoding an Fc-EPO fusion protein. In one embodiment, the BHK cell of the present invention is adapted for growth in a protein-free medium. In another embodiment, the BHK cell is adapted for growth in suspension. In yet another embodiment, the BHK cell is adapted for growth in a protein-free medium and in suspension. It has been found that the Fc-EPO fusion proteins produced from BHK cells grown in a protein-free medium exhibited surprisingly increased and more homogeneous sialylation compared to Fc-EPO fusion proteins produced from BHK cells grown in other media. In a preferred embodiment, the nucleic acid is stably maintained in the BHK cell. "Stably maintained nucleic acid," as used herein, refers to any nucleic acid whose rate of loss from a mother cell to a daughter cell is less than three percent in the absence of selective pressure, such as an antibiotic-based selection, to maintain the nucleic acid. Thus, when cells stably maintaining a nucleic acid divide, at least 97 percent (and, more preferably, more than 98, more than 99, or more than 99.5 percent) of the resulting cells contain the nucleic acid. When the resulting cells containing the nucleic acid divide, at least 97 percent of the cells resulting from that (second) division will contain the nucleic acid. Furthermore, the number of copies per cell of the nucleic acid is not substantially reduced by repeated cell division. In a preferred embodiment, the stably maintained nucleic acid sequence is integrated in a chromosome of a BHK cell.

The nucleic acid sequence can encode the Fc-EPO fusion protein in any of various configurations. In a preferred embodiment, the nucleic acid sequence encodes an Fc-EPO fusion protein that includes an Fc portion towards the N-terminus of the Fc-EPO fusion protein and an erythropoietin portion towards the C-terminus of the Fc-EPO fusion protein. The Fc portion generally encompasses regions derived from the constant region of an immunoglobulin, including a fragment, analog, variant, mutant or derivative of the constant region. In preferred embodiments, the Fc portion is derived from a human immunoglobulin heavy chain, for example, IgG1, IgG2, IgG3, IgG4, or other classes. In some embodiments, the Fc-EPO fusion protein does not include a variable region of an immunoglobulin. In one embodiment, the Fc portion includes a CH2 domain. In another embodiment, the Fc portion includes CH2 and CH3 domains.

In a preferred embodiment, the Fc portion contains a mutation that reduces affinity for an Fc receptor or reduces Fc effector function. For example, the Fc portion can contain a mutation that eliminates the glycosylation site within the Fc portion of an IgG heavy chain. In some embodiments, the Fc portion contains mutations, deletions, or insertions at an amino acid position corresponding to Leu234, Leu235, Gly236, Gly237, Asn297, or Pro331 of IgG1 (amino acids are numbered according to EU nomenclature). In a preferred embodiment, the Fc portion contains a mutation at an amino acid position corresponding to Asn297 of IgG1. In alternative embodiments, the Fc portion contains mutations, deletions, or insertions at an amino acid position corresponding to Leu281, Leu282, Gly283, Gly284, Asn344, or Pro378 of IgG1.

In some embodiments, the Fc portion contains a CH2 domain derived from a human IgG2 or IgG4 heavy chain. Preferably, the CH2 domain contains a mutation that eliminates the glycosylation site within the CH2 domain. In one embodiment, the mutation alters the asparagine within the Gln-Phe-Asn-Ser (SEQ ID NO:16) amino acid sequence within the CH2 domain of the IgG2 or IgG4 heavy chain. Preferably, the mutation changes the asparagine to a glutamine. Alternatively, the mutation alters both the phenylalanine and the asparagine within the Gln-Phe-Asn-Ser (SEQ ID NO:16) amino acid sequence. In one embodiment, the Gln-Phe-Asn-Ser (SEQ ID NO:16) amino acid sequence is replaced with a Gln-Ala-Gln-Ser (SEQ ID NO:17) amino acid sequence.

The asparagine within the Gln-Phe-Asn-Ser (SEQ ID NO:16) amino acid sequence corresponds to Asn297 of IgG1. It has been found that mutation of the asparagine within the Gln-Phe-Asn-Ser (SEQ ID NO:16) amino acid sequence of IgG2 or IgG4 (i.e., corresponding to Asn297 of IgG1) also surprisingly reduces the binding of the Fc-EPO fusion protein for the EPO receptor. Without wishing to be bound by theory, the mutation of the asparagine within the Gln-Phe-Asn-Ser (SEQ ID NO:16) amino acid sequence of IgG2 or IgG4 (i.e., corresponding to Asn297 of IgG1) may induce an overall conformational change in the Fc-EPO fusion protein, leading to dramatically improved pharmacokinetic properties.

In another embodiment, the Fc portion includes a CH2 domain and at least a portion of a hinge region. The hinge region can be derived from an immunoglobulin heavy chain, e.g., IgG1, IgG2, IgG3, IgG4, or other classes. Preferably, the hinge region is derived from human IgG1, IgG2, IgG3, IgG4, or other suitable classes. More preferably the hinge region is derived from a human IgG1 heavy chain. In one embodiment the cysteine in the Pro-Lys-Ser-Cys-Asp-Lys (SEQ ID NO:18) amino acid sequence of the IgG1 hinge region is altered. In a preferred embodiment the Pro-Lys-Ser-Cys-Asp-Lys (SEQ ID NO:18) amino acid sequence is replaced with a Pro-Lys-Ser-Ser-Asp-Lys (SEQ ID NO:19) amino acid sequence. In one embodiment, the Fc portion includes a CH2 domain derived from a first antibody isotype and a hinge region derived from a second antibody isotype. In a specific embodiment, the CH2 domain is derived from a human IgG2 or IgG4 heavy chain, while the hinge region is derived from an altered human IgG1 heavy chain.

In a preferred embodiment, the Fc portion is derived from an IgG sequence in which the Leu-Ser-Leu-Ser (SEQ ID NO:20) amino acid sequence near the C-terminus of the constant region is altered to eliminate potential junctional T-cell epitopes. For example, in one embodiment, the Leu-Ser-Leu-Ser amino acid sequence is replaced with an Ala-Thr-Ala-Thr (SEQ ID NO:21) amino acid sequence. In another embodiment, the Fc portion is derived from an IgG sequence in which the C-terminal lysine residue is replaced. Preferably, the C-terminal lysine of an IgG sequence is replaced with a non-lysine amino acid, such as alanine, to further increase the serum half-life of the Fc fusion protein.

In accordance with the present invention, the Fc portion can contain one or more mutations described herein. The combinations of mutations in the Fc portion generally have additive or synergistic effects on the prolonged serum half-life and increased in vivo potency of the Fc-EPO fusion protein. Thus, in one exemplary embodiment, the Fc portion can contain (i) a region derived from an IgG sequence in which the Leu-Ser-Leu-Ser (SEQ ID NO:20) amino acid sequence is replaced with an Ala-Thr-Ala-Thr (SEQ ID NO:21) amino acid sequence; (ii) a C-terminal alanine residue instead of lysine; (iii) a CH2 domain and a hinge region that are derived from different antibody isotypes, for example, an IgG2 CH2 domain and an altered IgG1 hinge region; (iv) a mutation that eliminates the glycosylation site within the IgG2-derived CH2 domain, for example, a Gln-Ala-Gln-Ser (SEQ ID NO:17) amino acid sequence instead of the Gln-Phe-Asn-Ser (SEQ ID NO:16) amino acid sequence within the IgG2-derived CH2 domain.

The erythropoietin portion of the Fc-EPO fusion protein can be a full length wild-type or naturally-occurring erythropoietin, a recombinant erythropoietin, or an erythropoietin-like molecule, such as a biologically-active erythropoietin fragment, analog, variant, mutant or derivative of erythropoietin. Preferably, the erythropoietin portion is derived from a human erythropoietin. In some embodiments, the erythropoietin portion can contain amino acid modifications that reduce binding affinity for EPO receptor or increase the biological activity of erythropoietin. In some embodiments, the erythropoietin portion contains at least one of the following mutations: $Arg_{131} \rightarrow Glu$ and $Arg_{139} \rightarrow Glu$ (amino acid numbering based on mature human erythropoietin sequence). In other embodiments, the erythropoietin portion contains at least one of the following mutations: $His_{32} \rightarrow Gly$, $Ser_{34} \rightarrow Arg$, and $Pro_{90} \rightarrow Ala$. In yet another embodiment, the erythropoietin portion has a pattern of disulfide bonding distinct from human erythropoietin. For example, the erythropoietin portion can contain one or more of the following amino acid substitutions: a non-cysteine residue at position 29, a non-cysteine residue at position 33, a cysteine residue at position 88, and a cysteine residue at position 139. In one embodiment, the erythropoietin portion contains cysteine residues at positions 7, 29, 88, and 161. In another embodiment, the erythropoietin portion in addition contains one or more of the following substitutions $His_{32} \rightarrow Gly$, $Cys_{33} \rightarrow Pro$, and $Pro_{90} \rightarrow Ala$. In accordance with the present invention, the erythropoietin portion can contain any combination of the mutations described herein.

In some embodiments, the Fc-EPO fusion protein includes a linker between the Fc portion and the erythropoietin portion. If included, the linker generally contains between 1 and 25 amino acids and preferably has no protease cleavage site. The linker can contain an N-linked or an O-linked glycosylation site to block proteolysis. For example, in one embodiment, the linker contains an Asn-Ala-Thr amino acid sequence.

The present invention also relates to a method of producing an Fc-EPO fusion protein. The method includes maintaining BHK cells containing a nucleic acid sequence encoding an Fc-EPO fusion protein under conditions suitable for expression of the encoded Fc-EPO fusion protein, and recovering the expressed Fc-EPO fusion protein. In one embodiment, the BHK cells are cultured in a protein-free medium. In another embodiment, the BHK cells are cultured in suspension. In yet another embodiment, the BHK cells are cultured in a protein-free medium and in suspension. In some embodiments, the nucleic acid is stably maintained in the BHK cells. Generally, the Fc-EPO fusion protein produced in the BHK cells has a longer serum half-life than a corresponding Fc-EPO fusion protein produced in other cell lines, such as, for example, NS/0, PerC6, or 293 cells.

The present invention provides a pharmaceutical composition containing the Fc-EPO fusion protein produced in BHK cells. In a preferred embodiment, the Fc-EPO fusion protein used in the pharmaceutical composition has not been treated to remove sialic acid residues. The pharmaceutical composition also includes a pharmaceutically acceptable carrier. The present invention also provides a method of treating a mammal by administering the pharmaceutical composition to the mammal. In some embodiments, the treated mammal has a hematopoietic disorder or deficiency. Because the Fc-EPO fusion proteins of the present invention have increased in vivo potency and prolonged serum half-life, pharmaceutical compositions containing the Fc-EPO fusion proteins generally require less frequent administration compared to pharmaceutical compositions containing naturally-occurring or recombinant erythropoietin or corresponding Fc-EPO fusion proteins produced in other cells. In a preferred embodiment, the pharmaceutical composition is administered fewer than three times per week (e.g., twice weekly, weekly, or not more than once every ten days, such as once every two weeks, once per month or once every two months).

In another aspect, the present invention provides a method of selecting a BHK cell that stably maintains a nucleic acid encoding a fusion protein including an Fc portion and an erythropoietin portion. The method includes introducing into a BHK cell a nucleic acid sequence encoding hygromycin B and a nucleic acid sequence encoding the fusion protein; and culturing the BHK cell in the presence of hygromycin B. In one embodiment, the nucleic acid sequence encoding hygromycin B and the nucleic acid sequence encoding the fusion protein are present in a single nucleic acid. In another embodiment, the nucleic acid sequence encoding hygromycin B and the nucleic acid sequence encoding the fusion protein are present in two separate nucleic acids.

In another aspect, the present invention provides a population of purified Fc-EPO fusion proteins suitable for administration to a mammal. In a preferred embodiment, the Fc-EPO fusion proteins include an Fc portion toward the N-terminus of the Fc-EPO fusion proteins and an erythropoietin portion towards the C-terminus of the Fc-EPO fusion proteins. In a more preferred embodiment, the population of purified Fc-EPO fusion proteins is highly sialylated, i.e., having an average of 11-28 sialic acid residues per purified Fc-EPO fusion protein. Preferred highly sialylated populations of Fc-EPO fusion proteins have an average of 13-28, 15-28, 17-28, 19-28, or 21-28 sialic acid residues per purified Fc-EPO fusion protein. For example, one preferred highly sialylated population of Fc-EPO fusion proteins has an average of 20 to 22 sialic acid residues per purified Fc-EPO fusion protein. In a preferred embodiment, the purified Fc-EPO fusion proteins are synthesized in a BHK cell. In one embodiment, the BHK cell is adapted for growth in suspension. In another embodiment, the BHK cell is adapted for growth in a protein-free medium. In yet another embodiment, the BHK cell is adapted for growth in a protein-free medium and in suspension. The highly sialylated population of purified Fc-EPO fusion proteins provided by the present invention has a longer serum half-life compared to a population of corresponding Fc-EPO fusion proteins produced in cells such as, for example, NS/0, PerC6, or 293 cells. In accordance with the present invention, the Fc portion and the erythropoietin portion of the purified Fc-EPO fusion proteins can contain one or more mutations or modifications as described herein, providing a prolonged serum half-life and an increased in vivo potency with effects that are additive or synergistic with enhanced sialylation.

The present invention also provides a pharmaceutical composition containing the highly sialylated population of purified Fc-EPO fusion proteins as described herein. A preferred pharmaceutical composition further includes a pharmaceutically acceptable carrier. The present invention further provides a method of treating a mammal including administering to the mammal the pharmaceutical composition containing the highly sialylated population of purified Fc-EPO fusion proteins. In a preferred embodiment, the pharmaceutical composition is administered fewer than three times per week (e.g., twice weekly, weekly, or not more than once every ten days, such as once every two weeks, once per month or once every two months).

BRIEF DESCRIPTION OF THE DRAWINGS

FIGS. 1A and 1B depict an alignment of the amino acid sequences of constant regions of human IgG1, IgG2 and IgG4. Amino acids 118-447 of IgG1 correspond to SEQ ID NO:22. Amino acids 118-443 of IgG2 correspond to SEQ ID NO:23. Amino acids 118-444 of IgG4 correspond to SEQ ID NO:24.

FIG. 7 depicts an exemplary nucleic acid sequence (SEQ ID NO:2) encoding a mature Fc-EPO protein.

DETAILED DESCRIPTION OF THE INVENTION

Figure 2:
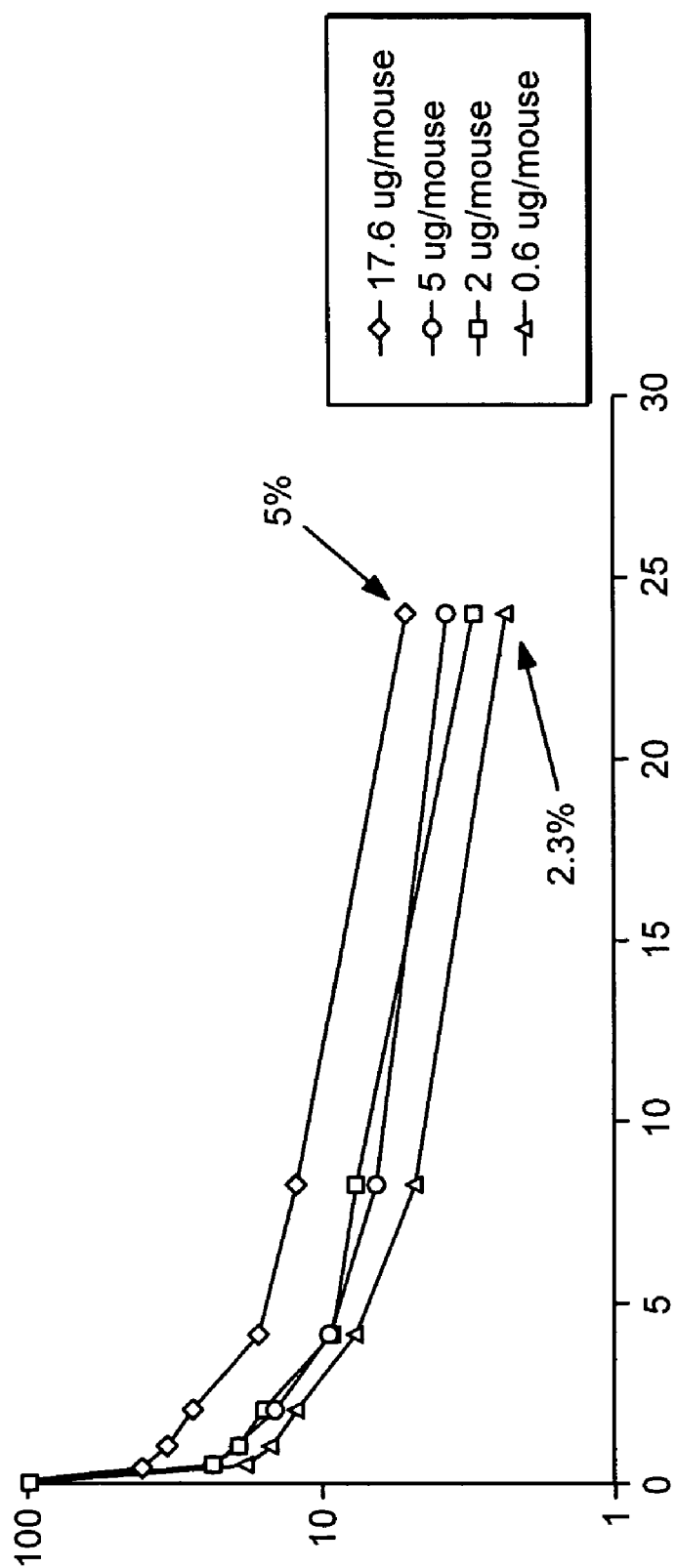
FIG. 2 depicts a pharmacokinetics experiment in mice showing a correlation between Fc-EPO dose and amount of decrease in the Fc-EPO serum concentrations during the alpha phase. In this experiment an undersialylated Fc-EPO variant synthesized in NS/0 cells was used.

The present invention provides an Fc-EPO fusion protein with improved pharmacokinetics. Specifically, the Fc-EPO protein provided by the present invention has a prolonged serum half-life and increased in vivo potency. In one aspect, the present invention provides an Fc-EPO fusion protein synthesized in BHK cells. The Fc-EPO fusion proteins synthesized in BHK cells have demonstrated dramatically prolonged serum half-lives and increased in vivo potency when compared to corresponding Fc-EPO fusion proteins produced in other cell lines, such as, for example, NS/0, PerC6, or 293 cells. In another aspect, the present invention provides a population of highly sialylated Fc-EPO fusion proteins. The population of highly sialylated Fc-EPO fusion proteins has a longer serum half-life compared to a population of corresponding Fc-EPO fusion proteins with lower levels of sialylation. In accordance with the present invention, an Fc-EPO fusion protein can contain amino acid modifications in the Fc portion that extend serum half-life of an Fc fusion protein, such as by substantially decreasing or eliminating Fc receptor binding activity, or modifications that reduce complement fixing activity. In addition, the Fc-EPO fusion protein can also contain amino acid modifications in the erythropoietin portion that reduce EPO receptor-mediated endocytosis or increase the biological activity of erythropoietin.

Fc-EPO Fusion Protein

"Fc-EPO fusion protein" as used herein refers to a protein comprising a polypeptide having at least two portions, namely, an Fc portion and an erythropoietin portion, that are not normally present in the same polypeptide. In preferred embodiments of the present invention, the polypeptides having an Fc portion and an erythropoietin portion form homodimers; accordingly, an Fc-EPO fusion protein is generally a dimeric protein held together by one or more disulfide bonds, each polypeptide chain containing an Fc portion and an erythropoietin portion. However, an Fc-EPO fusion protein of the present invention can have any configuration allowing erythropoietin portions to stably associate with Fc portions while maintaining erythropoietin activity. For example, such configurations include, but are not limited to, a single polypeptide containing two Fc portions and two erythropoietin portions, a single polypeptide containing two Fc portions and one erythropoietin portion, a heterodimeric protein including one polypeptide containing an Fc portion and an erythropoietin portion and another polypeptide containing an Fc portion, and other suitable configurations.

The erythropoietin portion can be directly or indirectly linked to the Fc portion in various configurations. In one embodiment, the erythropoietin portion is directly linked to the Fc portion through a covalent bond. For example, the erythropoietin portion can be fused directly to the Fc portion at either its C-terminus or its N-terminus. In one embodiment, the C-terminus of the Fc portion is fused to the N-terminus of the erythropoietin portion, i.e., $N_{term}$-Fc-$C_{term}$-$N_{term}$-EPO-$C_{term}$. In this configuration, the Fc portion is towards the N-terminus of the Fc-EPO fusion protein and the erythropoietin portion is towards the C-terminus. In another embodiment, the C-terminus of erythropoietin is fused to the N-terminus of the Fc portion, i.e., $N_{term}$-EPO-$C_{term}$-$N_{term}$-Fc-$C_{term}$. In this configuration, the erythropoietin portion is towards the N-terminus of the Fc-EPO fusion protein and the Fc portion is towards the C-terminus.

In other embodiments, the erythropoietin portion is indirectly linked to the Fc portion. For example, the Fc-EPO fusion protein can include a linker (L) between the Fc portion and the erythropoietin portion. Similar to the direct fusion, the erythropoietin portion is preferably fused to the C-terminus of the Fc portion through a linker, i.e., $N_{term}$-Fc-$C_{term}$-L-$N_{term}$-EPO-$C_{term}$. Thus, the Fc portion is towards the N-terminus of the Fc-EPO fusion protein and separated by a linker from the erythropoietin portion towards the C-terminus.

Alternatively, the erythropoietin portion can be fused to the N-terminus of the Fc portion through a linker, i.e., $N_{term}$-EPO-$C_{term}$-L-$N_{term}$-Fc-$C_{term}$.

Fc Portion

Figure 1A:
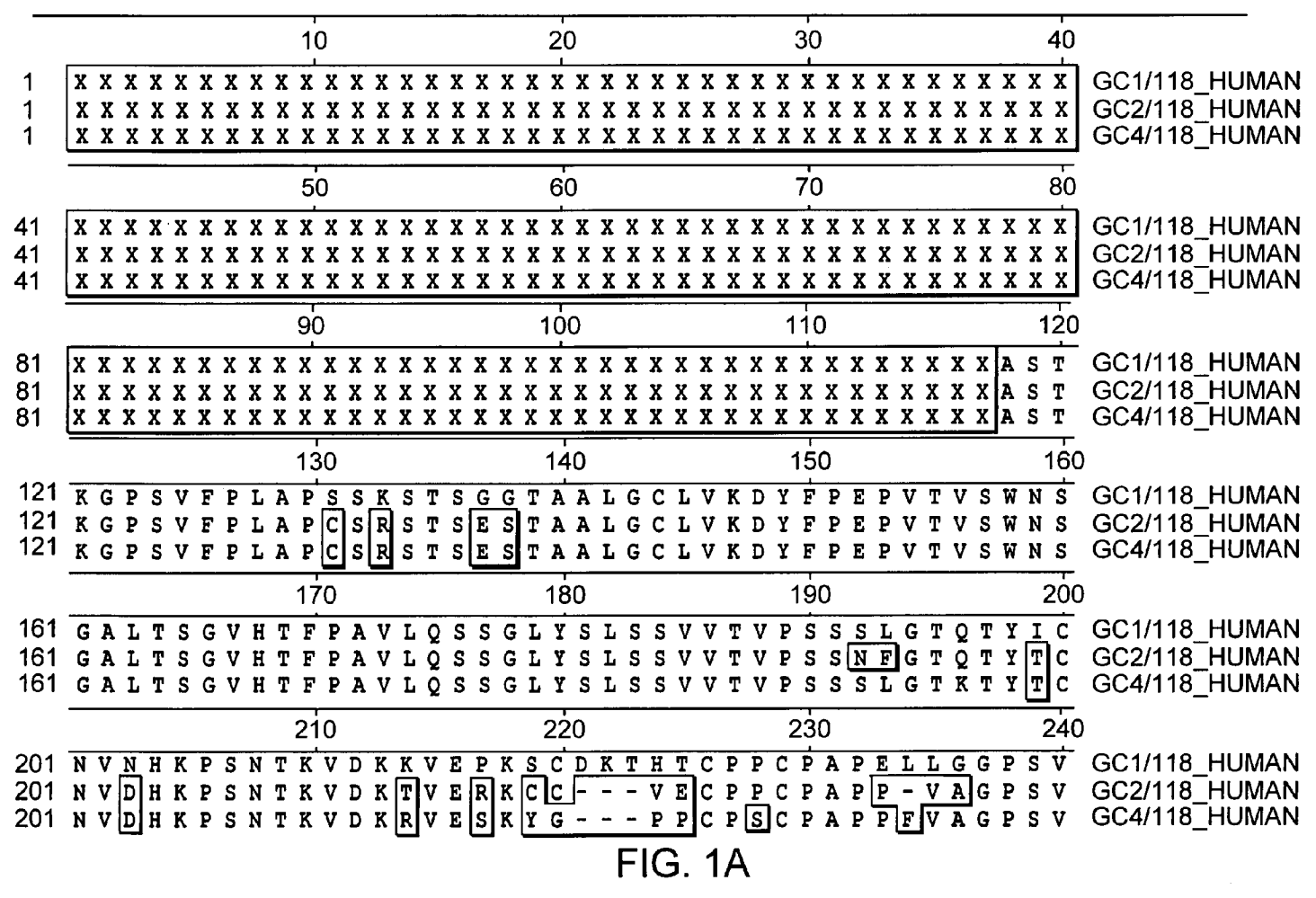

As used herein, "Fc portion" encompasses domains derived from the constant region of an immunoglobulin, preferably a human immunoglobulin, including a fragment, analog, variant, mutant or derivative of the constant region. Suitable immunoglobulins include IgG1, IgG2, IgG3, IgG4, and other classes. The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in combination. A sequence alignment of the constant regions of human IgG1, IgG2 and IgG4 is shown in FIGS. 1A and 1B. According to Paul, (1999) *Fundamental Immunology* 4$^{th}$ Ed., Lippincott-Raven, CH1 domain includes amino acids 118-215; hinge region includes amino acids 216-230; CH2 domain includes amino acids 231-340; and CH3 domain includes amino acids 341-447 (the amino acid positions are based on IgG1 sequence). The hinge region joins the CH1 domain to the CH2 and CH3 domains.

In the present invention, the Fc portion typically includes at least a CH2 domain. For example, the Fc portion can include hinge-CH2-CH3. Alternatively, the Fc portion can include all or a portion of the hinge region, the CH2 domain and/or the CH3 domain.

The constant region of an immunoglobulin is responsible for many important antibody functions including Fc receptor (FcR) binding and complement fixation. There are five major classes of heavy chain constant region, classified as IgA, IgG, IgD, IgE, IgM, each with characteristic effector functions designated by isotype. For example, IgG is separated into four γ subclasses: γ1, γ2, γ3, and γ4, also known as IgG1, IgG2, IgG3, and IgG4, respectively.

IgG molecules interact with multiple classes of cellular receptors including three classes of Fcγ receptors (FcγR) specific for the IgG class of antibody, namely FcγRI, FcγRII, and FcγRIII. The important sequences for the binding of IgG to the FcγR receptors have been reported to be located in the CH2 and CH3 domains. The serum half-life of an antibody is influenced by the ability of that antibody to bind to an Fc receptor (FcR). Similarly, the serum half-life of immunoglobulin fusion proteins is also influenced by the ability to bind to such receptors (Gillies S D et al., (1999) *Cancer Res.* 59:2159-66). Compared to those of IgG1, CH2 and CH3 domains of IgG2 and IgG4 have biochemically undetectable or reduced binding affinity to Fc receptors. It has been reported that immunoglobulin fusion proteins containing CH2 and CH3 domains of IgG2 or IgG4 had longer serum half-lives compared to the corresponding fusion proteins containing CH2 and CH3 domains of IgG1 (U.S. Pat. No. 5,541, 087; Lo et al., (1998) *Protein Engineering*, 11:495-500). Accordingly, preferred CH2 and CH3 domains for the present invention are derived from an antibody isotype with reduced receptor binding affinity and effector functions, such as, for example, IgG2 or IgG4. More preferred CH2 and CH3 domains are derived from IgG2.

The hinge region is normally located C-terminal to the CH1 domain of the heavy chain constant region. In the IgG isotypes, disulfide bonds typically occur within this hinge region, permitting the final tetrameric molecule to form. This region is dominated by prolines, serines and threonines. When included in the present invention, the hinge region is typically at least homologous to the naturally-occurring immunoglobulin region that includes the cysteine residues to form disulfide bonds linking the two Fc moieties. Representative sequences of hinge regions for human and mouse immunoglobulins can be found in Borrebaeck, C. A. K., ed., (1992) *ANTIBODY ENGINEERING, A PRACTICAL GUIDE*, W. H. Freeman and Co. Suitable hinge regions for the present invention can be derived from IgG1, IgG2, IgG3, IgG4, and other immunoglobulin classes. The IgG1 hinge region has three cysteines, two of which are involved in disulfide bonds between the two heavy chains of the immunoglobulin. These same cysteines permit efficient and consistent disulfide bonding formation between Fc portions. Therefore, a preferred hinge region of the present invention is derived from IgG1, more preferably from human IgG1. In some embodiments, the first cysteine within the human IgG1 hinge region is mutated to another amino acid, preferably serine. The IgG2 isotype hinge region has four disulfide bonds that tend to promote oligomerization and possibly incorrect disulfide bonding during secretion in recombinant systems. A suitable hinge region can be derived from an IgG2 hinge; the first two cysteines are each preferably mutated to another amino acid. The hinge region of IgG4 is known to form interchain disulfide bonds inefficiently. However, a suitable hinge region for the present invention can be derived from the IgG4 hinge region, preferably containing a mutation that enhances correct formation of disulfide bonds between heavy chain-derived moieties (Angal S, et al. (1993) *Mol. Immunol.*, 30:105-8).

In accordance with the present invention, the Fc portion can contain CH2 and/or CH3 domains and a hinge region that are derived from different antibody isotypes, i.e., a hybrid Fc portion. For example, in one embodiment, the Fc portion contains CH2 and/or CH3 domains derived from IgG2 or IgG4 and a mutant hinge region derived from IgG1. Alternatively, a mutant hinge region from another IgG subclass is used in a hybrid Fc portion. For example, a mutant form of the IgG4 hinge that allows efficient disulfide bonding between the two heavy chains can be used. A mutant hinge can also be derived from an IgG2 hinge in which the first two cysteines are each mutated to another amino acid. Such hybrid Fc portions facilitate high-level expression and improve the correct assembly of the Fc-EPO fusion proteins. Assembly of such hybrid Fc portions has been described in U.S. Patent Publication No. 20030044423 (i.e., U.S. application Ser. No. 10/093,958), the disclosure of which is hereby incorporated by reference.

In some embodiments, the Fc portion contains amino acid modifications that generally extend the serum half-life of an Fc fusion protein. Such amino acid modifications include mutations substantially decreasing or eliminating Fc receptor binding or complement fixing activity. For example, the glycosylation site within the Fc portion of an immunoglobulin heavy chain can be removed. In IgG1, the glycosylation site is Asn297. In other immunoglobulin isotypes, the glycosylation site corresponds to Asn297 of IgG1. For example, in IgG2 and IgG4, the glycosylation site is the asparagine within the amino acid sequence Gln-Phe-Asn-Ser (SEQ ID NO:16). Accordingly, a mutation of Asn297 of IgG1 removes the glycosylation site in an Fc portion derived from IgG1. In one embodiment, Asn297 is replaced with Gln. Similarly, in IgG2 or IgG4, a mutation of asparagine within the amino acid sequence Gln-Phe-Asn-Ser (SEQ ID NO:16) removes the glycosylation site in an Fc portion derived from IgG2 or IgG4 heavy chain. In one the asparagine is replaced with a glutamine. In other embodiments, the phenylalanine within the amino acid sequence Gln-Phe-Asn-Ser (SEQ ID NO:16) is further mutated to eliminate a potential non-self T-cell epitope resulting from asparagine mutation. For example, the amino acid sequence Gln-Phe-Asn-Ser (SEQ ID NO:16) within an IgG2 or IgG4 heavy chain can be replaced with a Gln-Ala-Gln-Ser (SEQ ID NO:17) amino acid sequence.

It has also been observed that alteration of amino acids near the junction of the Fc portion and the non-Fc portion can dramatically increase the serum half-life of the Fc fusion protein (PCT publication WO 01/58957, the disclosure of which is hereby incorporated by reference). Accordingly, the junction region of an Fc-EPO fusion protein of the present invention can contain alterations that, relative to the naturally-occurring sequences of an immunoglobulin heavy chain and erythropoietin, preferably lie within about 10 amino acids of the junction point. These amino acid changes can cause an increase in hydrophobicity by, for example, changing the C-terminal lysine of the Fc portion to a hydrophobic amino acid such as alanine or leucine.

In other embodiments, the Fc portion contains amino acid alterations of the Leu-Ser-Leu-Ser (SEQ ID NO:20) segment near the C-terminus of the Fc portion of an immunoglobulin heavy chain. The amino acid substitutions of the Leu-Ser-Leu-Ser (SEQ ID NO:20) segment eliminate potential junctional T-cell epitopes. In one embodiment, the Leu-Ser-Leu-Ser (SEQ ID NO:20)amino acid sequence near the C-terminus of the Fc portion is replaced with an Ala-Thr-Ala-Thr (SEQ ID NO:21) amino acid sequence. In other embodiments, the amino acids within the Leu-Ser-Leu-Ser (SEQ ID NO:20) segment are replaced with other amino acids such as glycine or proline. Detailed methods of generating amino acid substitutions of the Leu-Ser-Leu-Ser (SEQ ID NO:20) segment near the C-terminus of an IgG1, IgG2, IgG3, IgG4, or other immunoglobulin class molecule have been described in U.S. Patent Publication No. 20030166877 (i.e., U.S. patent application Ser. No. 10/112,582), the disclosure of which is hereby incorporated by reference.

Erythropoietin Portion

As used herein, "erythropoietin portion" encompasses wild-type or naturally-occurring erythropoietin from human and other species, recombinant erythropoietin, and erythropoietin-like molecules, including biologically-active erythropoietin fragments, analogs, variants, mutants or derivatives of erythropoietin.

Wild-type or naturally-occurring erythropoietin is a 34 KD glycoprotein hormone that stimulates the growth and development of red blood cells from erythropoietin precursor cells. Wild-type or naturally-occurring erythropoietin is produced in the kidney in response to hypoxia (e.g., red blood cell loss due to anemia) and regulates red blood cell growth and differentiation through interaction with its cognate cellular receptor. Wild-type or naturally-occurring erythropoietin can be isolated and purified from blood (Miyake T., et al., (1977) *J. Biol. Chem.*, 252:5558-5564), or plasma (Goldwasser, E., et al., (1971) *Proc. Natl. Acad. Sci. U.S.A.*, 68:697-698), or urine.

Recombinant or chemically-synthesized erythropoietin can be produced using techniques well known to those of skill in the art. Two forms of recombinant human erythropoietin (rHuEPO) are commercially available: EPOGEN® from Amgen and PROCRIT® from Johnson & Johnson.

As used herein, the biological activity of erythropoietin is defined as the ability to stimulate cell proliferation through interaction with the erythropoietin receptor. The functional assay of erythropoietin can be conducted in vitro or in vivo. For example, the in vitro activity of erythropoietin can be tested in a cell-based assay. Specifically, the erythropoietin activity can be determined based on a TF-1 cell proliferation assay. TF-1 cells express EPO receptors. The proliferation of TF-1 cells, which is determined by the incorporation of tritiated thymidine, is a function of erythropoietin activity (Hammerlling et al., (1996) *J. Pharmaceutical and Biomedical Analysis*, 14:1455; Kitamura et al., (1989) *J. Cellular Physiol.*, 140:323). The in vitro cell-based assay is described in more detail in Example 6. In vivo assays are typically conducted in animal models, such as, for example, mice and rats. Examples of in vivo assays include, but are not limited to, hematocrit (HCT) assays and reticulocyte assays. HCT assays measure the volume of red blood cells from a blood sample taken from an erythropoietin-treated animal, and are performed by centrifuging blood in capillary tubes and measuring the fraction of the total volume occupied by sedimented red blood cells. The in vivo HCT assay is described in more detail in Example 8. Reticulocyte assays measure new red blood cells, also known as reticulocytes, that have recently differentiated from precursor cells and still have remnants of nucleic acids characteristic of the precursor cells. Reticulocytes are measured by sorting red blood cells in a flow cytometer after staining with a nucleic acid-staining dye such as acridine orange or thiazole orange, and counting the positively-stained reticulocyte fraction.

A biologically-active or functionally-active erythropoietin-like molecule typically shares substantial amino acid sequence similarity or identity (e.g., at least about 55%, about 65%, about 75% identity, typically at least about 80% and most typically about 90-95% identity) with the corresponding sequences of wild-type, or naturally-occurring, erythropoietin and possesses one or more of the functions of wild-type erythropoietin thereof.

Thus, erythropoietin of the present invention is understood to specifically include erythropoietin polypeptides having amino acid sequences analogous to the sequence of wild-type erythropoietin. Such proteins are defined herein as erythropoietin analogs. An "analog" is defined herein to mean an amino acid sequence with sufficient similarity to the amino acid sequence of wild-type erythropoietin to possess the biological activity of the protein. For example, an analog of erythropoietin can contain one or more amino acid changes in the amino acid sequence of wild-type erythropoietin, yet possesses, e.g., the ability to stimulate red blood cell production or maturation. Examples of such amino acid changes include additions, deletions or substitutions of amino acid residues. Erythropoietin of the present invention also encompasses mutant proteins that exhibit greater or lesser biological activity than wild-type erythropoietin, such as described in U.S. Pat. No. 5,614,184.

Erythropoietin of the present invention also encompasses biologically active fragments of erythropoietin. Such fragments can include only a part of the full-length amino acid sequence of erythropoietin yet possess biological activity. As used herein, a "biologically active fragment" means a fragment that can exert a biological effect similar to the full length protein. Such fragments can be produced by amino- and carboxy-terminal deletions as well as internal deletions. They also include truncated and hybrid forms of erythropoietin. "Truncated" forms are shorter versions of erythropoietin, for example, with amino terminal, or carboxyl terminal residues removed.

Variations in Erythropoietin Sequence

The amino acid modifications can be introduced into the erythropoietin portion of the present invention to reduce binding affinity to the EPO receptor; to enhance protein stability; to enhance adoption of a correct, active conformation; to enhance pharmacokinetic properties; to enhance synthesis; or to provide other advantageous features. For example, EPO receptor-mediated endocytosis is determined by the binding affinity between erythropoietin and EPO receptor. The three-dimensional structure of a complex of human erythropoietin and EPO receptor demonstrates that erythropoietin binding to its receptor is dominated by positive charges on the surface of erythropoietin and negative charges on the EPO receptor. Syed et al., (1998) *Nature,* 395:511. To reduce the on-rate of binding, mutations can be introduced to replace positively charged amino acids that lie near the erythropoietin-EPO receptor contact surface. For example, in one embodiment, one or both of Arg131 and Arg139 of human erythropoietin can be replaced (the amino acid numbering of EPO sequences being based on mature human EPO). Preferably, Arg131 and Arg139 are replaced with glutamic acid, aspartic acid, or other non-positively charged amino acids. Mutations can be introduced in erythropoietin of other species to replace amino acids corresponding to Arg131 and Arg139 of human erythropoietin. However, to preserve EPO biological activity, those residues which are in the center of the EPO-EPO receptor interaction should be avoided when making alterations in the EPO amino acid sequence.

Alternatively, one can empirically determine those regions or positions which would tolerate amino acid substitutions by alanine scanning mutagenesis (Cunningham et al., (1989) *Science,* 244, 1081-1085). In this method, selected amino acid residues are individually substituted with a neutral amino acid (e.g., alanine) in order to determine the effects on biological activity.

In one embodiment, the erythropoietin portion contains at least one of the following mutations: His32→Gly and/or Ser34→Arg, and Pro90→Ala. In other embodiments, cysteine substitutions are introduced in erythropoietin to alter patterns of cysteine-cysteine disulfide bonds, resulting in new disulfide bond formation ("NDS mutations"). Naturally-occurring human erythropoietin, which appears to be unique among mammalian erythropoietins, has exactly four cysteines at positions 7, 29, 33, and 161 that form two disulfide bonds. One or more of these cysteine residues of the erythropoietin portion can be altered. To generate an altered disulfide bond, one cysteine residue is mutated to a structurally compatible amino acid such as alanine or serine, and a second amino acid that is nearby in the three-dimensional structure is mutated to cysteine. For example, one of amino acids $Gln_{86}$, $Pro_{87}$, $Trp_{88}$, $Glu_{89}$, and $Leu_{91}$, can be replaced by Cys. If $Trp_{88}$ is replaced by Cys and $Cys_{33}$ is replaced with another amino acid, the erythropoietin portion will form a $Cys_{29}$-$Cys_{88}$ disulfide bond that is not found in human EPO. This bond results in a fusion protein that has greater activity than a fusion protein with a typical $Cys_{29}$-$Cys_{33}$ disulfide bond. In addition, the $Cys_{29}$-$Cys_{88}$ fusion protein shows a pronounced increase in activity, compared to the $Cys_{29}$-$Cys_{33}$ fusion protein, in the presence of other mutations in the erythropoietin portion of the fusion protein. Accordingly, in one embodiment of the present invention, the erythropoietin portion includes at least one of the following amino acid substitutions: a non-cysteine residue at position 29, a non-cysteine residue at position 33, a cysteine residue at position 88, and a cysteine residue at position 139. In one embodiment, the erythropoietin portion contains cysteines at positions 7, 29, 88, and 161. In another embodiment, the erythropoietin portion further contains one or more of the following substitutions: $His_{32}$→Gly, $Cys_{33}$→Pro, and $Pro_{90}$→Ala. In an alternative embodiment, an entirely new disulfide bond is added to the protein by mutating two amino acids to cysteines. To compensate for possible strains in the structure that the Cys mutations might cause, in a preferred Cys-engineered embodiment of this invention, the erythropoietin portion further contains mutations designed to alleviate these potential strains.

Further embodiments relating to cysteine substitutions are described in PCT publication WO 01/36489 (i.e., U.S. application Ser. No. 09/708,506), the disclosure of which is hereby incorporated by reference.

Methods for introducing mutations in erythropoietin are well known in the art. For example, mutations can be introduced by site-directed mutagenesis techniques. It is important to note that a wide variety of site-directed mutagenesis techniques are available and can be used as alternatives to achieve similar results. Other techniques include, but are not limited to, random and semi-random mutagenesis.

Linker

The Fc-EPO fusion proteins according to this invention can include a linker between the Fc portion and the erythropoietin portion. A fusion protein with a linker may have improved properties, such as increased biological activity. A linker generally contains between 1 and 25 amino acids (e.g., between 5 and 25 or between 10 and 20 amino acids). The linker can be designed to include no protease cleavage site. Furthermore, the linker can contain an N-linked or an O-linked glycosylation site to sterically inhibit proteolysis. Accordingly, in one embodiment, the linker contains an Asn-Ala-Thr amino acid sequence.

Additional suitable linkers are disclosed in Robinson et al., (1998), *Proc. Natl. Acad. Sci. USA;* 95, 5929; and U.S. application Ser. No. 09/708,506.

Glycosylation

Naturally-occurring human erythropoietin and recombinant erythropoietin expressed in mammalian cells contain three N-linked and one O-linked oligosaccharide chains. N-linked glycosylation occurs at asparagine residues located at positions 24, 38 and 83, while O-linked glycosylation occurs at a serine residue located at position 126 (Lai et al., (1986) *J. Biol. Chem.,* 261:3116; Broudy et al., (1988) *Arch. Biochem. Biophys.,* 265:329). The oligosaccharide chains have been shown to be modified with terminal sialic acid residues. N-linked chains typically have up to four sialic acids per chain and O-linked chains have up to two sialic acids. An erythropoietin polypeptide can therefore accommodate up to a total of 14 sialic acids.

Sialic acid is the terminal sugar on N-linked or O-linked oligosaccharides. The extent of sialylation is variable from site to site, protein to protein, and can depend on cell culture conditions, cell types, and particular cell clones that are used. It has been found that the Fc-EPO fusion protein of the present invention synthesized in BHK cells is highly sialylated. It has also been found that the extent of sialylation of Fc-EPO fusion protein can be further enhanced by adapting the BHK cells for growth in protein-free media, in suspension, or in protein-free media and in suspension. Certain other commonly used cell lines, such as NS/0, PerC6, or 293 cells fail to produce highly sialylated Fc-EPO fusion protein under standard culture conditions. The extent of sialylation of the Fc-EPO fusion protein produced from different cell lines can be determined by isoelectric focusing (IEF) gel electrophoresis by virtue of their highly negatively charged sialic acid residues; the details of IEF gel electrophoresis are described in Example 5B. The extent of sialylation of the Fc-EPO fusion protein produced in different cell lines can also be qualitatively confirmed by lectin-binding studies using methods familiar to those skilled in the art. An example of a lectin-binding assay is described in Example 5B.

Typically, a population of highly sialylated purified Fc-EPO fusion proteins of the present invention has an average of 11-28 sialic acid residues per purified Fc-EPO fusion protein. Preferred highly sialylated populations of Fc-EPO fusion proteins have an average of 13-28, 15-28, 17-28, 19-28, or 21-28 sialic acid residues per purified Fc-EPO fusion protein. For example, one preferred highly sialylated population of Fc-EPO fusion proteins has an average of 20 to 22 sialic acid residues per purified Fc-EPO fusion protein. Another preferred population of Fc-EPO fusion proteins has an average of 23-28 sialic acid residues per purified Fc-EPO fusion protein.

Pharmacokinetics of the Sialylated Fc-EPO Fusion Protein

One of the most important factors determining the in vivo biological activity of erythropoiesis-stimulating agents is the length of time that the serum concentration of the protein remains above the threshold necessary for erythropoiesis, which is determined by the pharmacokinetics of the erythropoiesis-stimulating agents. The pharmacokinetic profile of the highly sialylated Fc-EPO fusion protein is distinct from that of naturally-occurring or recombinant erythropoietin. The major difference is that the highly sialylated Fc-EPO fusion protein has much longer serum half-life and slower clearance leading to increased in vivo biological potency. Without wishing to be bound by theory, sialic acid residues are believed to increase the negative charges on an erythropoietin molecule resulting in decreased on-rate for negatively-charged EPO receptor binding and decreased EPO receptor mediated endocytosis, lengthening the serum half-life. Furthermore, sialic acids also prevent erythropoietin proteins from being endocytosed by the asialoglycoprotein receptors that bind glycoproteins with exposed galactose residues.

In general, most pharmacokinetic profiles of a therapeutic molecule such as erythropoietin show an initial drop in serum concentration (an alpha phase), followed by a more gradual decline (a beta phase) following administration.

Factors Influencing the Alpha Phase

According to small-molecule pharmacokinetic theory, the alpha phase defines a volume of distribution that describes how a molecule partitions into compartments outside the blood. The drop observed in the alpha phase varies widely for different Fc-EPO fusion proteins synthesized in different cell lines. In theory, the difference could be due to variation in the volume of distribution, or due to variations in inter-compartment trafficking. However, it has been observed that there is a correlation between the extent of sialylation and the pharmacokinetic behavior of the Fc-EPO proteins in mice. For example, the Fc-EPO fusion proteins synthesized in BHK cells are highly sialylated and show the best pharmacokinetic profile. The Fc-EPO fusion proteins synthesized in NS/0 cells are somewhat sialylated and have an intermediate pharmacokinetic profile. The Fc-EPO fusion proteins synthesized in 293 and PerC6 cells have little or no sialylation and have a poor pharmacokinetic profile characterized by about a 100-fold drop in serum concentration in the first 30 minutes. Therefore, a key factor that influences the alpha phase of a particular Fc-EPO fusion protein is the distribution of glycosylation species and the level of sialylation. The Fc-EPO fusion proteins that are undersialylated disappear rapidly.

In addition, as shown in FIG. 2, the extent of the drop in the Fc-EPO serum concentrations during the alpha phase varies according to the dose, indicating that this behavior is saturable and most likely receptor-mediated. It is possible that the receptor mediating the alpha phase drop is neither EPO receptor nor Fc receptor, but another receptor such as the asialoglycoprotein receptor. Aranesp® has reduced binding affinity to the EPO receptors compared to normal human erythropoietin because Aranesp® has increased negative charges as a result of additional N-linked glycosylation sites. However, Aranesp® and normal human erythropoietin show similar drops during alpha phases. In addition, since generally the number of the EPO receptors on the cell surface of an erythroid progenitor cell is only approximately 200, these receptors would be completely saturated at much lower doses of erythropoietin than those used in FIG. 2. Fc receptors are perhaps unlikely to mediate the dramatic drop in the alpha phase because Fc-EPO fusion proteins with a mutation eliminating the glycosylation site, e.g., a mutation of amino acid corresponding to Asn297 of IgG1, can still show a steep drop in the alpha phase. In addition, although IgG2 CH2 regions, when not aggregated, generally do not bind to Fc receptors, the Fc-EPO proteins containing IgG2 CH2 regions still show a significant drop during alpha phase.

Without wishing to be bound by theory, the drop of the serum concentration of an Fc-EPO fusion protein during alpha phase may be mediated by asialoglycoprotein-receptors via asialoglycoprotein-receptor-mediated endocytosis. Undersialylated Fc-EPO fusion proteins contain exposed galactose residues that can be bound by the asialoglycoprotein receptor resulting in asialoglycoprotein-receptor-mediated endocytosis. As a result, undersialylated Fc-EPO fusion proteins can disappear rapidly.

Factors Influencing the Beta Phase

The drop of the serum concentrations of the Fc-EPO fusion proteins in the beta phase is less steep compared to the drop in the alpha phase. For example, in mice, between 8 and 24 hours following administration, a 2- to 3-fold drop in the serum concentrations of the Fc-EPO fusion proteins is observed. The difference in the drop during the beta phase is also less drastic between different Fc-EPO proteins synthesized in different cell lines. However, like in the alpha phase, the extent of sialylation correlates with the pharmacokinetic behavior in the beta phase. For example, the Fc-EPO fusion proteins synthesized in BHK cells have a significantly improved beta phase compared to otherwise identical Fc-EPO proteins synthesized in NS/0 cells. EPO receptor-mediated endocytosis appears to be at least partly responsible for the drop in the serum concentration of the Fc-EPO fusion proteins during beta phase. Aranesp®, which has reduced binding affinity for EPO receptors compared to normal human erythropoietin, has a significantly improved beta phase compared to normal human erythropoietin, despite similar alpha phase profiles.

The Fc-EPO fusion proteins of the invention generally exhibit an improved beta phase compared to naturally-occurring or recombinant erythropoietin, indicating that the addition of the Fc portion significantly slows down the decline of the serum concentration during the beta phase. It has also been observed that certain amino acid modifications in the Fc portion or in the erythropoietin portion can significantly improve the beta phase. For example, mutations eliminating the glycosylation site in the Fc portion improve the beta phase of Fc-EPO fusion proteins. Mutations increasing the stability of the erythropoietin portion, e.g., mutations engineering disulfide bonds (for example, NDS mutations) in the erythropoietin portion, significantly improve the beta phase of the Fc-EPO fusion protein. Generally, an improved beta phase extends the terminal serum half-life of an Fc-EPO fusion protein.

Routes of Elimination of Fc-EPO Fusion Proteins

Figure 3:
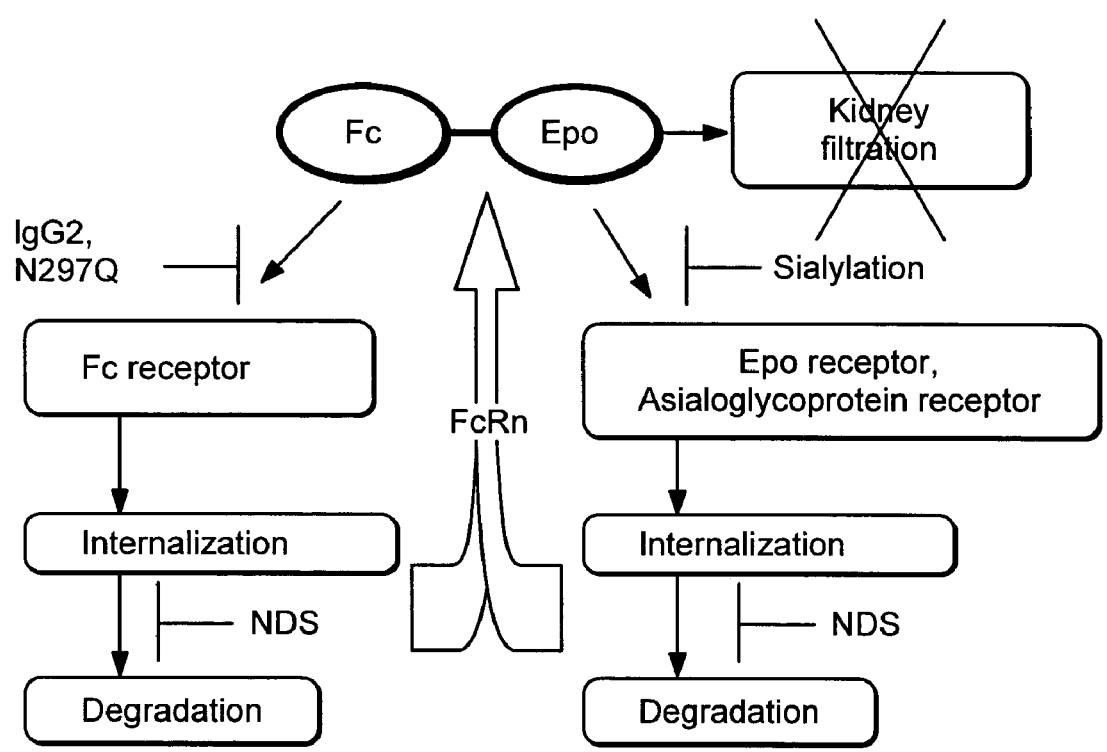
FIG. 3 depicts potential routes of elimination of Fc-EPO fusion proteins and modifications to the fusion protein that potentially modulate these routes.

There are several possible routes of elimination of an erythropoietin protein molecule from the body. A wild-type or naturally-occurring erythropoietin protein molecule can be eliminated from the body by kidney filtration and receptor-mediated endocytosis. Endocytosed erythropoietin is efficiently degraded. As depicted in FIG. 3, the addition of an Fc portion to the erythropoietin portion is expected to essentially abolish the excretion of the Fc-EPO fusion protein through the kidney. As a result, receptor-mediated endocytosis is the major route of elimination of an Fc-EPO fusion protein. Furthermore, the addition of an Fc portion to the erythropoietin portion is also expected to reduce degradation after internalization, because the FcRn endosomal receptors are expected to recycle the fusion protein back out of the cell.

In principle, at least three types of receptors can mediate the clearance of the Fc-EPO fusion protein, namely, Fc-receptor, EPO receptor, and asialoglycoprotein receptor. Clearance of the Fc-EPO fusion protein through the Fc receptor should be significantly reduced by use of an IgG2-derived CH2 domain instead of an IgG1-derived CH2 in the Fc portion. IgG2-derived CH2 domains have about a 100-fold lower affinity for FcγRI, which has the highest affinity for IgGs, compared to IgG1-derived CH2 domains. The interaction between the IgG2-derived CH2 and FcγRI is undetectable in most binding assays. However, the residual FcγR-binding activity of the IgG2-derived CH2 domain may still play a role in clearance of Fc-EPO fusion protein because the asparagine mutation eliminating the glycosylation site in the CH2 domain further reduces Fc-receptor binding and improves the pharmacokinetics of the Fc-EPO fusion protein.

The NDS mutations have the effect of stabilizing the erythropoietin structure and, as a result, are expected to reduce degradation of the Fc-EPO fusion protein after internalization. The Fc-EPO fusion proteins containing the NDS mutations have improved pharmacokinetic properties and increased serum half-life.

Sialylation increases the negative charges of Fc-EPO fusion proteins, reducing the binding affinity of the Fc-EPO fusion protein for the EPO receptor. Sialylation also reduces the number of exposed galactose residues on the Fc-EPO fusion protein, reducing binding affinity of the Fc-EPO fusion proteins for the asialoglycoprotein receptors. Accordingly, as depicted in FIG. 3, sialylation reduces both EPO receptor-mediated endocytosis and asialoglycoprotein receptor-mediated endocytosis. Highly sialylated Fc-EPO fusion proteins therefore have dramatically slowed clearance rates resulting in significantly increased serum half-lives.

The addition of an Fc portion, the alterations of Fc and erythropoietin portions, and sialylation each reduce the clearance of Fc-EPO fusion proteins. The combined effects on clearance and serum half-life are additive or multiplicative.

In vitro Activity and in vivo Potency of the Fc-EPO Fusion Protein

The in vitro activity of Fc-EPO proteins can be tested in a cell-based assay. Specifically, the interaction between Fc-EPO and EPO receptor can be determined based on the TF-1 cell proliferation assay. The TF-1 cells express EPO receptors, therefore, the proliferation of TF-1 cells, which is determined by the incorporation of tritiated thymidine, is a function of erythropoietin activity (Hammerlling et al., (1996) *J. Pharmaceutical and Biomedical Analysis*, 14:1455; Kitamura et al., (1989) *J. Cellular Physiol.*, 140:323). In the present invention, the proliferation of TF-1 cells is a function of interaction between the erythropoietin portion and EPO receptors. Specifically, if an erythropoietin portion of an Fc-EPO fusion protein has a reduced on-rate for the EPO receptor, the Fc-EPO protein generally has a reduced activity in a cell-based assay (marked by an increased ED50 value).

Data from cell-based assays, which are relatively easy to obtain, generally correlate with pharmacokinetics and in vivo potency of the Fc-EPO protein. Reduced in vitro activity, indicating a reduced on-rate for the EPO receptor, generally correlates with improved pharmacokinetic properties and enhanced in vivo potency. On the contrary, increased in vitro activity (marked by a decreased ED50 value), indicating an enhanced on-rate for the EPO receptor, generally correlates with poor pharmacokinetic properties and reduced in vivo potency.

The in vivo biological activities of Fc-EPO fusion proteins can be measured by assays conducted in animal models, such as, for example, mice and rats. Examples of in vivo assays include, but are not limited to, hematocrit (HCT) assays and reticulocyte assays. HCT assays measure the volume of blood occupied by red blood cells (RBCs), and are performed simply by centrifuging blood in capillary tubes and measuring the fraction of the total volume occupied by sedimented RBCs. Reticulocytes are new RBCs that have recently differentiated from precursor cells and characterized by containing remnants of nucleic acids from the precursor cells. Reticulocytes are measured by sorting red blood cells in a flow cytometer after staining with a nucleic acid-staining dye, such as, for example, acridine orange or thiazole orange, and counting the staining fraction. Typically, the hematocrit and reticulocytes are measured twice per week.

Reticulocyte data are, in a sense, a first derivative of the hematocrit data. Reticulocyte counts are a measure of the rate of production of red blood cells, while hematocrits measure the total red blood cells. In a typical experiment, the hematocrits of animals administered with Fc-EPO fusion proteins will increase and then return to baseline. When the hematocrits are high and the administered Fc-EPO proteins have disappeared from the animal's circulation system, the reticulocyte count goes below baseline because erythropoiesis is suppressed.

Reticulocytes normally emerge from the bone marrow 4 days after the precursors committed to RBC fates. However, in the presence of high levels of erythropoietin, reticulocytes will often leave the bone marrow after 1-3 days after administration.

Figure 4:
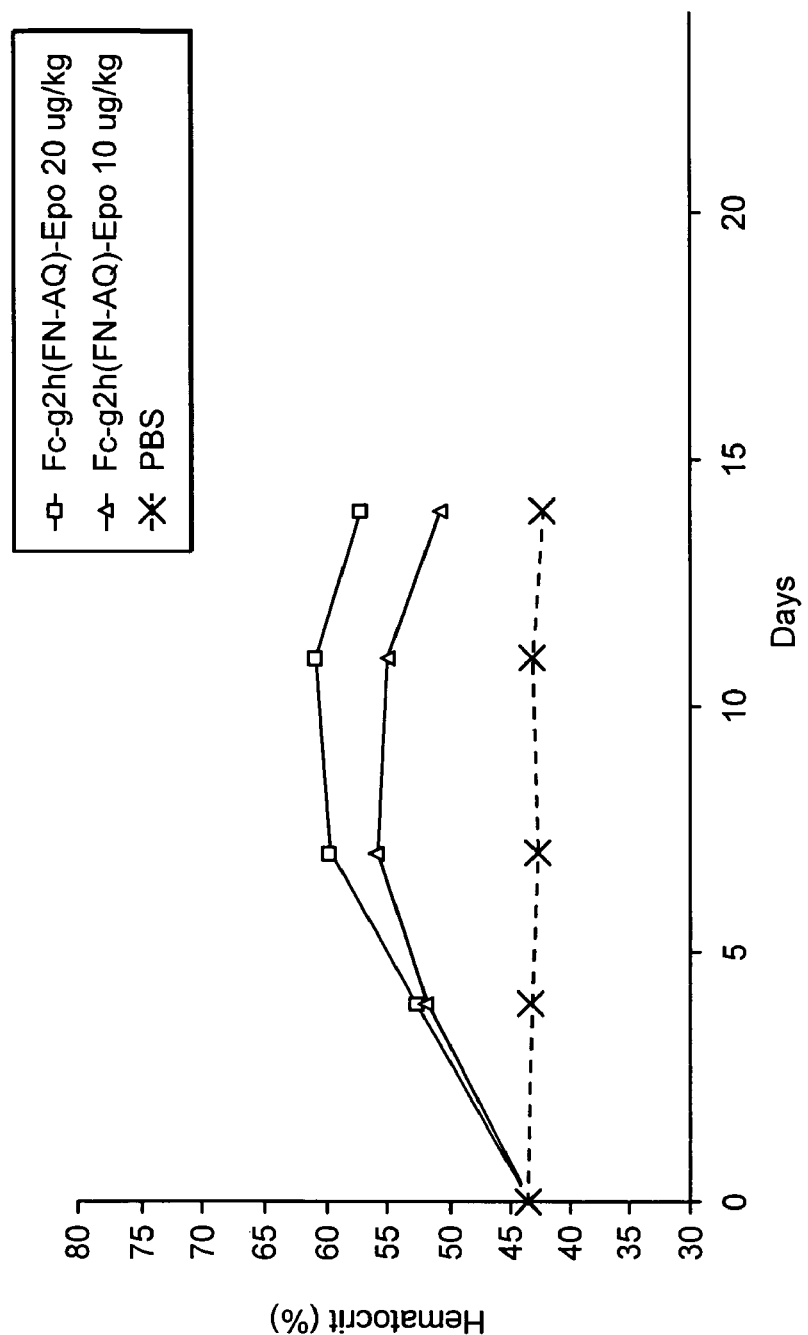
FIG. 4 depicts exemplary hematocrit responses in mice following administration of Fcg2h(FN>AQ)-EPO.
Figure 5:
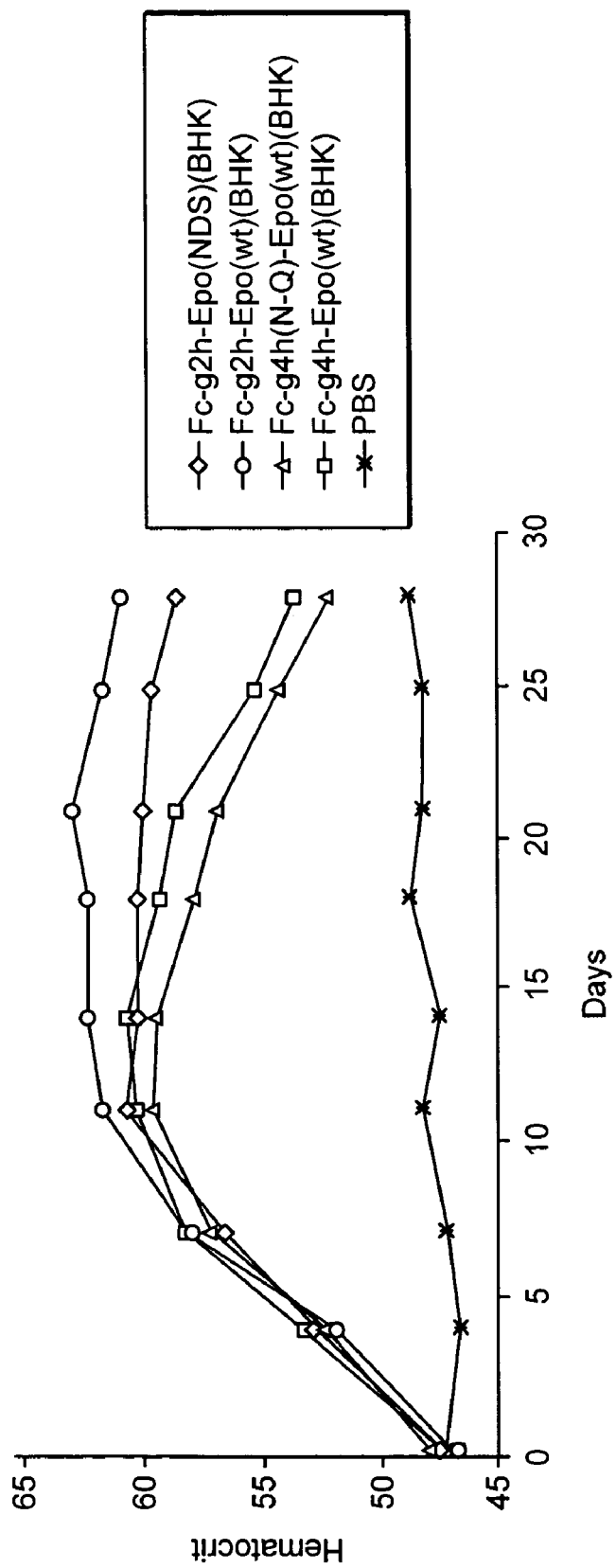
FIG. 5 depicts exemplary hematocrit responses in rats following administration of Fcg2h-EPO, Fcg2h-EPO(NDS), Fcg4h-EPO, and Fcg4h(N>Q)-EPO proteins produced from BHK cells. Sprague-Dawley rats were dosed at 42.5 µg/kg of protein.
Figure 6:
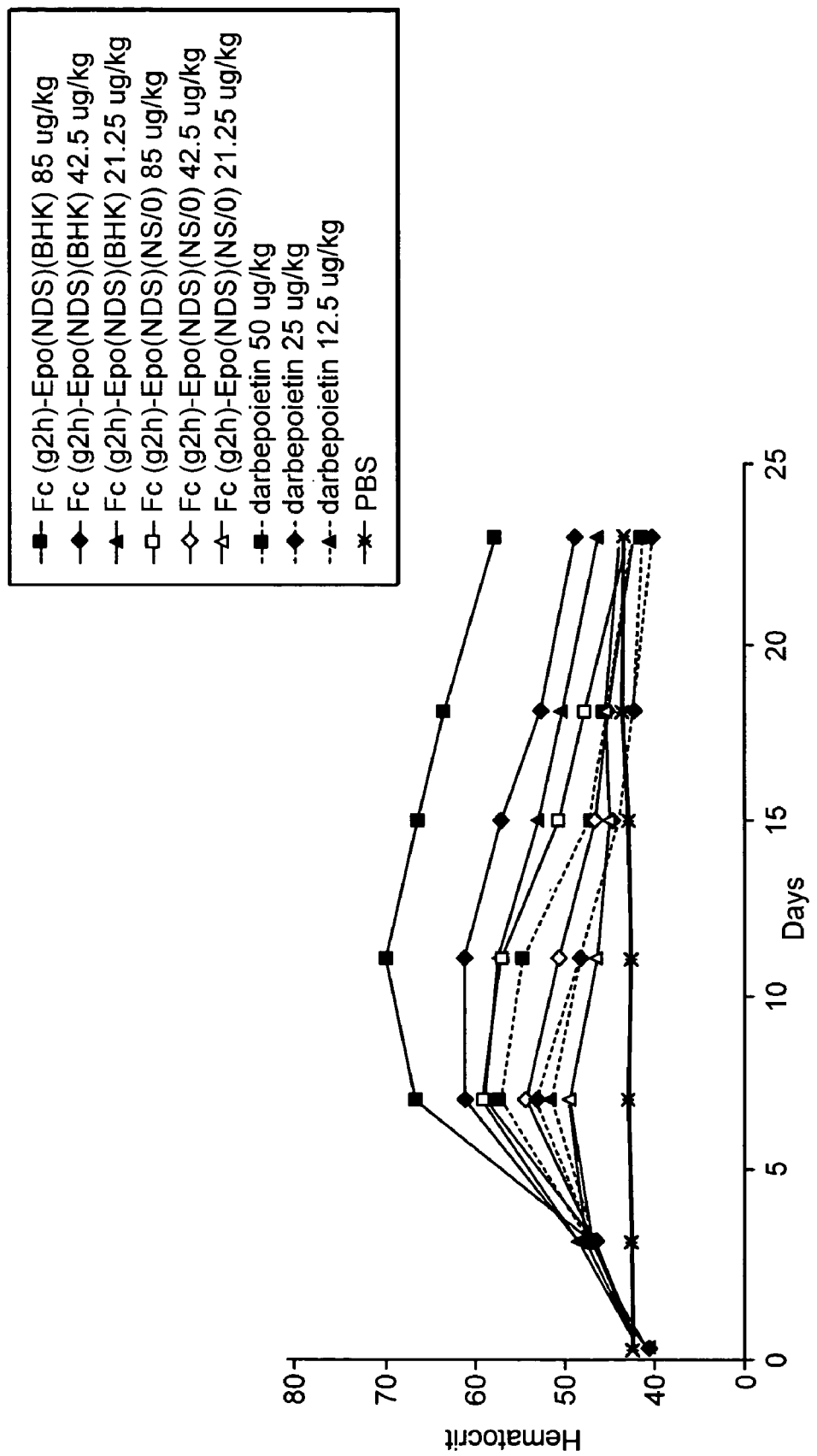
FIG. 6 depicts exemplary hematocrit responses in mice following administration of Fcg2h-EPO(NDS) produced from BHK cells, Fcg2h-EPO(NDS) produced from NS/0 cells, and NESP (i.e., Aranesp®).

In response to an injection of Fc-EPO proteins, the hematocrit readings increase, remain steady, then return to baseline in an animal. Examples of such hematocrit responses are shown in FIGS. 4-6. The maximal rate of decrease is about 7% of blood volume per week in mice, which corresponds to the RBC lifetime of about 45 days in a mouse, and about 5% of blood volume per week in rats, which corresponds to the RBC lifetime of about 65 days in a rat. The maximal rate of decrease presumably represents destruction of RBCs in the absence of new synthesis. If biologically-active Fc-EPO proteins remain in the system at a concentration above the threshold for erythropoiesis, the hematocrit level will remain high and not fall, even if the level of biologically-active Fc-EPO is not detectable in pharmacokinetics experiments.

It has been found that the pharmacokinetic properties of an Fc-EPO protein correlates with the in vivo potency of the protein. All of the features of the present invention that enhance pharmacokinetics of an Fc-EPO fusion protein, as discussed above, also enhance in vivo potency in animal experiments. As shown in Table 1, such features include, for example, addition of the Fc potion, elimination of the glycosylation site in the Fc portion (e.g., N→Q substitution at a position corresponding to Asn297 of IgG1), introduction of the NDS mutations into the erythropoietin portion, and high levels of sialylation by synthesis the FC-EPO protein in the BHK cells.

TABLE 1

Factors that influence the pharmacokinetics and biological activity of Fc-EPO proteins

| Features | Effect on in vitro potency | Effect on pharmacokinetics | Effect on in vivo activity |
| --- | --- | --- | --- |
| Synthesis in BHK cells (vs. NS/0 cells) | Reduction | Enhancement | Enhancement |
| Addition of Fc | Small enhancement | Enhancement | Enhancement |
| NDS Mutations | None | Enhancement | Enhancement |
| N→Q | None | Enhancement | Enhancement |
| g2h (vs. g4h) | Enhancement | Enhancement | Enhancement |

It has been found that, per erythropoietin portion, Fcg2h (FN→AQ)-Epo and Fcg2h-EPO(NDS) made from BHK cells show the best pharmacokinetics and most potent in vivo biological activities. Fcg2h(FN→AQ)-Epo and Fcg2h-EPO (NDS) each have a longer serum half life and more potent in vivo activity per erythropoietin portion than Aranesp®.

Synthesis of Fc-EPO Fusion Proteins

The Fc-EPO fusion protein of the present invention can be produced in suitable cells or cell lines such as human or other mammalian cell lines. Suitable cell lines include, but are not limited to, baby hamster kidney (BHK) cells, Chinese hamster ovary (CHO) cells (including dihydrofolate reductase (DHFR)-deficient cells), and COS cells. In a preferred embodiment, BHK cells are used.

To express the Fc-EPO fusion protein in suitable host cells (e.g., BHK cells), nucleic acid sequences encoding the Fc-EPO fusion protein are first introduced into an expression vector using standard recombinant molecular techniques familiar to those ordinarily skilled in the art. The sequence encoding the erythropoietin portion is preferably codon-optimized for high level expression. Codon-optimized human erythropoietin was described in PCT publication WO 01/36489 (i.e., U.S. application Ser. No. 09/708,506), the disclosures of which are hereby incorporated by reference. An exemplary nucleic acid sequence encoding an erythropoietin portion is provided in SEQ ID NO:1:

```
                                         (SEQ ID NO:1)
GCCCCACCACGCCTCATCTGTGACAGCCGAGTGCTGGAGAGGTACCTCTT

GGAGGCCAAGGAGGCCGAGAATATCACGACCGGCTGTGCTGAACACTGCA

GCTTGAATGAGAACATCACCGTGCCTGACACCAAAGTGAATTTCTATGCC

TGGAAGAGGATGGAGGTTGGCCAGCAGGCCGTAGAAGTGTGGCAGGGCCT

GGCCCTGCTGTCGGAAGCTGTCCTGCGGGGCCAGGCCCTGTTGGTCAACT

CTTCCCAGCCGTGGGAGCCCCTGCAACTGCATGTGGATAAAGCCGTGAGT

GGCCTTCGCAGCCTCACCACTCTGCTTCGGGCTCTGGGAGCCCAGAAGGA

AGCCATCTCCCCTCCAGATGCGGCCTCAGCTGCTCCCCTCCGCACAATCA

CTGCTGACACTTTCCGCAAACTCTTCCGAGTCTACTCCAATTTCCTCCGG

GGAAAGCTGAAGCTGTACACAGGGGAGGCCTGCCGGACAGGGGACAGATGA
```

Exemplary nucleic acid sequences encoding a preferred Fc portion, for example, an Fc portion including a CH2 domain derived from IgG2 and a hinge region derived from IgG1, was described in U.S. Patent Publication No. 20030044423 (i.e., U.S. application Ser. No. 10/093,958), the disclosure of which is hereby incorporated by reference.

Generally, a nucleic acid sequence encoding an Fc-EPO fusion protein includes a nucleic acid sequence encoding a signal peptide (leader sequence). The leader sequence is cleaved during the secretion process. An exemplary nucleic acid sequence (SEQ ID NO:2) encoding a mature Fc-EPO protein without a leader sequence is shown in FIG. 7.

Suitable vectors include those suitable for expression in a mammalian host cell. The vectors can be, for example, plasmids or viruses. The vector will typically contain the following elements: promoter and other "upstream" regulatory elements, origin of replication, ribosome binding site, transcription termination site, polylinker site, and selectable marker that are compatible with use in a mammalian host cell. Vectors may also contain elements that allow propagation and maintenance in prokaryotic host cells as well. Suitable vectors for the present invention includes, but are not limited to, pdCs-Fc-X and vectors derived therefrom, and phC10-Fc-X and vectors derived therefrom.

The vectors encoding Fc-EPO proteins are introduced into host cells by standard cell biology techniques, including transfection and viral techniques. By transfection is meant the transfer of genetic information to a cell using isolated DNA, RNA, or synthetic nucleotide polymer. Suitable transfection methods include, but are not limited to, calcium phosphate-mediated co-precipitation (Sambrook et al. (1989) Molecular Cloning: A Laboratory Manual, $2^{nd}$ ed., Cold Spring Harbor Laboratory Press), lipofection (e.g., Lipofectamine Plus from Life Technologies of Rockville, Md.), DEAE-dextran-mediated transfection techniques, lysozyme fusion or erythrocyte fusion, scraping, direct uptake, osmotic or sucrose shock, direct microinjection, indirect microinjection such as via erythrocyte-mediated techniques, protoplast fusion, or by subjecting the host cells to electric currents (e.g., electroporation), to name but a few. The above list of transfection methods is not considered to be exhaustive, as other procedures for introducing genetic information into cells will no doubt be developed.

To facilitate selection of the host cells containing the nucleic acid encoding the Fc-EPO fusion protein, the nucleic acid encoding the Fc-EPO fusion protein is typically introduced with a selection marker. The selection marker can be encoded by a nucleic acid sequence present on the same expression vector encoding the Fc-EPO fusion protein. Alternatively, the selection marker can be encoded by a nucleic acid sequence present on a different vector. In the latter case, the two vectors can be co-introduced into the host cells by either cotransfection or co-transduction. Suitable selection markers include, for example, Hygromycin B (Hyg B) and dihydrofolate reductase (DHFR).

Transient expression is useful for small-scale protein production and for rapid analysis of an Fc-EPO fusion protein. The host cells containing the nucleic acid sequence encoding the Fc-EPO fusion protein are maintained under conditions suitable for expression of the encoded Fc-EPO fusion protein. Standard cell culture methods, conditions and media can be used for maintaining the host cells expressing the Fc-EPO fusion protein.

Stably transfected cells are often preferred for large-scale production, high level expression, and for other purposes. The stably maintained nucleic acid can be present in any of various configurations in the host cell. For example, in one embodiment, the stably maintained nucleic acid sequence is integrated in a chromosome of a host cell. In other embodiments, the stably maintained nucleic acid sequence can be present as an extrachromosomal array, as an artificial chromosome, or in another suitable configuration.

In one embodiment, BHK cells are used to synthesize the Fc-EPO fusion protein. In order to obtain a stably transfected BHK cell, a nucleic acid sequence encoding the fusion protein and a nucleic acid sequence encoding a selection marker are introduced into BHK cells, preferably by electroporation, protoplast fusion or lipofection methods. The nucleic acid sequence encoding the fusion protein and the nucleic acid sequence encoding a selection marker can be present on the same expression vector. Alternatively, the nucleic acid sequence encoding the fusion protein and the nucleic acid sequence encoding a selection marker can be present on separate vectors. The preferred selection marker for establishing a stable BHK cell is Hyg B. Other selection markers, such as DHFR, can also be used. Stably transfected clones are isolated and propagated by their growth in the presence of Hyg B at a suitable concentration (for example, 200, 250, or 300 micrograms/ml), in standard tissue culture medium, such as, for example, MEM+FBS, DMEM/F-12 medium, or VP-SFM available from Life Technologies, and other suitable media. The expression levels of the Fc-EPO fusion protein can be monitored by standard protein-detecting assays, such as, for example, ELISA test, Western Blot, dot blot, or other suitable assays, on samples from supernatants and culture media. High expression clones are selected and propagated in large scale.

Typically, the BHK cell is an adherent cell line and commonly grown in serum-containing media, such as MEM+ 10% heat-inactivated fetal bovine serum (FBS). However, the BHK cells can be adapted for growth in suspension and in a serum-free medium, such as, for example, VP-SFM (Invitrogen Corp., cat # 11681-020) or Opti-Pro SFM (Invitrogen Corp., cat # 12309). An exemplary adaptation process is described in Example 3. The BHK cells adapted for growth in a serum-free medium can be further adapted for growth in a protein-free medium, such as, for example, DMEM/F-12 (Invitrogen Corp., cat # 11039-021). One exemplary adaptation procedure is described in Example 3. Preferably, DMEM/F-12 is supplemented with suitable amino acids and other components, such as, for example, Glutamine, protein hydrolysates such as HyPep 4601 (Quest International, cat # 5Z10419) and HyPep 1510 (Quest International, cat # 5X59053), Ethanolamine (Sigma, cat# E0135), and Tropolone (Sigma, cat # T7387). Suitable concentrations of each supplement can be determined empirically by those skilled in the art with routine experimentation.

The Fc-EPO fusion proteins synthesized in BHK cells grown in a protein-free medium are sialylated to a greater extent and exhibit more homogeneous sialylation than the corresponding protein synthesized in cells grown in a serum-containing medium (e.g., MEM+FBS) or a serum-free but not protein-free medium (e.g., VP-SFM). In addition, the Fc-EPO protein thus obtained is substantially non-aggregated, i.e., approximately 98% of total yield is non-aggregated. The protein yield from BHK cells grown in a protein-free medium is similar to that from BHK cells grown in serum-containing media, i.e., above 10 microgram/milliliter (mcg/ml). Thus, growth in suspension and/or in a protein-free medium offers a number of advantages, including 1) improving pharmacokinetics of the Fc-EPO fusion protein resulted from increased sialylation; and 2) facilitating downstream purification processes because proteins can be purified from cells grown in suspension mode and in a medium devoid of protein.

Purification

Purification of Fc-EPO is done following standard GMP procedures known by persons skilled in the art. The protein is generally purified to homogeneity or near homogeneity. Chromatographic purifications, such as those involving column chromatography, are generally preferred. Generally, a purification scheme for an Fc-EPO fusion protein may include, but is not limited to, an initial protein capture step; a viral inactivation step; one or more polishing steps; a viral removal step; and a protein concentration and/or formulation step. For example, chromatography resin materials that bind to the Fc portion of the fusion protein can be used to capture Fc-EPO proteins. Suitable resin materials include, but are not limited to, resins coupled to Protein A. Polishing steps may be included to remove contaminating components. For example, hydroxyapatite chromatography, Sepharose Q chromatography, size exclusion chromatography, or hydrophobic interaction chromatography may be used to remove contaminants. One purification method using Protein A-based column chromatography to bind the Fc portion and purify the Fc-EPO fusion protein is described in Example 12, as is an optional method for virus inactivation and removal. The purified proteins are generally concentrated to a desired concentration using ultrafiltration; diafiltered into a suitable formulation buffer; filter sterilized; and dispensed into vials.

Administration

Pharmaceutical Compositions and Administration Routes

The present invention also provides pharmaceutical compositions containing the Fc-EPO protein produced according to the present invention. These pharmaceutical compositions can be used to stimulate red blood cell production and to prevent and to treat anemia. Among the conditions treatable by the present invention include anemia associated with a decline or loss of kidney function (chronic renal failure), anemia associated with myelosuppressive therapy, such as chemotherapeutic or anti-viral drugs (such as AZT), anemia associated with the progression of non-myeloid cancers, anemia associated with viral infections (such as HIV), and anemia of chronic disease. Also treatable are conditions which may lead to anemia in an otherwise healthy individual, such as an anticipated loss of blood during surgery. In general, any condition treatable with rHuEpo can also be treated with the Fc-EPO fusion protein of the invention.

Formulations Containing Fc-EPO Proteins

Generally, a formulation contains an Fc-EPO protein, a buffer and a surfactant in liquid or in solid form. Solid formulations also include, but are not limited to, freeze-dried, spray-freeze-dried or spray-dried formulations. Liquid formulations are preferably based on water, but can contain other components, such as, for example, ethanol, propanol, propanediol or glycerol, to name but a few.

Fc-EPO proteins are formulated in aqueous solutions following standard GMP procedures known to persons skilled in the art. Generally, a formulation is generated by mixing defined volumes of aqueous solutions comprising suitable constituents at suitable concentrations. For example, a formulation typically contains the Fc-EPO protein at a concentration from 0.1 to 200 mg/ml, preferably from 0.2 to 10 mg/ml, more preferably from 0.5 to 6 mg/ml.

Buffer components include any physiologically compatible substances that are capable of regulating pH, such as, for example, citrate salts, acetate salts, histidine salts, succinate salts, maleate salts, phosphate salts, lactate salts, their respective acids or bases or mixtures thereof. Commonly used buffer components are citrate salts and/or their free acid. A formulation typically contains a buffer component at a concentration from 10 to 100 mmol/l, preferably from 2 to 20 mmol/l, more preferably 10 mmol/l.

Surfactants for Fc-EPO formulations can be any excipient used as surfactants in pharmaceutical compositions, preferably polyethylene-sorbitane-esters (Tweens®), such as, Polyoxyethylene(20)-sorbitanmonolaurate, Polyoxyethylene(20)-sorbitanemonopalmitate and Polyoxyethylene(20)-sorbitanemonostearate, and polyoxytheylene-polyoxypropylene-copolymers. A formulation typically contains a surfactant at a concentration from 0.001 to 1.0% w/v, preferably from 0.005 to 0.1% w/v, more preferably from 0.01 to 0.5% w/v.

A formulation can also contain one or more amino acids. Suitable amino acids include, but are not limited to, arginine, histidine, ornithine, lysine, glycine, methionine, isoleucine, leucine, alanine, phenylalanine, tyrosine, and tryptophan. In one embodiment, a formulation of Fc-EPO contains glycine. Preferably, amino acids are used in salt forms, for example, a hydrochloride salt. Applicable amino acid concentrations range from 2 to 200 mmol/L, or from 50 to 150 mmol/L.

Additionally, a formulation can contain sugars such as sucrose, trehalose, sorbitol; antioxidants such as ascorbic acid or glutathion; preservatives such as phenol, m-cresol, methyl- or propylparabene; chlorbutanol; thiomersal; benzalkoniumchloride; polyethyleneglycols; cyclodextrins and other suitable components.

It is desirable that an Fc-EPO formulation is isotonic. For example, osmolality of a formulation can range from 150 to 450 mOsmol/kg. Pharmaceutical formulations have to be stable for the desired shelf-life at the desired storage temperature, such as at 2-8° C., or at room temperature. A useful formulation containing an Fc-EPO protein is well tolerated physiologically, easy to produce, can be dosed accurately, and is stable during storage at 2° C.-8° C. or 25° C., during multiple freeze-thaw cycles and mechanical stress, as well as other stresses such as storage for at least 3 months at 40° C. The stability of Fc-EPO formulations can be tested in a stress test. An exemplary stress test is described in Example 13.

Administration

The therapeutic compositions containing Fc-EPO fusion proteins produced according to the present invention can be administered to a mammalian host by any route. Thus, as appropriate, administration can be oral or parenteral (e.g., i.v., i.a., s.c., i.m.), including intravenous and intraperitoneal routes of administration. In addition, administration can be by periodic injections of a bolus of the therapeutics or can be made more continuous by intravenous or intraperitoneal administration from a reservoir which is external (e.g., an i.v. bag). In certain embodiments, the therapeutics of the instant invention can be pharmaceutical-grade. That is, certain embodiments comply with standards of purity and quality control required for administration to humans. Veterinary applications are also within the intended meaning as used herein.

The formulations, both for veterinary and for human medical use, of the therapeutics according to the present invention typically include such therapeutics in association with a pharmaceutically-acceptable carrier and optionally other ingredient(s). The carrier(s) can be "acceptable" in the sense of being compatible with the other ingredients of the formulations and not deleterious to the recipient thereof. Pharmaceutically acceptable carriers, in this regard, are intended to include any and all solvents, dispersion media, coatings, antibacterial and antifungal agents, isotonic and absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds also can be incorporated into the compositions. The formulations can conveniently be presented in dosage unit form and can be prepared by any of the methods well known in the art of pharmacy/microbiology. In general, some formulations are prepared by bringing the therapeutics into association with a liquid carrier or a finely divided solid carrier or both, and then, if necessary, shaping the product into the desired formulation.

A pharmaceutical composition of the invention is formulated to be compatible with its intended route of administration. Examples of routes of administration include oral or parenteral, e.g., intravenous, intradermal, inhalation (e.g., after nebulization), transdermal (topical), transmucosal, nasal, buccal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

A preferred method for administration of Fc-EPO protein products of the invention is by parenteral (e.g., IV, IM, SC, or IP) routes and the compositions administered would ordinarily include therapeutically effective amounts of product in combination with acceptable diluents, carriers and/or adjuvants. Effective dosages are expected to vary substantially depending upon the condition treated but therapeutic doses are presently expected to be in the range of 0.2 to 2 mcg/kg body weight of the active material. Standard diluents such as human serum albumin are contemplated for pharmaceutical compositions of the invention, as are standard carriers such as saline. Adjuvant materials suitable for use in compositions of the invention include compounds independently noted for erythropoietic stimulatory effects, such as testosterones, progenitor cell stimulators, insulin-like growth factor, prostaglandins, serotonin, cyclic AMP, prolactin and triiodothyronine, as well as agents generally employed in treatment of aplastic anemia, such as methenolene, stanozolol and nandrolone. See, e.g., Resegotti, et al. (1981), *Panminerva Medics,* 23, 243-248; McGonigle, et al., (1984) *Kidney Int.,* 25(2), 437-444; Pavlovic-Kantera, et al., (1980) *Expt. Hematol.,* 8(Supp. 8), 283-291; and Kurtz, (1982) *FEBS Letters,* 14a(1), 105-108.

Also contemplated as adjuvants are substances reported to enhance the effects of, or synergize with, Fc-EPO, such as the adrenergic agonists, thyroid hormones, androgens and BPA as well as the classes of compounds designated "hepatic erythropoietic factors" (see, Naughton et al., (1983) *Acta. Haemat.,* 69, 171-179) and "erythrotropins" as described by Congote et al. in Abstract 364, *Proceedings 7th International Congress of Endocrinology,* Quebec City, Quebec, Jul. 1-7, 1984; Congote (1983), *Biochem. Biophys. Res. Comm.,* 115 (2), 447-483; and Congote, (1984), *Anal. Biochem.,* 140, 428-433, and "erythrogenins" as described in Rothman, et al., (1982), *J. Surg. Oncol.,* 20, 105-108.

Useful solutions for oral or parenteral administration can be prepared by any of the methods well known in the pharmaceutical art, described, for example, in Remington's Pharmaceutical Sciences, (Gennaro, A., ed.), Mack Pub., 1990. Formulations for parenteral administration also can include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions that are solid at room temperature and liquid at body temperatures. Formulations also can include, for example, polyalkylene glycols such as polyethylene glycol, oils of vegetable origin, hydrogenated naphthalenes, and the like. Formulations for direct administration can include glycerol and other compositions of high viscosity. Other potentially useful parenteral carriers for these therapeutics include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition can be sterile and can be fluid to the extent that easy syringability exists. It can be stable under the conditions of manufacture and storage and can be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

In one embodiment, the therapeutics are prepared with carriers that will protect against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods of preparation of such formulations will be apparent to those skilled in the art. The materials also can be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811. Microsomes and microparticles also can be used.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Determining Therapeutically-effective Amount of Fc-EPO and Dosing Frequency

Generally, the therapeutics containing Fc-EPO fusion proteins produced according to the present invention can be formulated for parenteral or oral administration to humans or other mammals, for example, in therapeutically effective amounts, i.e., amounts which provide appropriate concentrations of the drug to a target tissue for a time sufficient to induce the desired effect. More specifically, as used herein, the term "therapeutically effective amount" refers to an amount of Fc-EPO fusion proteins giving an increase in hematocrit to a target hematocrit, or to a target hematocrit range that provides benefit to a patient or, alternatively, maintains a patient at a target hematocrit, or within a target hematocrit range. The amount will vary from one individual to another and will depend upon a number of factors, including the overall physical condition of the patient, severity and the underlying cause of anemia and ultimate target hematocrit for the individual patient. A target hematocrit is typically at least about 30%, or in a range of 30%-38%, preferably above 38% and more preferably 40%-45%. General guidelines relating to target hematocrit ranges for rHuEpo are also found in the EPOGEN® package insert dated Dec. 23, 1996 and are 30%-36%, or alternatively 32%-38% as stated therein. It is understood that such targets will vary from one individual to another such that physician discretion may be appropriate in determining an actual target hematocrit for any given patient. Nonetheless, determining a target hematocrit is well within the level of skill in the art.

A therapeutically effective amount of an Fc-EPO protein may be readily ascertained by one skilled in the art. Example 15 sets forth a clinical protocol which has as one objective to determine a therapeutically effective amount of an Fc-EPO in once per week, once per two weeks, and once per month dosing. For example, a dose range for once per week or once per two weeks administration is from about 0.075 to about 4.5 mcg Fc-EPO per kg per dose. A dose range for once per month administration is 0.45 to 4.5 mcg Fc-EPO per kg per dose.

The effective concentration of the Fc-EPO fusion protein of the invention that is to be delivered in a therapeutic composition will vary depending upon a number of factors, including the final desired dosage of the drug to be administered and the route of administration. The preferred dosage to be administered also is likely to depend on such variables as the type and extent of disease or indication to be treated, the overall health status of the particular patient, the relative biological efficacy (e.g., level of sialylation) of the therapeutics delivered, the formulation of the therapeutics, the presence and types of excipients in the formulation, and the route of administration. In some embodiments, the therapeutics of this invention can be provided to an individual using typical dose units deduced from the mammalian studies using non-human primates and rodents. As described above, a dosage unit refers to a unitary dose which is capable of being administered to a patient, and which can be readily handled and packed, remaining as a physically and biologically stable unit dose comprising either the therapeutics as such or a mixture of it with solid or liquid pharmaceutical diluents or carriers.

The dosing frequency for a therapeutic containing the Fc-EPO fusion protein will vary depending upon the condition being treated and the target hematocrit, but in general will be less than three times per week. The dosing frequency may be about once or twice per week. The dosing frequency may also be less than about one time per week, for example about once every two weeks (about one time per 14 days), once per month or once every two months. It is understood that the dosing frequencies actually used may vary somewhat from the frequencies disclosed herein due to variations in responses by different individuals to the erythropoietin and its analogs; the term "about" is intended to reflect such variations.

The invention also provides for administration of a therapeutically effective amount of iron in order to maintain increased erythropoiesis during therapy. The amount to be given may be readily determined by one skilled in the art based upon therapy with rHuEpo. Additionally, the therapeutics of the present invention can be administered alone or in combination with other molecules known to have a beneficial effect on the particular disease or indication of interest. By way of example only, useful cofactors include symptom-alleviating cofactors, including antiseptics, antibiotics, antiviral and antifungal agents and analgesics and anesthetics.

Prodrug

Therapeutics of the invention also include the "prodrug" derivatives. The term prodrug refers to a pharmacologically inactive (or partially inactive) derivative of a parent molecule that requires biotransformation, either spontaneous or enzymatic, within the organism to release or activate the active component. Prodrugs are variations or derivatives of the therapeutics of the invention which have groups cleavable under metabolic conditions. Prodrugs become the therapeutics of the invention which are pharmaceutically active in vivo, when they undergo solvolysis under physiological conditions or undergo enzymatic degradation. A prodrug of this invention can be called single, double, triple, and so on, depending on the number of biotransformation steps required to release or activate the active drug component within the organism, and indicating the number of functionalities present in a precursor-type form. Prodrug forms often offer advantages of solubility, tissue compatibility, or delayed release in the mammalian organism (see, Bundgard, (1985) *Design of Prodrugs*, pp. 7-9, 21-24, Elsevier, Amsterdam; Silverman, (1992) *The Organic Chemistry of Drug Design and Drug Action*, pp. 352-401, Academic Press, San Diego, Calif.). Moreover, the prodrug derivatives according to this invention can be combined with other features to enhance bioavailability.

In vivo Expression

The Fc-EPO fusion protein of the present invention can be provided by in vivo expression methods. For example, a nucleic acid encoding an Fc-EPO fusion protein can be advantageously provided directly to a patient suffering from a hematopoietic disorders or deficiency, or may be provided to a cell ex vivo, followed by administration of the living cell to the patient. In vivo gene therapy methods known in the art include providing purified DNA (e.g. as in a plasmid), providing the DNA in a viral vector, or providing the DNA in a liposome or other vesicle (see, for example, U.S. Pat. No. 5,827,703, disclosing lipid carriers for use in gene therapy, and U.S. Pat. No. 6,281,010, providing adenoviral vectors useful in gene therapy).

Methods for treating disease by implanting a cell that has been modified to express a recombinant protein are also known. See, for example, U.S. Pat. No. 5,399,346, disclosing methods for introducing a nucleic acid into a primary human cell for introduction into a human.

In vivo expression methods are particularly useful for delivering a protein directly to targeted tissues or cellular compartment without purification. In the present invention, gene therapy using the sequence encoding Fc-EPO can find use in a variety of disease states, disorders and states of hematologic irregularity including anemia, in particularly correction of anemia of a type associated with chronic renal failure and the like. A nucleic acid sequence coding for an Fc-EPO fusion protein can be inserted into an appropriate transcription or expression cassette and introduced into a host mammal as naked DNA or complexed with an appropriate carrier. Monitoring of the production of active Fc-EPO protein can be performed by nucleic acid hybridization, ELISA, western hybridization, and other suitable methods known to ordinary artisan in the art.

It has been found that a plurality of tissues can be transformed following systemic administration of transgenes. Expression of exogenous DNA following intravenous injection of a cationic lipid carrier/exogenous DNA complex into a mammalian host has been shown in multiple tissues, including T lymphocytes, reticuloendothelial system, cardiac endothelial cells lung cells, and bone marrow cells, e.g., bone marrow-derived hematopoietic cells.

The in vivo gene therapy delivery technology as described in U.S. Pat. No. 6,627,615, is non-toxic in animals and transgene expression has been shown to last for at least 60 days after a single administration. The transgene does not appear to integrate into host cell DNA at detectable levels in vivo as measured by Southern analysis, suggesting that this technique for gene therapy will not cause problems for the host mammal by altering the expression of normal cellular genes activating cancer-causing oncogenes, or turning off cancer-preventing tumor suppressor genes.

EXAMPLES

Example 1

Constructs Encoding Fc-EPO Fusion Proteins

Plasmid phC10-Fcg2h(FN>AQ)-M1-EPO encoding an Fc-EPO fusion protein containing a normal erythropoietin portion and plasmid phC10-Fcg2h(FN>AQ)-M1-EPO(NDS) encoding an Fc-EPO fusion protein with NDS mutations were constructed as follows.

The nucleic acid sequence encoding human erythropoietin was codon-optimized for high expression in mammalian cells. For example, SEQ ID NO:3 shows an example of coding sequences of mature human erythropoietin with modified codons to optimize translation. The sequence of the 5' end was also modified to include a Sma I site to facilitate subcloning.

SEQ ID NO:3

```
CCCGGGtGCCCCACCACGCCTCATCTGTGACAGCCGAGTgCTGGAGAGGT
ACCTCTTGGAGGCCAAGGAGGCCGAGAATATCACGACcGGCTGTGCTGAA
CACTGCAGCTTGAATGAGAAcATCACcGTgCCtGACACCAAAGTgAATTT
CTATGCCTGGAAGAGGATGGAGGTtGGcCAGCAGGCCGTAGAAGTgTGGC
AGGGCCTGGCCCTGCTGTCGGAAGCTGTCCTGCGGGCCAGGCCCTGTTG
GTCAACTCTTCCCAGCCGTGGGAGCCCCTGCAaCTGCATGTGGATAAAGC
CGTgAGTGGCCTTCGCAGCCTCACCACTCTGCTTCGGGCTCTGgGAGCCC
AGAAGGAAGCCATCTCCCCTCCAGATGCGGCCTCAGCTGCTCCcCTCCGc
ACAATCACTGCTGACACTTTCCGCAAACTCTTCCGAGTCTACTCCAATTT
CCTCCGGGGAAAGCTGAAGCTGTACACAGGGGAGGCCTgcCGGACAGGGG
ACAGATGActcgag
```

(Small characters indicate base differences from the wild-type human erythropoietin coding sequence. The changes are predicted to increase the expression level in mammalian cells but not to change the expressed protein sequence.)

NDS mutations were introduced into the erythropoietin portion by site-directed mutagenesis as described in PCT publication WO 01/36489, the disclosures of which are hereby incorporated by reference. For example, an Xma I-Xho I DNA fragment containing a form of the human erythropoietin coding sequence with mutations resulting in the amino acid substitutions His32Gly, Cys33Pro, Trp88Cys, and Pro90Ala, as disclosed in WO01/36489, was used. The corresponding protein sequence is shown in SEQ ID NO:4.

(SEQ ID NO:4)
```
APPRLICDSRVLERYLLEAKEAENITTGCAEGPSLNFNITVPDTKVNFYA
WKRMEVGQQAVEVWQGLALLSEAVLRGQALLVNSSQPCEGLQLHVDKAVS
GLRSLTTLLRALGAQKEAISPPDAASAAPLRTITADTFRKLFRVYSNFLR
GKLKLYTGEACRTGDR
```

A hybrid Fc portion, including an IgG2-derived CH2 domain and an IgG1-derived hinge region, was constructed as described in U.S. Patent Publication No. 20020147311 (i.e., U.S. patent application Ser. No. 10/093,958), the disclosures of which are hereby incorporated by reference.

The Xma I-Xho I DNA fragment encoding a form of erythropoietin was inserted into a plasmid vector, for example, pdCs-Fc-X, that encodes an altered hinge region from IgG1 and a CH2 and CH3 region from IgG2, except that there were two sets of mutations (referred to herein as M1 set mutations) that resulted in amino acid substitutions in the region of the CH3 C-terminus, such that the sequence at the junction of the CH3 C-terminus and the EPO N-terminus is as follows:

....TQKSATATPGA-APPRLI.... (SEQ ID NO:5)

The first set of mutations, which change the sequence KSLSLSPG (SEQ ID NO:6) of the IgG2 CH3 region to KSATATPG (SEQ ID NO:7), is disclosed in U.S. Patent Application Ser. No. 60/280,625, the entire disclosure of which is hereby incorporated by reference. The effect of the substitution of Leu-Ser-Leu-Ser (position 3 to position 6 of SEQ ID NO:6) with Ala-Thr-Ala-Thr (position 3 to position 6 of SEQ ID NO:7) is to remove potential human non-self T-cell epitopes that may arise because the junction between human Fc and human erythropoietin contains non-self peptide sequences. The second set consisting of the single amino acid substitution K to A at the C-terminal amino acid of the CH3 region, is disclosed in U.S. patent application Ser. No. 09/780,668, the entire disclosure of which is hereby incorporated by reference.

Expression vector pdCs-Fc-X for the expression of Fc fusion proteins was described by Lo et al., (1998) *Protein Engineering* 11:495. The plasmid phC10-Fc-X was constructed from pdCs-Fc-X by replacing the coding region of the dihydrofolate reductase (DHFR) gene conferring resistance to methotrexate with the gene conferring resistance to Hygromycin B. A Nhe I/Nsi I Hygromycin B DNA fragment was obtained by PCR amplification of the Hygromycin B gene from the template plasmid pCEP4 (Invitrogen) using the primers 5'-GCTAGCTTGGTGCCCTCATGAAAAAGC-CTGAACTC-3' (SEQ ID NO:8) and 5'-ATGCATTCAGT-TAGCCTCCCCCATC-3' (SEQ ID NO:9). The PCR fragment was cloned into the TA cloning vector pCR2.1 (Invitrogen), and its sequence confirmed.

Plasmid phC10-Fcg2h-M1-EPO(NDS) was generated by a triple ligation of Nhe I/Afl I and Afl II/Nsi I DNA fragments from pdCs-Fcg2h-M1-EPO(NDS) and the Nhe I/Nse I Hygromycin B fragment.

Additionally, a mutation leading to a double amino acid substitution, "FN>AQ", within the Gln-Phe-Asn-Ser amino acid sequence within the CH2 domain of the IgG2 heavy chain that eliminates a potential T-cell epitope and N-linked glycosylation in the Fc portion was introduced by PCR mutagenesis. The mutagenic primers 5'-AGCAGGCCCA-GAGCACGTTCCGTGTGGT-3' (SEQ ID NO:10) and 5'-GAACGTGCTCTGGGCCTGCTCCTCCCGT-3' (SEQ ID NO:11) were paired respectively with a downstream primer containing a Sac II site 5'-CCCCGCGGGTCCCAC-CTTTGG-3' (SEQ ID NO:12) and an upstream primer containing a Pvu II site 5'-CCCAGCTGGGTGCTGACACGT-3' (SEQ ID NO:13), and two overlapping DNA fragments were amplified from the template DNA pdC10-Fcg2h-M1-EPO (NDS). In a second amplification round, a Pvu II/Sac II fragment containing the mutation (FN>AQ) was amplified using the upstream primer (SEQ ID NO:13) and downstream primer (SEQ ID NO:12) from the PCR products from the first amplification round. The Pvu II/Sac II fragment was cloned into a TA vector pCR2.1 (Invitrogen), and its sequence verified. Construct pdC10-Fcg2h(FN>AQ)-M1-EPO(NDS) was generated from a triple ligation of the Pvu II/Sac II fragment, a Xho I/Sac II fragment from pdC10-Fcg2h-M1-EPO, and a Xho I/Pvu II fragment from pdC10-Fcg2h-M1-EPO(NDS).

To introduce the FN>AQ mutation into the plasmid phC10-Fcg2h-M1-EPO, the appropriate DNA fragments from phC10-Fcg2h-M1-EPO and from pdC10-Fcg2h(FN>AQ)-M1-EPO were combined. Both phC10-Fcg2h-M1-EPO and pdC10-Fcg2h(FN>AQ)-M1-EPO constructs were digested with Xho I and Xba I, and the 5.7 kb Xho I/Xba I phC10-Fcg2h-M1-EPO(NDS) fragment was ligated with the 1.9 kb pdC10-Fcg2h(FN>AQ)-M1-EPO fragment, generating phC10-Fcg2h(FN>AQ)-M1-EPO.

To introduce the FN>AQ mutation into the plasmid phC10-Fcg2h-M1-EPO(NDS), the two appropriate Xho I/Sma I digested fragments from phC10-Fcg2h-M1-EPO(NDS) and from phC10-Fcg2h(FN>AQ)-M1-EPO were ligated together, generating phC10-Fcg2h(FN>AQ)-M1-EPO (NDS).

The amino acid sequence of Fc-EPO encoded by pdC10-huFcg2h(FN>AQ)-M1-EPO is shown in SEQ ID NO:14.

(SEQ ID NO:14)
EPKSSDKTHTCPPCPAPPVAGPSVFLFPPKPKDTLMISRTPEVTCVVVDV

SHEDPEVQFNWYVDGVEVHNAKTKPREEQAQSTFRVVSVLTVVHQDWLNG

KEYKCKVSNKGLPAPIEKTISKTKGQPREPQVYTLPPSREEMTKNQVSLT

CLVKGFYPSDIAVEWESNGQPENNYKTTPPMLDSDGSFFLYSKLTVDKSR

WQQGNVFSCSVMHEALHNHYTQKSATATPGAAPPRLICDSRVLERYLLEA

KEAEMTTGCAEHCSLNENITVPDTKVNFYAWKRMEVGQQAVEVWQGLALL

SEAVLRGQALLVTNSSQPWEPLQLHVDKAVSGLRSLTTLLRALGAQKEAI

SPPDAASAAPLRTITADTFRKLFRVYSNFLRGKLKLYTGEACRTGDR

The amino acid sequence of Fc-EPO(NDS) encoded by pdC10-huFcg2h(FN>AQ)-M1-EPO(NDS) is shown in SEQ ID NO:15.

(SEQ ID NO:15)
EPKSSDKTHTCPPCPAPPVAGPSVFLFPPKPKDTLMISRTPEVTCVVVDV

SHEDPEVQFNWYVDGVEVHNAKTKPREEQAQSTFRVVSVLTVVHQDWLNG

KEYKCKVSNKGLPAPIEKTISKTKGQPREPQVYTLPPSREEMTKNQVSLT

CLVKGFYPSDIAVEWESNGQPENNYKTTPPMLDSDGSFFLYSKLTVDKSR

WQQGNVFSCSVMHEALHNHYTQKSATATPGAAPPRLICDSRVLERYLLEA

KEAENITTGCAEGPSLNENITVPDTKVNFYAWKRMEVGQQAVEVWQGLAL

LSEAVLRGQALLVNSSQPCEALQLHVDKAVSGLRSLTTLLRALGAQKEAI

SPPDAASAAPLRTITADTFRKLFRVYSNFLRGKLKLYTGEACRTGDR

Example 2

Expression of Fc-EPO in Various Cell Lines

For rapid analysis of the fusion protein, a plasmid, phC10-Fcg2h(FN>AQ)-M1-EPO(NDS) or phC10-Fcg2h(FN>AQ)-M1-EPO, was introduced into suitable tissue culture cells by standard transient transfection methods, such as, for example, by calcium phosphate-mediated DNA co-precipitation (Sambrook et al. (1989) Molecular Cloning: A Laboratory Manual, 2$^{nd}$ ed., Cold Spring Harbor Laboratory Press), or by lipofection using Lipofectamine Plus (Life Technologies) according to the manufacturer's protocol.

In order to obtain stably transfected BHK-21 cells, a plasmid, phC10-Fcg2h(FN>AQ)-M1-EPO(NDS) or phC10-Fcg2h(FN>AQ)-M1-EPO, was introduced into BHK-21 cells by electroporation. For high-efficiency electroporation, BHK-21 cells, grown in MEM medium (supplemented with non-essential amino acids and sodium pyruvate as recommended by the American Type Culture Collection (ATCC)), were washed once with PBS; and approximately 5×10$^6$ cells were resuspended in 0.5 ml PBS and incubated with 10 μg of linearized plasmid DNA in a Gene Pulser™ Cuvette with a 0.4 cm electrode gap (BioRad, Hercules, Calif.) on ice for 10 min. Electroporation was performed using a Gene Pulser™ (BioRad, Hercules, Calif.) with settings at 0.25 V and 500 μF. Cells were allowed to recover for 10 min on ice, resuspended in growth medium, and plated onto two 96 well plates. Hygromycin B (Hyg B) was added to the growth medium two days post-transfection at a concentration of 300 micrograms/ml. The cells were fed every 3 days for two to three more times, and Hyg B resistant stable clones appeared in 2 to 3 weeks.

To identify stable clones producing high levels of the Fc-EPO fusion protein, supernatants from clones were assayed by ELISA with anti-Fc antibodies. High-producing clones were isolated and propagated in growth medium containing 300 micrograms/ml Hyg B. For protein production purposes, BHK-21 cells were routinely grown in a supplemented DMEM/F-12 medium, or in another suitable medium such as VP-SFM (Life Technologies). The Fc-EPO fusion protein was harvested from the conditioned medium by standard normal-flow filtration, and the clarified material was stored at 4 degrees Celsius until further purification. Typically, in a roller bottle production mode, yields of 6-12 mcg/ml of Fc-EPO proteins were obtained from BHK-21 cells.

Fc-EPO fusion proteins were also expressed in and recovered from NS/0 cells. NS/0 clones stably maintaining the plasmid pdC10-Fcg2h(FN>AQ)-M1-EPO or pdC10-Fcg2h(FN>AQ)-M1-EPO(NDS) were established by methods previously described in PCT publication WO 01/36489, the entire disclosures of which are hereby incorporated by reference. Typically, yields of 50-100 mcg/ml of Fc-EPO protein were obtained from NS/0 cells.

Example 3

Adaptation of BHK Cells for Growth in Suspension and/or in Protein-free Media

BHK is an adherent cell line commonly grown in serum-containing media, such as, for example, MEM+10% heat-inactivated fetal bovine serum (FBS). To maintain and expand BHK cells, they are periodically (e.g., in 4 day intervals) detached from their substrate, typically by the action of a trypsin-EDTA solution, diluted in fresh media and re-seeded in appropriate vessels. However, BHK cells can be adapted for growth in suspension and in serum-free and/or protein-free media by the following procedures.

In a typical adaptation process, BHK cells were first cultured in 75:25 (v/v) mixture of MEM+FBS:target medium until exponential stage, and subsequently subcultured at an appropriate cell density in 50:50 (v/v), 25:75 (v/v), and finally 0:100 (v/v) original medium:target medium. During the adaptation process, the growth of the BHK cells was monitored by visual inspection. The following serum-free media were tested for adaptation: 293 SFM II (Invitrogen Corp., cat # 11686-929), CHO-S-SFM II (Invitrogen Corp., cat # 12052-098), VP-SFM (Invitrogen Corp., cat # 11681-020), Opti-Pro SFM (Invitrogen Corp., cat # 12309), CD Hybridoma (Invitrogen Corp., cat # 11279-023), and H-SFM (Invitrogen Corp., cat # 12045-076).

To switch BHK cells from an adherent cell line to a suspension cell line during the adaptation process, the culture mix was allowed to sit before each passage, and the top 25% of the cell suspension was removed and diluted into a fresh medium. Because cells that aggregate settled to the bottom of the culture vessels more rapidly than single and doublet cells, the top 25% cell suspension generally contains those cells that exhibit the least amount of aggregation. Thus, each passage expands and enriches the BHK cells less prone to aggregation, and suspension cell lines of BHK clones expressing Fc-EPO proteins were established by this method.

It was found that BHK cells expressing Fc-EPO proteins could be adapted for growth in VP-SFM or Opti-PRO SFM serum-free media and suspension cultures were obtained. The BHK cells expressing Fc-EPO fusion proteins were not able to grow in the following serum-free media: 293 SFM II, CHO-S-SFM II, CD Hybridoma, and H-SFM.

BHK cells adapted to the serum-free medium, VP-SFM, were further adapted to grow in a protein-free medium, e.g., DMEM/F-12 (Invitrogen Corp., cat # 11039-021) by sequentially culturing the BHK cells, at an appropriate cell density, in 75:25 (v/v), 50:50 (v/v), 25:75 (v/v), and finally 0:100 (v/v) VP-SFM: DMEM/F-12 mixture. The protein-free medium DMEM/F-12 was supplemented with Glutamine (6 mM final), 2 g/l HyPep 4601 (Quest International, Chicago, Ill., cat # 5Z 10419,), 2 g/l HyPep 1510 (Quest International, Chicago, Ill., cat # 5X59053,), 10 l/l (v/v) Ethanolamine (Sigma, cat# E0135), and 5 µM Tropolone (Sigma, cat # T7387). A BHK cell line stably expressing Fc-EPO fusion protein competent to grow in supplemented DMEM/F-12 was obtained by this method and maintained at high cell viability.

Example 4

Purification and Characterization of Protein Aggregation State

For analysis, Fc-EPO fusion proteins were purified from cell-culture supernatants via Protein A chromatography based on the affinity of the Fc portion for Protein A. The conditioned supernatant from cells expressing Fc-EPO proteins was loaded onto a pre-equilibrated Fast-Flow Protein A Sepharose column. The column was washed extensively with sodium phosphate buffer (150 mM Sodium Phosphate, 100 mM NaCl at neutral pH). Bound protein was eluted by a low pH (pH 2.5-3) sodium phosphate buffer (composition as above) and the eluted fractions were immediately neutralized.

To assess the aggregation state of the Fc-EPO fusion proteins produced by different cell lines, Protein A purified samples were analyzed by analytical size exclusion chromatography (SEC). The samples were fractionated by HPLC-SEC (e.g., Super 3000 SW, TosoHaas, Montgomeryville, Pa.), in a fifteen-minute run at a flow rate of 0.35 ml/min. A substantial portion of the Fc-EPO proteins (e.g., up to 90% to 100% of total yield) produced from BHK cells was non-aggregated. Furthermore, samples of the Fc-EPO fusion proteins analyzed by reducing SDS-PAGE (precast NuPAGE 4%-12% gel, NuPAGE, Novex) revealed substantially a single band, indicating that the products were resistant to degradation under standard operating procedures.

Fc-EPO fusion proteins purified from BHK cells grown in suspension, in serum-free media, and/or in protein-free media were also characterized by SDS-PAGE and analytical SEC as described above. The proteins were found to be substantially non-aggregated and not degraded, like proteins synthesized in BHK cells grown in serum-containing media.

Example 5A

Characterization of Glycosylation Patterns

Serine126 in human erythropoietin is in a sequence compatible with O-glycosylation, and is conserved in all mammalian erythropoietin proteins. However, serine126 is in a "floppy loop" that does not pack tightly against the rest of the protein. In the absence of O-glycosylation, this region of erythropoietin might be particularly sensitive to proteolysis.

The status of O-glycosylation at Ser126 in Fc-EPO proteins produced in different cell lines was examined by reversed phase HPLC. Samples were denatured and reduced, diluted into 0.1% triflouroacetic acid (TFA), and injected into a reversed phase HPLC column (e.g., a Vydac C4 column, Grace Vydac). A gradient into 0.085% TFA in acetonitrile was applied and the retention times of the protein samples were recorded. It was found that Fc-EPO and Fc-g2h (FN>AQ)-EPO synthesized in BHK-21 cells produced two partially overlapping major peaks (Peak #1 and Peak #2). The peak fractions were further analyzed by peptide mapping. It was found that Peak #1 corresponded to a form of Fc-EPO that was glycosylated at Ser126, as indicated by the absence of a signature peptide (Peptide #36), whereas Peak #2 corresponded to a form of Fc-EPO that was not glycosylated at Ser126, as indicated by the presence of the signature peptide (Peptide #36). It was found that Ser126 is modified by O-glycosylation in about 60% of the Fc-EPO molecules produced from BHK cells, which is consistent with what has been reported for naturally occuring EPO. Furthermore, growth of BHK cells in supplemented protein-free DMEM/F-12 medium had a positive effect on frequency of O-glycosylation.

Example 5B

Characterization of Sialylation Patterns

The extent of sialylation of Fc-EPO fusion proteins synthesized in NS/0, BHK, 293, and PerC6 cells was compared by isoelectric focusing (IEF) gel electrophoresis. Briefly, samples, concentrated to 2 mg/ml and desalted if necessary, were added to an equal volume of IEF Sample Buffer pH 3-7, and run on a vertical precast Novex pH 3-7 IEF Gel (Novex, cat# EC6655B/B2) for 2.5 hours, first hour at 100V, second hour at 200V and last 30 minutes at 500V. The gel was then fixed, stained and destained.

In one particular experiment, the following samples were compared (samples were derived from cells grown in serum-containing media):
1. Fcg2h-EPO(NDS) from NS/0
2. Fcg2h-EPO(NDS) from BHK-21
3. Fcg2h-EPO from BHK-21
4. Fcg2h("Delta Lys")-EPO from BHK-21
5. Fcg4h(FN→AQ "Delta Lys")-EPO from BHK-21
6. Fcg4h("Delta Lys")-EPO from BHK-21

In this group, "Delta Lys" refers to a deletion of the lysine at the C-terminus of the Fc domain (samples 4-6). Samples 1-3 have a mutation of this C-terminal lysine to an alanine. Therefore this C-terminal lysine is absent in all of the samples and there is no resulting charge difference between the samples. All cells were grown as adherent cells in serum-containing media.

Samples were loaded onto a pH 3-7 IEF gel and compared with standards that focused at pH 3.5, 4.2, 4.5, 5.2, 5.3, 6.0, and 6.9 (Serva Electrophoresis, Germany). The first sample, Fcg2h-EPO(NDS) from NS/0, migrated as a distribution of bands with isoelectric points between about pH 5.3 and 6.5; the most intense bands were present at pH 6.0-6.1. The second sample, Fcg2h-EPO(NDS) from BHK-21, ran as a distribution of intense bands with isoelectric points at about pH 4.6 to pH 5.0, with fainter bands from pH 5.0 to about pH 6.0; the most intense bands were present at pH 4.8-4.9. The third and fourth samples, Fcg2h-EPO from BHK-21 and Fcg2h("Delta Lys")-EPO from BHK-21, respectively, both had a distribution of bands from about pH 4.7 to 6.0 with the most intense bands focused at about pH 5.3. The fifth and sixth samples, Fcg4h(FN→AQ "Delta Lys")-EPO from BHK-21 and Fcg4h ("Delta Lys")-EPO from BHK-21, respectively, had a focusing pattern similar to that of the second sample, i.e., ran as a distribution of intense bands with isoelectric points at about pH 4.6 to pH 5.0, with fainter bands from pH 5.0 to about pH 6.0. These results indicate that synthesis of Fc-EPO fusion proteins in BHK cells generally resulted in a significantly more acidic product than identical or similar products synthesized in NS/0 cells.

In other experiments, samples of Fcg2h-M1-EPO(NDS) from BHK cells were treated with neuraminidase, which removes sialic acid from oligosaccharides. The resulting neuraminidase-treated samples were run on an IEF gel and found to focus as a few bands at pH 6.9 and greater. When the banding patterns of samples from BHK cells with or without neuraminidase treatment and of samples from NS/0 cells were compared, about 27 distinct sialylated species were identified. The 27 species correspond well with the predicted 28 different species that could result from varying extents of sialylation of an Fc-EPO fusion protein in homodimeric configuration. According to this analysis, Fcg2h-EPO with 4-5 sialic acid residues focused with the pH 6.9 marker, and Fcg2h-EPO with 11-12 sialic acid residues focused with the pH 6.0 marker. It was found that a population of Fcg2h-EPO proteins synthesized in BHK cells appeared to have an average of 21 sialic acid residues per protein molecule. In contrast, a population of Fc(g2h)-EPO proteins synthesized in NS/0 cells appeared to have an average about 10 sialic acid residues per protein molecule.

In subsequent experiments, BHK cells expressing Fc-EPO proteins were adapted to serum-free growth conditions and conditions appropriate for large-scale production, e.g., suspension conditions. Fc-EPO proteins produced from BHK cells grown in serum-free and in suspension were analyzed by IEF gel electrophoresis as described above. These alterations in growth conditions resulted in shifts of, at most, only 0.1 to 0.3 pH units in the isoelectric point of the most intense band.

Samples of the Fc-EPO fusion proteins synthesized in supplemented DMEM/F-12 protein-free media were similarly characterized by IEF gel electrophoresis. It was found that the protein product was sialylated to a greater extent and exhibited more homogeneous sialylation than the corresponding product obtained from cells grown in serum-free media such as VP-SFM.

The extent of sialylation of Fc-EPO proteins produced in different cell lines was also qualitatively confirmed by lectin-binding studies. For example, Fc-EPO fusion proteins were first separated by standard SDS gel electrophoresis and blotted, then probed with modified lectins that recognize distinct carbohydrate moieties (e.g., commercially available from Roche Applied Science, Indianapolis, Ind.), and bound lectins can be visualized. Suitable lectins include, but are not limited to, *Sambucus nigra* agglutinin (SNA) or *Maackia amurensis* agglutinin (MAA), which recognize sialic acids with specific linkages, and *Datura stramonium* agglutinin (DAA), Peanut agglutinin (PNA) and jacalin, which recognize other regions of the carbohydrate moiety such as the O-glycan core. Based on lectin binding assays, sialylation levels of Fc-EPO fusion proteins produced in different cell lines could be determined.

Example 6

In vitro Biological Activity of Fc-EPO Variants

The in vitro activities of different Fc-EPO proteins were tested in a cell-based assay. The TF-1 cell line expresses EPO receptors, and accordingly, under appropriate culture conditions, its incorporation of tritiated thymidine is a function of EPO or EPO-like protein activity (Hammerlling et al., (1996) *J. Pharmaceutical and Biomedical Analysis*, 14:1455; Kitamura et al., (1989) *J. Cellular Physiol.*, 140:323). Specifically, TF-1 cells in active log-phase were washed twice in a medium without EPO, and plated at about $10^4$ cells/well in microtiter plates. The cells were then incubated in a medium with a titrated dilution series of the Fc-EPO variants for 48 hours. 0.3 µCi of $^3$H-thymidine were added to the wells ten hours before assaying cell proliferation. As controls, TF-1 cells were also incubated in the presence of recombinant human EPO, and hyperglycosylated EPO analogue Aranesp®. Incorporation of radioactive thymidine was measured as total TCA-precipitable counts. As shown in Table 2, the activities of Fcg2h-M1-EPO molecules are comparable to that of recombinant human EPO.

Some general conclusions can be drawn from this data. Consistent with previously reported results, EPO produced from CHO cells has an ED50 of about 0.7 ng/ml; this includes the NIBSC EPO standard, EPO from R&D Systems, and commercial Procrit®. Aranesp® is significantly less active in vitro, presumably reflecting its reduced on-rate due to its increased negative charges. Similarly, Fc-EPO produced from BHK cells is less active than Fc-EPO produced from NS/0 cells, which is consistent with the observation that Fc-EPO proteins produced from BHK cells are highly sialylated resulting in increased negative charges on the proteins.

TABLE 2

| Protein | ED50 (ng/ml) | S.D. | N |
|---|---|---|---|
| EPO (NIBSC) | 0.77 | 0.35 | 22 |
| EPO (R&D Systems) | 0.6 | 0.26 | 26 |
| EPO (Procrit ®) | 0.68 | 0.15 | 6 |
| EPO (Aranesp ®) | 2.4 | 0.96 | 10 |
| Fcg2h-M1-EPO (NS/0) | 0.35 | 0.15 | 14 |
| Fcg2h-M1-EPO (BHK) | 0.94 | 0.34 | 5 |

Example 7

Pharmacokinetic Analysis of Fc-EPO Variants

Figure 8:
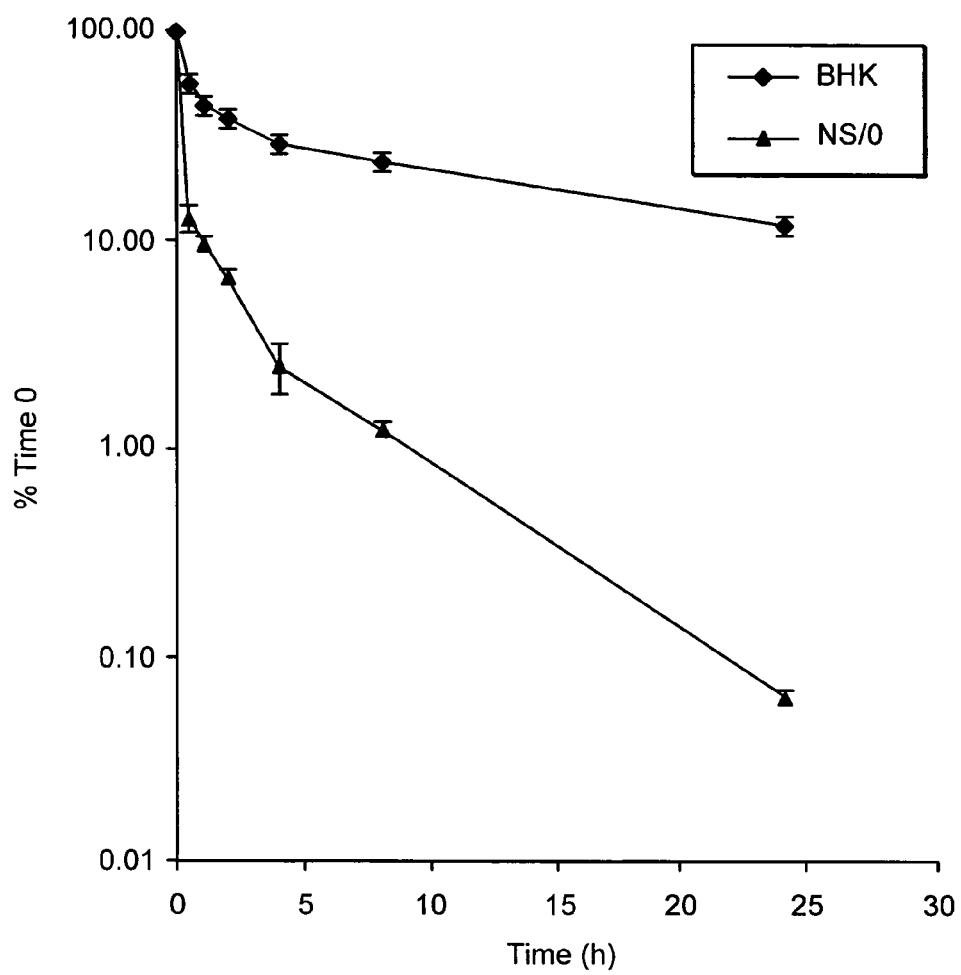
FIG. 8 depicts pharmacokinetic profiles of Fcg2h(N>Q)-EPO produced from BHK cells and Fcg2h(N>Q)-EPO produced from NS/0 cells in mice. The proteins were purified and injected intravenously at a concentration of about 14.3 µg/mouse.

The pharmacokinetic profiles of different Fc-EPO proteins synthesized in various cell lines were characterized based on the following in vivo experiments. In one experiment, as shown in FIG. 8, about 14 mcg of Fcg2h(N>Q)-EPO protein synthesized in NS/0 cells and in BHK cells were administered intravenously into Swiss-Webster mice. At various time points after administration (e.g., T=0, ½, 1, 2, 4, 8, and 24 hours after administration), blood samples were collected and serum was prepared by centrifugation. The serum concentrations of Fc-EPO were determined by ELISA using anti-Fc antibodies. As shown in FIG. 8, at 24 hours after administration, greater than 10% of the initial serum concentration of BHK-derived Fc-EPO remained in the serum, while less than 0.1% of the initial serum concentration of the NS/0-derived Fc-EPO remained in the serum.

Figure 9:
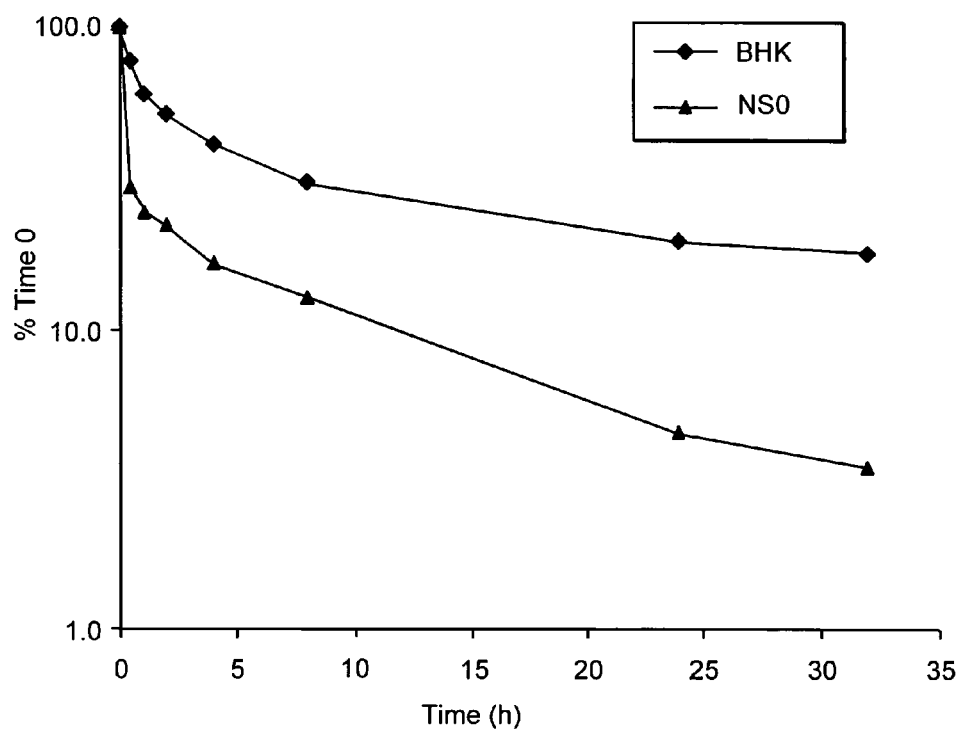
FIG. 9 depicts pharmacokinetic profiles of Fcg2h-EPO (NDS) produced from BHK cells and Fcg2h-EPO(NDS) produced from NS/0 cells in mice. The proteins were purified and injected intravenously at a concentration of about 14.3 µg/mouse.

A similar experiment was done with Fcg2h-EPO(NDS) proteins synthesized in NS/0 cells and in BHK cells. About 14 mcg of Fcg2h-EPO(NDS) protein synthesized in NS/0 cells and in BHK cells were administered intravenously into Swiss-Webster mice. Blood samples were collected at T=0, ½, 1, 2, 4, 8, 24, and 36 hours after administration and the concentrations of Fcg2h-EPO(NDS) in serum were measured by anti-Fc ELISA. As shown in FIG. 9, at 24 hours after administration, greater than 10% of the initial serum concentration of BHK-derived Fcg2h-EPO(NDS) remained in the serum, while less than 0.1% of the initial serum concentration of the NS/0-derived Fcg2h-EPO(NDS) remained in the serum.

Figure 10:
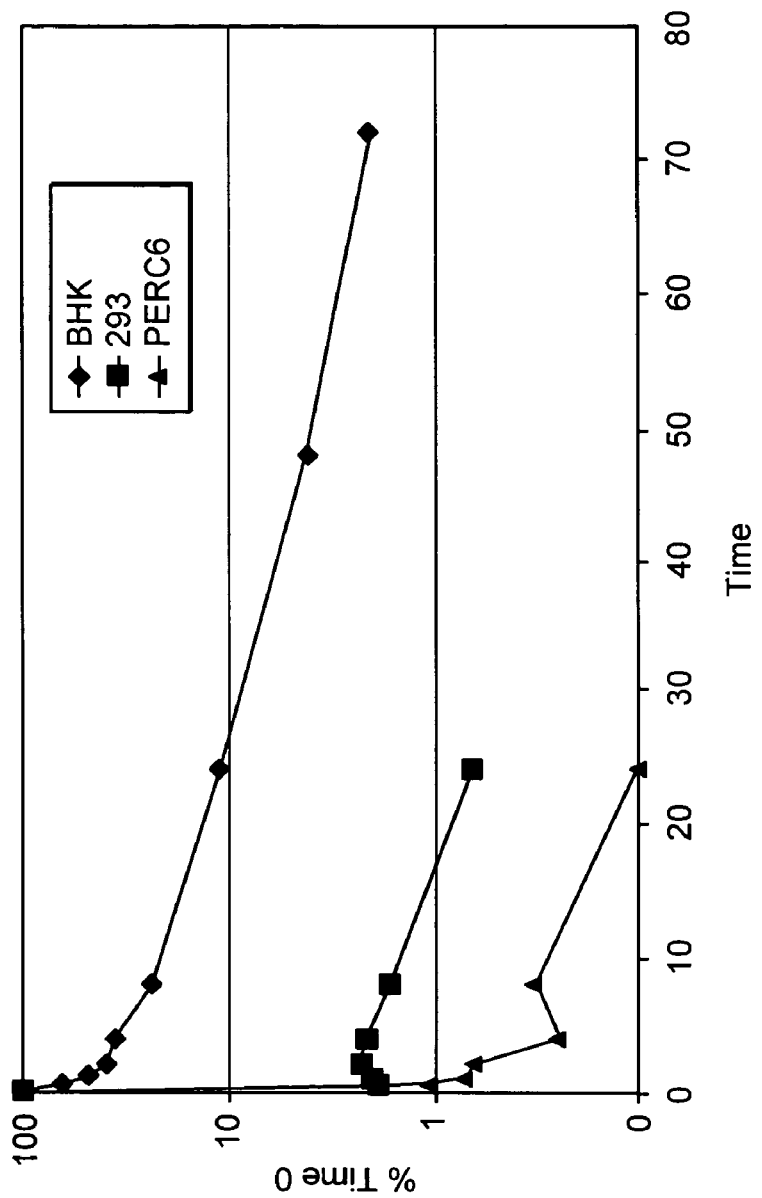
FIG. 10 depicts pharmacokinetic profiles of Fcg2h-EPO (NDS) proteins produced in BHK-21 cells, PERC6 cells, and 293 cells in mice. The proteins were purified and injected intravenously at a concentration of about 1.7 µg/mouse.

Pharmacokinetic profiles of Fcg2h-EPO(NDS) produced in BHK-21 cells, PERC6 cells, and 293 cells were also compared. Specifically, a plasmid expressing Fcg2h-Epo(NDS) was transiently transfected into BHK, 293, and PERC6 cells. The expressed Fcg2h-Epo(NDS) fusion proteins were purified from different cell lines and were injected intravenously into Swiss-Webster mice at a concentration of 1.7 micrograms per mouse. Blood samples were taken at T=0, ½, 1, 2, 4, 8, 24, 48, and 72 hours, and the concentration of Fcg2h-Epo(NDS) in serum was measured by anti-Fc ELISA. As shown in FIG. 10, at 24 hours after administration, greater than 10% of the initial serum concentration of BHK-derived Fcg2h-EPO(NDS) remained in the serum, while less than 1% of the initial serum concentration of the 293 cell-derived Fcg2h-EPO(NDS) remained in the serum, and the PerC6 cell-derived Fcg2h-EPO(NDS) was almost undetectable in the serum. Similar results were obtained with Fcg2h(N→Q)-EPO proteins produced in BHK, PerC6, and 293 cells.

Similar experiments were conducted in mice to compare pharmacokinetic profiles of Fcg2h(N→Q)-EPO, Fcg2h-EPO (NDS), Fcg2h-EPO, and Aranesp® (i.e., NESP). The Fc-EPO variants used herein were synthesized from BHK cells. It was observed that, at 48 hours after administration, less than 10% of the initial serum concentration of Aranesp® remained in serum, while greater than 10% of the initial serum concentrations of both Fcg2h(N→Q)-EPO and Fcg2h-EPO(NDS) remained in serum. These results indicate that Fcg2h(N→Q)-EPO and Fcg2h-EPO(NDS) proteins produced from BHK-21 cells have much longer serum half-lives than that of Aranesp®.

Example 8

In vivo Potency of Fc-EPO Variants

The in vivo biological activities of different Fc-EPO variants were measured by hematocrit (HCT) assays and reticulocyte assays in mice and rats.

In one HCT experiment, CD1 mice were injected intraperitoneally with Fcg2h(FN>AQ)-EPO proteins synthesized in BHK cells at dose 20 mcg/kg and 10 mcg/kg. Blood samples were taken from the mice at days 4, 7, 11, and 14, and centrifuged in capillary tubes. The amounts of sedimented RBCs were measured as fractions of the total volume. As illustrated in FIG. 4, in response to the injection of Fcg2h (FN>AQ)-EPO proteins, the hematocrits increased dramatically first, then remained steady, finally decreasing.

In another experiment, Sprague-Dawley rats were injected intraperitoneally with the following proteins synthesized in BHK cells. All animals were dosed at 42.5 mcg/kg.

1. Fcg2h-EPO
2. Fcg2h-EPO(NDS)
3. Fcg4h-EPO
4. Fcg4h(N>Q)-EPO

HCT assays were performed with the blood samples taken from the injected mice as described above. As shown in FIG. 5, in response to Fcg2h-EPO(NDS) and Fcg2h-EPO, the amount of hematocrits in the injected rats remained steady for an extended period of time, indicating that both Fcg2h-EPO (NDS) and Fcg2h-EPO proteins have prolonged serum half-lives and potent in vivo biological activity. It was also found that, as shown in FIG. 5, Fcg4h-EPO and Fcg4h(N>Q)-EPO exhibited a shorter steady period and a faster decreasing of the serum concentration compared to Fcg2h-EPO(NDS) and Fcg2h-EPO proteins.

In another experiment, CD1 mice were administered intraperitoneally with the following samples.

1. Fcg2h-EPO(NDS) from BHK cells at doses of 85 mcg/kg, 42.5 mcg/kg, and 21.25 mcg/kg
2. Fcg2h-EPO(NDS) from NS/0 cells at doses of 85 mcg/kg, 42.5 mcg/kg, and 21.25 mcg/kg
3. Aranesp® (i.e., NESP) at doses of 50 mcg/kg, 25 mcg/kg, and 12.5 mcg/kg The protein amounts were calculated on the basis of protein molecular weight without carbohydrates. In this experiment, the molecular weight of Fcg2h-EPO(NDS) protein is based on a monomer polypeptide. Accordingly, the ratio of molecular weights of Fcg2h-EPO(NDS) to NESP is about 1.71 to 1. Therefore, the dose ranges with each protein in this experiment were approximately equal.

As shown in FIG. 6, Fcg2h-EPO(NDS) proteins synthesized in BHK cells exhibited the best hematocrit profile in terms of potency and duration of effect, indicating that Fcg2h-EPO(NDS) proteins from BHK cells have longer serum half-lives and more potent in vivo activities compared to both Fcg2h-EPO(NDS) from NS/0 cells and NESP. The hematocrit profiles of Fcg2h-EPO(NDS) from NS/0 cells and NESP are comparable.

Example 9

Comparison of Fc-EPO Proteins with CH2-CH3 Domains Derived from IgG2 and from IgG4

A comparison of the cell-based erythropoietin activities of various Fc-EPO proteins revealed that fusion proteins with CH2 and CH3 domains derived from IgG4 were generally less active than corresponding proteins with CH2 and CH3 domains derived from IgG2. This conclusion is true for at least three types of Fc-EPO proteins, namely, proteins with the NDS mutations in the erythropoietin portion and synthesized in NS/0 cells (Table 3), proteins with the NDS mutations synthesized in BHK cells (Table 4), and proteins with normal erythropoietin synthesized in BHK cells (Table 5).

All of the proteins compared in the tables 3 to 5 below have a modified hinge derived from IgG1 and the M1 set of mutations at the C-terminus of the Fc portion. Activities of the proteins were determined by measuring the incorporation of tritiated thymidine into TF-1 cells stimulated by the proteins according to standard procedures described in Example 6. Activity is expressed as an ED50 in nanograms/ml of erythropoietin moieties.

TABLE 3

Cell-based activities of Fc-EPO fusion proteins with the NDS mutations and synthesized in NS/0 cells

| Fc-EPO Proteins | ED50 (ng of EPO/ml) | S.D | Number of Experiments |
| --- | --- | --- | --- |
| Fcg2h-M1-EPO(NDS) NS0 preparation 1 | 0.60 | 0.17 | 5 |
| Fcg2h-M1-EPO(NDS) NS0 preparation 2 | 0.57 | 0.33 | 13 |
| Fcg2h-M1-EPO(NDS) NS0 preparation 3 | 0.54 | 0.34 | 8 |
| Fcg2h-M1-EPO(NDS) NS0 preparation 4 | 0.36 | 0.11 | 5 |
| Fcg4h-M1-EPO(NDS) NS0 preparation 1 | 0.96 | 0.21 | 4 |

TABLE 4

Cell-based activities of Fc-EPO fusion proteins with the NDS mutations and synthesized in BHK cells

| Fc-EPO Proteins | ED50 (ng of EPO/ml) | S.D. | Number of Experiments |
|---|---|---|---|
| Fcg2h-M1-EPO(NDS) BHK preparation 1 | 0.81 | 0.23 | 11 |
| Fcg2h-M1-EPO(NDS) BHK preparation 2 | 2.17 | 1.23 | 6 |
| Fcg2h-M1-EPO(NDS) BHK preparation 3 | 1.16 | 0.28 | 5 |
| Fcg2h-M1-EPO(NDS) BHK preparation 4 | 0.89 | 0.44 | 4 |
| Fcg2h-M1-EPO(NDS) BHK preparation 5 | 1.09 | 0.41 | 4 |
| Fcg4h-M1-EPO(NDS) BHK preparation 1 | 6.24 | 2.34 | 6 |

TABLE 5

Cell-based activities of Fc-EPO fusion proteins with wild-type EPO and synthesized in BHK cells

| Fc-EPO Proteins | ED50 (ng of EPO/ml) | S.D. | Number of Experiments |
|---|---|---|---|
| Fcg2h-M1-EPO BHK preparation 1 | 0.84 | 0.28 | 4 |
| Fcg2h-M1-EPO BHK preparation 2 | 0.95 | 0.32 | 7 |
| Fcg2h-M1-EPO BHK preparation 3 | 0.72 | 0.27 | 3 |
| Fcg2h-M1-EPO BHK preparation 4 | 0.95 | 0.17 | 3 |
| Fcg2h-M1-EPO BHK preparation 5 | 0.43 | 0.18 | 2 |
| Fcg4h-M1-EPO BHK preparation 1 | 1.09 | 0.31 | 7 |
| Fcg4h-M1-EPO BHK preparation 2 | 1.53 | 0.35 | 6 |

Activity data from in vitro cell-based assays usually can suggest pharmacokinetic profiles and in vivo potencies of erythropoietin-containing proteins. Generally, a decreased in vitro activity in a cell-based assay indicates a reduced on-rate for the EPO receptor, which correlates with improved pharmacokinetic properties (e.g., extended half-life) and enhanced in vivo activity. However, the decreased in vitro activities of Fc-EPO fusion proteins with IgG4-derived CH2 and CH3 domains do not correlate with improved pharmacokinetics and enhanced in vivo biological activities. It was found that the pharmacokinetic profiles of Fc-EPO fusion proteins with IgG4-derived CH2 and CH3 domains were generally indistinguishable from the corresponding proteins with IgG2-derived CH2 and CH3 domains. It was also found that Fc-EPO fusion proteins with IgG4-derived CH2 and CH3 domains generally had less activity in vivo compared to the corresponding proteins with IgG2-derived CH2 and CH3 domains (see FIG. 5).

Example 10

The Effects of Elimination of the Glycosylation Site in the Fc Portion

Experiments were conducted to test the effects of elimination of the glycosylation site in the Fc portion on in vitro activity, pharmacokinetics, and in vivo potency. In particular, Fc-EPO fusion proteins containing either IgG2-derived CH2 and CH3 domains or IgG4-derived CH2 and CH3 domains were tested. The asparagine within the Gln-Phe-Asn-Ser (SEQ ID NO:16) amino acid sequence of IgG2 or IgG4, which corresponds to Asn297 of IgG1, was replaced with a glutamine. In most experiments, the phenylalanine with the Gln-Phe-Asn-Ser (SEQ ID NO:16) amino acid sequence was replaced with alanine to eliminate possible non-self T-cell epitopes that may result from the mutation of the asparagine. As shown in Table 6, in cell-based in vitro assays, the ED50 values of Fc-EPO proteins with the FN>AQ mutation eliminating the N-linked glycosylation site in the Fc portion are generally about 5-fold lower than that of Fc-EPO proteins without the mutation, indicating elimination of the N-linked glycosylation site resulted in a decreased in vitro activity in cell-based assays.

Experiments were also conducted to test the effects of elimination of the N-linked glycosylation on pharmacokinetics and in vivo potency. CD1 mice were treated with Fcg2h-M1-EPO, Fcg2h-M1-EPO(NDS), and Fcg2h(N>Q)-M1-EPO proteins synthesized in BHK cells at a dose of 42 mcg/kg each. It was observed that Fcg2h(N>Q)-M1-EPO protein showed better pharmacokinetic profile than the corresponding protein without N>Q mutation. Therefore, N>Q mutation, which eliminates the N-linked glycosylation in the IgG2-derived Fc portion, resulted in improved pharmacokinetics (e.g., extended serum half-life). The extended serum half-life cannot be explained by an effect on binding to Fc receptors because IgG2-derived CH2 and CH3 domains already have essentially undetectable Fc-receptor binding.

TABLE 6

Elimination of the glycosylation site in the Fc portion reduces in vitro cell-based activity of the Fc-EPO fusion proteins

| Fc-EPO fusion proteins | ED50 (ng of EPO/ml) | S.D. | Number of Experiments |
|---|---|---|---|
| Fcg2h-EPO BHK preparation 1 | 0.84 | 0.28 | 4 |
| Fcg2h-EPO BHK preparation 2 | 0.95 | 0.32 | 7 |
| Fcg2h-EPO BHK preparation 3 | 0.72 | 0.27 | 3 |
| Fcg2h-EPO BHK preparation 4 | 0.95 | 0.17 | 3 |
| Fcg2h-EPO BHK preparation 5 | 0.43 | 0.18 | 2 |
| Fcg2h(FN > AQ)-EPO BHK Preparation 1 | 6.75 | 2.57 | 9 |
| Fcg2h(FN > AQ)-EPO BHK Preparation 2 | 7.38 | 1.48 | 4 |
| Fcg2h(FN > AQ)-EPO BHK Preparation 3 | 7.01 | 4.64 | 9 |
| Fcg2h(FN > AQ)-EPO BHK Preparation 4 | 3.02 | 0.88 | 5 |
| Fcg2h(FN > AQ)-EPO BHK Preparation 5 | 2.77 | 1.75 | 5 |
| Fcg2h(FN > AQ)-EPO BHK Preparation 6 | 5.07 | 1.64 | 4 |
| Fcg2h(FN > AQ)-EPO BHK Preparation 7 | 2.53 | 0.53 | 5 |

TABLE 6-continued Elimination of the glycosylation site in the Fc portion reduces in vitro cell-based activity of the Fc-EPO fusion proteins

| Fc-EPO fusion proteins | ED50 (ng of EPO/ml) | S.D. | Number of Experiments |
|---|---|---|---|
| Fcg2h(FN > AQ)-EPO BHK Preparation 8 | 2.92 | 0.52 | 5 |
| Fcg2h(FN > AQ)-EPO BHK Preparation 9 | 1.55 | 0.66 | 5 |
| Fcg2h(FN > AQ)-EPO BHK Preparation 10 | 2.37 | 1.78 | 8 |
| Fcg4h-M1-EPO BHK preparation 1 | 1.09 | 0.31 | 7 |
| Fcg4h-M1-EPO BHK preparation 2 | 1.53 | 0.35 | 6 |
| Fcg4h(FN > AQ)-M1-EPO BHK preparation 1 | 17.16 | | 1 |
| Fcg4h(FN > AQ)-M1-EPO BHK preparation 2 | 5.87 | 2.71 | 7 |
| Fcg4h(FN > AQ)-M1-EPO BHK preparation 3 | 3.79 | 0.93 | 5 |
| Fcg4h(FN > AQ)-M1-EPO BHK preparation 4 | 4.78 | 3.42 | 8 |

These effects are unexpected and surprising because the effects caused by elimination of the N-linked glycosylation in the IgG2 and IgG4 derived Fc portions are most consistent with reduced on-rate for the erythropoietin receptor. Without wishing to be bound by theory, elimination of the N-linked glycosylation in the IgG2 and IgG4 derived Fc portions may cause an overall conformational change on the Fc-EPO fusion protein.

Example 11

Treatment of Beagle Dogs with Fc-EPO Fusion Proteins Synthesized in BHK Cells

Fc-EPO fusion proteins were administered to beagle dogs to test for effects on hematocrits, reticulocyte counts, and other blood parameters. Specifically, Fcg2h(FN→AQ)-EPO proteins were purified from two independently stably transfected BHK cell lines, clone 65 and clone 187, and administered into beagle dogs intravenously. One male and one female beagle dog were injected with each preparation according to the following schedule:

Day 0: 3 micrograms/kg
Day 16: 10 micrograms/kg
Day 23: 100 micrograms/kg

At various time points after each administration, approximately 2 ml of blood were collected and blood parameters, such as, hematocrits, reticulocyte counts, and other blood parameters, were measured.

Figure 11:
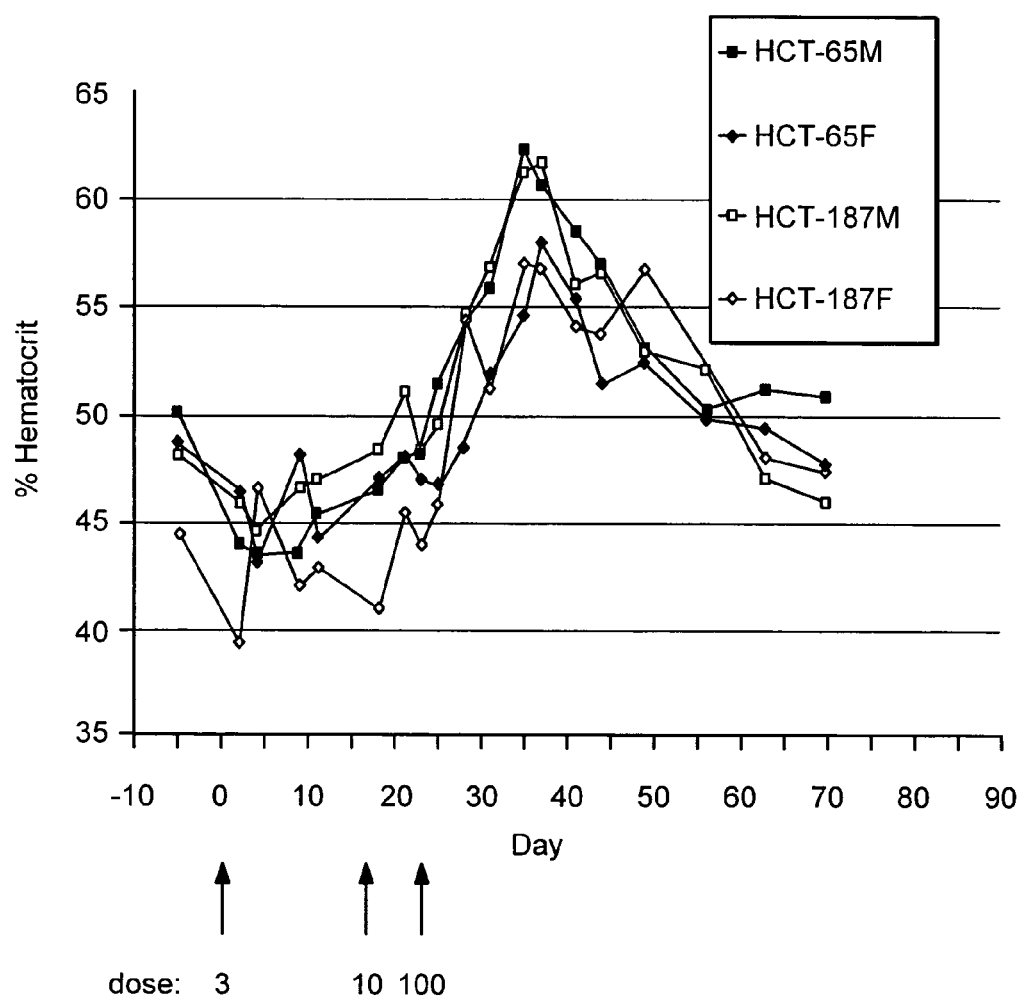
FIG. 11 depicts hematocrit responses in beagle dogs following treatment with Fcg2h(FN→AQ)-EPO proteins synthesized in BHK cells.

The hematocrit responses following treatment are shown in FIG. 11. After dosing with 3 mcg/kg of Fc-EPO fusion proteins, blood parameters did not increase from the normal range. Within one week after dosing with 10 mcg/kg, reticulocyte counts increased to over 3% of total blood volume in three of the four animals, and the hematocrits increased to 51 in one animal. Other blood parameters did not increase from the normal range. After dosing with 100 mcg/kg, hematocrit counts rapidly elevated, reaching peak levels of 57 to 62 and remaining above the normal range for five to six weeks. Reticulocyte counts remained elevated for two to three weeks.

For each animal, the number of red blood cells per microliter of blood and the hemoglobin, measured in grams per deciliter, were proportional to the amount of hematocrits. These results indicated that Fc-EPO proteins stimulate the production of red blood cells of normal size with normal hemoglobin content.

Example 12

Purification of Fc-EPO Proteins for Clinical Use

Fc-EPO proteins are purified following standard GMP procedures known to persons skilled in the art. BHK-21 cells, from a banked production clone, are cultured in DMEM/F-12 medium (Invitrogen) supplemented with additional 2.5 mM L-glutamine (Invitrogen), 2 g/l of each HyPep 1501 and HyPep 4601 (Quest International, Chicago, Ill.), 10 µl/l ethanolamine (Sigma), and 5 µM Tropolone (Sigma) for 7-10 days in batch culture while maintaining high cell viability (e.g., above 80%). The conditioned medium is harvested and clarified by normal-flow-filtration, and is loaded onto a pre-equilibrated Protein A Sepharose Fast-Flow column (Pharmacia), which captures the fusion protein based on the affinity of Protein A for the Fc portion. The column is washed extensively with 15 column volumes of sodium phosphate buffer containing 150 mM sodium phosphate and 100 mM NaCl at neutral pH. The bound protein is eluted at low pH with further 15 column volumes of acidic sodium phosphate buffer of pH 2.5-3 but also containing 150 mM sodium phosphate and 100 mM NaCl.

For viral inactivation, the pH of the pooled peak fractions is adjusted to pH 3.8 and incubated for a further 30 minutes at room temperature. After 30-minute incubation, the pooled fractions are neutralized and sterile filtered, then applied to a Q-Sepharose Fast-Flow anion exchange column (Pharmacia), which exploits the acidic pI of the Fc-EPO protein as a result of its extensive sialylation to effectively remove potential contaminants co-eluted with Fc-EPO proteins. Specifically, the neutralized fractions are loaded on a Q-Sepharose Fast-Flow anion exchange column (Pharmacia) at pH 5.0 and eluted with a gradient of NaCl solution. The fractions of Fc-EPO are then collected and pooled for subsequent analysis and for further purification process. For example, the high salt strip from the Q-Sepharose column is applied to a reversed phase chromatography column to remove excess NaCl. The diluted eluant from the reversed phase column is further applied to a second Q-Sepharose Fast Flow (Pharmacia, 3 cm×9 cm) column.

Potential virus particles are then removed from the pool by nano-filtration (e.g., Viresolve by Millipore). Optionally, further purification steps, such as a hydroxyapatite column or a phenyl-boronate column (binds cis-diols), can be used. Finally, the purified proteins are concentrated to a desired concentration using ultrafiltration and then diafiltered into a suitable formulation buffer. The material is finally sterile filtered, and dispensed into vials to a predetermined volume.

Example 13

Stress Test to Determine the Stability of Fc-EPO Protein Formulations

Vials containing an exemplary sample Fc-EPO formulation or a reference Fc-EPO formulation are stored at 40° C. and 75% relative atmospheric humidity, and for defined storage times (e.g., 0 weeks, 4 weeks, 8 weeks, etc.). An aliquot sample is taken from each vial after certain storage time and is analyzed. The samples are assessed visually under direct illumination with a cold light source for cloudiness. The cloudiness is further determined by measuring the absorption at 350 nm and 550 nm. In addition, the condition of the Fc-EPO protein in the samples and the presence of protein degradation products are analyzed by analytical size exclusion chromatography (HPLC-SEC). It is found that a formulation containing 0.5 mg/ml Fc-EPO, 10 mM Citrate pH 6.2, 100 mM Glycine, 100 mM NaCl, 0.01% w/v polysorbate 20 had significantly increased stability compared to a reference solution.

Example 14

A Phase I Study of the Fcg2h(FN>AQ)-M1-EPO Fusion Protein in Humans

A Phase I clinical trial of the Fcg2h(FN>AQ)-M1-EPO fusion protein in humans is performed as follows. Pharmacokinetic parameters are determined essentially as described for Aranesp® by MacDougall et al. (1999) *J. Am. Soc. Nephrol.* 10:2392-2395, the teachings of which are hereby incorporated by reference. The terminal serum half-life of intravenously injected Fcg2h(FN>AQ)-M1-EPO fusion protein (dosed at 1 mcg/kg) in humans is found to be between about 20 and 30 hours. Thus, a dose of 1 mcg/kg, or about 70 mcg in an adult anemic patient, results in an initial serum concentration of about 10 ng/ml. Since the normal human erythropoietin concentration is about 0.04 to 0.25 ng/ml (Cazzola et al., (1998) *Blood* 91:2139-2145), pharmacologically active levels of the Fc-EPO protein remain in the patient's system for at least 5-10 days.

Example 15

A Phase II Dose Finding and Dose Scheduling Study of the Fcg2h(FN>AQ)-M1-EPO Fusion Proteins Multicenter, randomized, sequential dose-escalation studies are initiated to investigate the optimum dose and dose schedule for the Fcg2h(FN>AQ)-M1-EPO fusion protein when administered by subcutaneous or intravenous injection in patients with chronic renal failure (CRF) receiving dialysis.

In clinical practice, it is generally convenient to tailor the administration of the Fcg2h(FN>AQ)-M1-EPO fusion protein to an individual anemic patient according to the following guidelines. An initial dose is administered and blood parameters such as the hematocrit, hemoglobin, reticulocyte counts, and platelet counts are monitored. The initial dose is typically between about 0.3 and 3 mcg/kg. A convenient initial dose is 1 mcg/kg. If the increase in hematocrit is less than 5 to 6 percent of blood volume after 8 weeks of therapy, the dose should be increased. If the increase in hematocrit is greater than 4 percent of blood volume in a 2-week period, or if the hematocrit is approaching 36%, the dose should be reduced.

An exemplary dosing schedule is as follows.
  Once per week dosing: 0.075, 0.225, 0.45, 0.75, 1.5 and 4.5 mcg/kg/dose.
  Once per two week dosing: 0.075, 0.225, 0.45, 0.75, 1.5 and 4.5 mcg/kg/dose.
  Once per month dosing: 0.45, 0.75, 1.5 and 4.5 mcg/kg/dose.

The studies are carried out in two parts. The first part is a dose-escalation study designed to evaluate the dose of the Fcg2h(FN>AQ)-M1-EPO fusion protein given either once per week, once per two weeks, or once per month which increases hemoglobin at an optimum rate over four weeks (greater than or equal to 1 g/dL but less than 3 g/dL). The second part of each study is designed to determine the doses required (when administered once per week, once per two weeks, or once per month by either the intravenous or subcutaneous routes of administration) to maintain the hematocrit at the therapeutic target.

---

We claim:

1. A population of purified Fc-EPO fusion proteins suitable for administration to a mammal, the Fc-EPO fusion proteins comprising an Fc portion towards the N-terminus of the Fc-EPO fusion proteins and an erythropoietin portion towards the C-terminus of the Fc-EPO fusion proteins, said population having an average of 11-28 sialic acid residues per purified Fc-EPO fusion protein,
    wherein the Fc portion comprises a CH2 domain derived from an IgG2 heavy chain, the CH2 domain comprising a mutation of the glycosylation site within the CH2 domain of the IgG2 heavy chain,
    wherein the mutation is of an asparagine within the Gln-Phe-Asn-Ser (SEQ ID NO:16) amino acid sequence within the CH2 domain of the IgG2 heavy chain.

2. The population of purified Fc-EPO fusion proteins of claim 1, wherein the asparagine is replaced with a glutamine.

3. The population of purified Fc-EPO fusion proteins of claim 2, wherein the Gln-Phe-Asn-Ser (SEQ ID NO:16) amino acid sequence within the CH2 domain of the IgG2 heavy chain is replaced with a Gln-Ala-Gln-Ser (SEQ ID NO:17) amino acid sequence.

4. The population of purified Fc-EPO fusion proteins of claim 3, wherein the Fc portion further comprises a hinge region derived from a human IgG1 heavy chain, and further wherein the Fc portion is derived from an IgG sequence in which the Leu-Ser-Leu-Ser (SEQ ID NO:20) amino acid sequence near the C-terminus of the Fc portion is replaced with an Ala-Thr-Ala-Thr (SEQ ID NO:21) amino acid sequence, and wherein the Fc portion C-terminal lysine residue is replaced with alanine.

* * * * *